(12) United States Patent
Stephan et al.

(10) Patent No.: US 12,209,288 B2
(45) Date of Patent: *Jan. 28, 2025

(54) METHODS FOR SEQUENCING SAMPLES

(71) Applicant: Aqtual, Inc., Orinda, CA (US)

(72) Inventors: Dietrich Stephan, San Francisco, CA (US); Vern Norviel, San Francisco, CA (US); Janet Warrington, Los Altos, CA (US); Doug Dolginow, Basalt, CO (US)

(73) Assignee: Aqtual, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/356,906

(22) Filed: Jul. 21, 2023

(65) Prior Publication Data

US 2023/0407408 A1 Dec. 21, 2023

Related U.S. Application Data

(60) Continuation of application No. 16/154,307, filed on Oct. 8, 2018, now Pat. No. 11,965,211, which is a continuation of application No. 15/183,655, filed on Jun. 15, 2016, now abandoned, which is a division of application No. 14/927,254, filed on Oct. 29, 2015, now abandoned, which is a continuation of application No. 14/075,996, filed on Nov. 8, 2013, now abandoned, which is a continuation of application No. 13/060,425, filed as application No. PCT/US2009/056101 on Sep. 4, 2009, now Pat. No. 8,583,380.

(60) Provisional application No. 61/231,287, filed on Aug. 4, 2009, provisional application No. 61/173,179, filed on Apr. 27, 2009, provisional application No. 61/155,477, filed on Feb. 25, 2009, provisional application No. 61/094,855, filed on Sep. 5, 2008.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57484* (2013.01); *C12Q 2600/106* (2013.01); *C12Q 2600/112* (2013.01); *C12Q 2600/136* (2013.01); *C12Q 2600/142* (2013.01); *C12Q 2600/154* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 3,575,220 A | 4/1971 | Davis et al. |
| 3,996,345 A | 12/1976 | Ullman et al. |
| 4,351,760 A | 9/1982 | Khanna et al. |
| 4,458,066 A | 7/1984 | Caruthers et al. |
| 4,683,202 A | 7/1987 | Mullis |
| 4,739,044 A | 4/1988 | Stabinsky |
| 4,757,141 A | 7/1988 | Fung et al. |
| 4,889,818 A | 12/1989 | Gelfand et al. |
| 4,997,928 A | 3/1991 | Hobbs, Jr. |
| 5,231,191 A | 7/1993 | Woo et al. |
| 5,487,972 A | 1/1996 | Gelfand et al. |
| 5,496,699 A | 3/1996 | Sorenson |
| 5,538,848 A | 7/1996 | Livak et al. |
| 5,539,083 A | 7/1996 | Cook et al. |
| 5,585,069 A | 12/1996 | Zanzucchi et al. |
| 5,635,400 A | 6/1997 | Brenner |
| 5,677,152 A | 10/1997 | Birch et al. |
| 5,723,591 A | 3/1998 | Livak et al. |
| 5,750,341 A | 5/1998 | Macevicz |
| 5,773,258 A | 6/1998 | Birch et al. |
| 5,789,206 A | 8/1998 | Tavtigian et al. |
| 5,789,224 A | 8/1998 | Gelfand et al. |
| 5,804,375 A | 9/1998 | Gelfand et al. |
| 5,827,480 A | 10/1998 | Haff et al. |
| 5,925,517 A | 7/1999 | Tyagi et al. |
| 5,952,170 A | 9/1999 | Stroun et al. |
| 5,981,179 A | 11/1999 | Lorinez et al. |
| 5,994,056 A | 11/1999 | Higuchi |
| 6,008,002 A | 12/1999 | Bodey |
| 6,030,787 A | 2/2000 | Livak et al. |

(Continued)

FOREIGN PATENT DOCUMENTS

| | | |
|---|---|---|
| EP | 0799897 A1 | 10/1997 |
| EP | 1207209 A2 | 5/2002 |

(Continued)

OTHER PUBLICATIONS

Longley et al., "Classes of c-KIT activating mutations: proposed mechanisms of action and implications for disease classification and therapy" 25 Leukemia Research 571-576 (Year: 2001).*

(Continued)

*Primary Examiner* — Nancy J Leith
(74) *Attorney, Agent, or Firm* — WILSON SONSINI GOODRICH & ROSATI

(57) ABSTRACT

Personalized medicine involves the use of a patient's molecular markers to guide treatment regimens for the patient. The scientific literature provides multiple examples of correlations between drug treatment efficacy and the presence or absence of molecular markers in a patient sample. Methods are provided herein that permit efficient dissemination of scientific findings regarding treatment efficacy and molecular markers found in patient tumors to health care providers.

19 Claims, 13 Drawing Sheets

(56) References Cited

U.S. PATENT DOCUMENTS

| | | |
|---|---|---|
| 6,040,138 A | 3/2000 | Lockhart et al. |
| 6,063,604 A | 5/2000 | Wick et al. |
| 6,090,591 A | 7/2000 | Burg et al. |
| 6,103,406 A | 8/2000 | Kumagai |
| 6,127,155 A | 10/2000 | Gelfand et al. |
| 6,156,504 A | 12/2000 | Gocke et al. |
| 6,171,785 B1 | 1/2001 | Higuchi |
| 6,184,934 B1 | 2/2001 | Nishiki |
| 6,204,375 B1 | 3/2001 | Lader |
| 6,214,979 B1 | 4/2001 | Gelfand et al. |
| 6,217,866 B1 | 4/2001 | Schlessinger et al. |
| 6,221,589 B1 | 4/2001 | Lane et al. |
| 6,262,242 B1 | 7/2001 | Steck et al. |
| 6,303,312 B1 | 10/2001 | Dervan et al. |
| 6,306,597 B1 | 10/2001 | Macevicz |
| 6,321,894 B1 | 11/2001 | Johnsson |
| 6,410,231 B1 | 6/2002 | Arnold et al. |
| 6,410,243 B1 | 6/2002 | Wyrick et al. |
| 6,482,795 B1 | 11/2002 | Steck et al. |
| 6,488,895 B1 | 12/2002 | Kennedy |
| 6,492,161 B1 | 12/2002 | Hjoerleifsdottir et al. |
| 6,492,346 B1 | 12/2002 | Hedgpeth et al. |
| 6,521,409 B1 | 2/2003 | Gocke et al. |
| 6,524,456 B1 | 2/2003 | Ramsey et al. |
| 6,565,727 B1 | 5/2003 | Shenderov |
| 6,582,919 B2 | 6/2003 | Danenberg |
| 6,586,177 B1 | 7/2003 | Shuber |
| 6,759,217 B2 | 7/2004 | Kopreski et al. |
| 6,773,566 B2 | 8/2004 | Shenderov |
| 6,812,018 B2 | 11/2004 | Wicher et al. |
| 6,818,425 B2 | 11/2004 | Hjorleifsdottir et al. |
| 6,849,403 B1 | 2/2005 | Shuber |
| 6,858,394 B1 | 2/2005 | Chee et al. |
| 6,911,132 B2 | 6/2005 | Pamula et al. |
| 6,949,342 B2 | 9/2005 | Golub et al. |
| 7,041,481 B2 | 5/2006 | Anderson et al. |
| 7,056,673 B2 | 6/2006 | Kamme et al. |
| 7,105,293 B2 | 9/2006 | Ramaswamy et al. |
| 7,115,400 B1 | 10/2006 | Adessi et al. |
| 7,129,040 B2 | 10/2006 | Steck et al. |
| 7,138,226 B2 | 11/2006 | Vincek et al. |
| 7,141,377 B2 | 11/2006 | Gelfand et al. |
| 7,153,658 B2 | 12/2006 | Andersen et al. |
| 7,208,275 B2 | 4/2007 | Gocke et al. |
| 7,211,390 B2 | 5/2007 | Rothberg et al. |
| 7,217,795 B2 | 5/2007 | Steck et al. |
| 7,223,833 B1 | 5/2007 | Nielsen et al. |
| 7,232,653 B1 | 6/2007 | Austrup et al. |
| 7,232,656 B2 | 6/2007 | Balasubramanian et al. |
| 7,244,559 B2 | 7/2007 | Rothberg et al. |
| 7,264,929 B2 | 9/2007 | Rothberg et al. |
| 7,268,167 B2 | 9/2007 | Higuchi et al. |
| 7,294,468 B2 | 11/2007 | Bell et al. |
| 7,303,901 B2 | 12/2007 | Hjorleifsdottir et al. |
| 7,323,305 B2 | 1/2008 | Leamon et al. |
| 7,324,926 B2 | 1/2008 | Tamayo et al. |
| 7,329,495 B2 | 2/2008 | Chen et al. |
| 7,332,288 B2 | 2/2008 | Terstappen et al. |
| 7,375,140 B2 | 5/2008 | Higuchi et al. |
| 7,381,818 B2 | 6/2008 | Lokhov et al. |
| 7,410,764 B2 | 8/2008 | Gocke et al. |
| 7,442,507 B2 | 10/2008 | Polsky et al. |
| 7,445,900 B2 | 11/2008 | Gelfand et al. |
| 7,485,442 B2 | 2/2009 | Afonina et al. |
| 7,582,739 B2 | 9/2009 | Lukhtanov et al. |
| 7,601,821 B2 | 10/2009 | Andersen et al. |
| 7,622,281 B2 | 11/2009 | Ronaghi et al. |
| 7,638,276 B2 | 12/2009 | Griffiths et al. |
| 7,662,553 B2 | 2/2010 | Lenz |
| 7,666,593 B2 | 2/2010 | Lapidus |
| 7,700,283 B2 | 4/2010 | Evans et al. |
| 7,700,286 B2 | 4/2010 | Stroun et al. |
| 7,700,323 B2 | 4/2010 | Willis et al. |
| 7,717,615 B2 | 5/2010 | Higuchi et al. |
| 7,732,576 B2 | 6/2010 | Steck et al. |
| 7,745,128 B2 | 6/2010 | Guo et al. |
| 7,772,287 B2 | 8/2010 | Higuchi et al. |
| RE41,780 E | 9/2010 | Anderson et al. |
| 7,842,248 B2 | 11/2010 | McAvoy et al. |
| 7,908,091 B2 | 3/2011 | Harvey et al. |
| 7,932,026 B2 | 4/2011 | Seshagiri |
| 7,935,487 B2 | 5/2011 | Gocke et al. |
| 7,947,819 B2 | 5/2011 | Stratton et al. |
| 7,948,015 B2 | 5/2011 | Rothberg et al. |
| 7,981,618 B2 | 7/2011 | Yu et al. |
| 7,993,842 B2 | 8/2011 | Mckernan et al. |
| 8,067,159 B2 | 11/2011 | Brown et al. |
| 8,198,028 B2 | 6/2012 | Rigatti et al. |
| 8,252,539 B2 | 8/2012 | Quake et al. |
| 8,278,071 B2 | 10/2012 | Brown et al. |
| 8,349,276 B2 | 1/2013 | Pamula et al. |
| 8,349,563 B2 | 1/2013 | Lao et al. |
| 8,399,192 B2 | 3/2013 | Rigatti et al. |
| 8,583,380 B2 | 11/2013 | Stephan et al. |
| 8,834,873 B2 | 9/2014 | Petricoin, III et al. |
| 9,090,648 B2 | 7/2015 | Behr et al. |
| 9,217,167 B2 | 12/2015 | Heller et al. |
| 9,255,291 B2 | 2/2016 | Toloue et al. |
| 9,309,556 B2 | 4/2016 | Myllykangas et al. |
| 9,340,830 B2 | 5/2016 | Lipson et al. |
| 9,650,628 B2 | 5/2017 | Amorese et al. |
| 10,072,287 B2 | 9/2018 | Zhou et al. |
| 11,965,211 B2 * | 4/2024 | Stephan ............... C12Q 1/6886 |
| 2001/0034023 A1 | 10/2001 | Stanton et al. |
| 2002/0012921 A1 | 1/2002 | Stanton |
| 2002/0048755 A1 | 4/2002 | Cohen |
| 2002/0115073 A1 | 8/2002 | Papadopoulos et al. |
| 2002/0120409 A1 | 8/2002 | Cao et al. |
| 2003/0082543 A1 | 5/2003 | Su et al. |
| 2003/0093819 A1 | 5/2003 | D'Andrea et al. |
| 2003/0143600 A1 | 7/2003 | Gocke et al. |
| 2003/0165940 A1 | 9/2003 | Traverso et al. |
| 2003/0211530 A1 | 11/2003 | Danenberg |
| 2003/0224385 A1 | 12/2003 | Pihan |
| 2003/0224439 A1 | 12/2003 | Lafferty et al. |
| 2004/0110193 A1 | 6/2004 | Castle et al. |
| 2004/0137539 A1 | 7/2004 | Bradford |
| 2005/0019785 A1 | 1/2005 | Baker et al. |
| 2005/0021240 A1 | 1/2005 | Berlin et al. |
| 2005/0153317 A1 | 7/2005 | Denise et al. |
| 2005/0181377 A1 | 8/2005 | Markovic |
| 2005/0186584 A1 | 8/2005 | Stratton et al. |
| 2005/0191656 A1 | 9/2005 | Drmanac et al. |
| 2005/0246314 A1 | 11/2005 | Eder et al. |
| 2005/0260646 A1 | 11/2005 | Baker et al. |
| 2005/0272083 A1 | 12/2005 | Seshagiri |
| 2005/0287543 A1 | 12/2005 | Yu et al. |
| 2006/0008824 A1 | 1/2006 | Ronaghi et al. |
| 2006/0008834 A1 | 1/2006 | Margus et al. |
| 2006/0024721 A1 | 2/2006 | Pedersen |
| 2006/0046258 A1 | 3/2006 | Lapidus et al. |
| 2006/0068406 A1 | 3/2006 | Affholter et al. |
| 2006/0134674 A1 | 6/2006 | Huang et al. |
| 2006/0184489 A1 | 8/2006 | Weiner et al. |
| 2006/0188909 A1 | 8/2006 | Willey et al. |
| 2006/0195269 A1 | 8/2006 | Yeatman et al. |
| 2006/0254933 A1 | 11/2006 | Adachi et al. |
| 2006/0278241 A1 | 12/2006 | Ruano |
| 2007/0042369 A1 | 2/2007 | Reese et al. |
| 2007/0054333 A1 | 3/2007 | Steck et al. |
| 2007/0065846 A1 | 3/2007 | Baker et al. |
| 2007/0071762 A1 | 3/2007 | Ts'O et al. |
| 2007/0087394 A1 | 4/2007 | Siena et al. |
| 2007/0092902 A1 | 4/2007 | Di et al. |
| 2007/0117121 A1 | 5/2007 | Hutchison et al. |
| 2007/0141067 A1 | 6/2007 | Markovic |
| 2007/0253951 A1 | 11/2007 | Ng et al. |
| 2007/0254295 A1 | 11/2007 | Harvey et al. |
| 2007/0269817 A1 | 11/2007 | Shapero |
| 2008/0014146 A1 | 1/2008 | Von Hoff et al. |
| 2008/0044813 A1 | 2/2008 | Jansson et al. |
| 2008/0065411 A1 | 3/2008 | Keeling et al. |
| 2008/0090239 A1 | 4/2008 | Shoemaker et al. |
| 2008/0090244 A1 | 4/2008 | Knapp et al. |

(56) References Cited

U.S. PATENT DOCUMENTS

| | | |
|---|---|---|
| 2008/0124721 A1 | 5/2008 | Fuchs et al. |
| 2008/0131887 A1 | 6/2008 | Stephan et al. |
| 2008/0138805 A1 | 6/2008 | Condeelis |
| 2008/0160580 A1 | 7/2008 | Adessi et al. |
| 2008/0161420 A1 | 7/2008 | Shuber |
| 2008/0176209 A1 | 7/2008 | Muller et al. |
| 2008/0177608 A1 | 7/2008 | Keeling |
| 2008/0207615 A1 | 8/2008 | Bell et al. |
| 2008/0213774 A1 | 9/2008 | Chen et al. |
| 2008/0242622 A1 | 10/2008 | Lowe et al. |
| 2008/0255243 A1 | 10/2008 | Petricoin et al. |
| 2008/0262062 A1 | 10/2008 | Ossovskaya et al. |
| 2008/0268449 A1 | 10/2008 | Hoon |
| 2008/0286795 A1 | 11/2008 | Kawashima et al. |
| 2008/0293055 A1 | 11/2008 | Freeman et al. |
| 2009/0002608 A1 | 1/2009 | Kameyama et al. |
| 2009/0010508 A1 | 1/2009 | Inoue et al. |
| 2009/0026082 A1 | 1/2009 | Rothberg et al. |
| 2009/0029377 A1 | 1/2009 | Lo et al. |
| 2009/0035777 A1 | 2/2009 | Kokoris et al. |
| 2009/0035792 A1 | 2/2009 | Singh et al. |
| 2009/0062138 A1 | 3/2009 | Curry et al. |
| 2009/0075267 A1 | 3/2009 | Siena et al. |
| 2009/0081674 A1 | 3/2009 | Li et al. |
| 2009/0105081 A1 | 4/2009 | Rodesch et al. |
| 2009/0117573 A1 | 5/2009 | Fu et al. |
| 2009/0117621 A1 | 5/2009 | Boutell et al. |
| 2009/0124514 A1 | 5/2009 | Fu et al. |
| 2009/0138286 A1 | 5/2009 | Linder et al. |
| 2009/0181861 A1 | 7/2009 | Li et al. |
| 2009/0186065 A1 | 7/2009 | Tillman et al. |
| 2009/0202984 A1 | 8/2009 | Cantor |
| 2009/0202989 A1 | 8/2009 | Hillan |
| 2009/0226925 A1 | 9/2009 | Grebe et al. |
| 2009/0226975 A1 | 9/2009 | Sabot et al. |
| 2009/0247415 A1 | 10/2009 | Van |
| 2009/0258795 A1 | 10/2009 | Cowens et al. |
| 2009/0264298 A1 | 10/2009 | Lim et al. |
| 2009/0269344 A1 | 10/2009 | Siena et al. |
| 2009/0299645 A1 | 12/2009 | Colby et al. |
| 2010/0004253 A1 | 1/2010 | Aziz et al. |
| 2010/0029498 A1 | 2/2010 | Gnirke et al. |
| 2010/0041048 A1 | 2/2010 | Diehl et al. |
| 2010/0069250 A1 | 3/2010 | White, III et al. |
| 2010/0074895 A1 | 3/2010 | Petricoin, III et al. |
| 2010/0093550 A1 | 4/2010 | Stuelpnagel et al. |
| 2010/0129799 A1 | 5/2010 | Guomundsson et al. |
| 2010/0129896 A1 | 5/2010 | Knapp et al. |
| 2010/0130527 A1 | 5/2010 | Lehrer et al. |
| 2010/0137143 A1 | 6/2010 | Rothberg et al. |
| 2010/0143932 A1 | 6/2010 | Lapidus |
| 2010/0143935 A1 | 6/2010 | Davis |
| 2010/0166747 A1 | 7/2010 | Beltran et al. |
| 2010/0167954 A1 | 7/2010 | Earnshaw et al. |
| 2010/0173294 A1 | 7/2010 | Langland et al. |
| 2010/0184099 A1 | 7/2010 | Pestano et al. |
| 2010/0184618 A1 | 7/2010 | Namsaraev et al. |
| 2010/0196889 A1 | 8/2010 | Bankaitis-Davis et al. |
| 2010/0196898 A1 | 8/2010 | Sugarbaker et al. |
| 2010/0216153 A1 | 8/2010 | Lapidus et al. |
| 2010/0255004 A1 | 10/2010 | Depinho et al. |
| 2010/0286143 A1 | 11/2010 | Dias-Santagata et al. |
| 2010/0297615 A1 | 11/2010 | Seshagiri |
| 2010/0304446 A1 | 12/2010 | Davies et al. |
| 2010/0304989 A1 | 12/2010 | Von Hoff et al. |
| 2011/0004413 A1 | 1/2011 | Carnevali et al. |
| 2011/0053157 A1 | 3/2011 | Skog et al. |
| 2011/0091880 A1 | 4/2011 | Rafnar et al. |
| 2011/0157322 A1 | 6/2011 | Bennett et al. |
| 2011/0159499 A1 | 6/2011 | Hindson et al. |
| 2011/0212456 A1 | 9/2011 | Siena et al. |
| 2011/0212991 A1 | 9/2011 | Langland et al. |
| 2011/0217710 A9 | 9/2011 | Shapero |
| 2011/0230360 A1 | 9/2011 | Stephan et al. |
| 2011/0244455 A1 | 10/2011 | Larson et al. |
| 2011/0275097 A9 | 11/2011 | Singh et al. |
| 2011/0299645 A1 | 12/2011 | Kim et al. |
| 2012/0003657 A1 | 1/2012 | Myllykangas et al. |
| 2012/0028814 A1 | 2/2012 | Toloue et al. |
| 2012/0115143 A1 | 5/2012 | Livak et al. |
| 2012/0156728 A1 | 6/2012 | Li et al. |
| 2012/0157322 A1 | 6/2012 | Myllykangas et al. |
| 2012/0208706 A1 | 8/2012 | Downing et al. |
| 2012/0264129 A1 | 10/2012 | Freeman et al. |
| 2013/0045872 A1 | 2/2013 | Zhou et al. |
| 2013/0143276 A1 | 6/2013 | Zhelkovsky et al. |
| 2013/0231253 A1 | 9/2013 | Amorese et al. |
| 2014/0080733 A1 | 3/2014 | Stephan et al. |
| 2014/0141426 A1 | 5/2014 | Stephan et al. |
| 2014/0141980 A1 | 5/2014 | Stephan et al. |
| 2014/0172319 A1 | 6/2014 | Von Hoff et al. |
| 2014/0193860 A1 | 7/2014 | Bevilacqua et al. |
| 2014/0287937 A1 | 9/2014 | So et al. |
| 2014/0303008 A1 | 10/2014 | Schutz et al. |
| 2015/0017635 A1 | 1/2015 | Myllykangas et al. |
| 2015/0031086 A1 | 1/2015 | Heller et al. |
| 2015/0126377 A1 | 5/2015 | Gnirke et al. |
| 2015/0284714 A1 | 10/2015 | Gormley et al. |
| 2016/0115553 A1 | 4/2016 | Stephan et al. |
| 2016/0115554 A1 | 4/2016 | Stephan et al. |
| 2016/0122830 A1 | 5/2016 | Stephan et al. |
| 2016/0186267 A1 | 6/2016 | So et al. |
| 2016/0222427 A1 | 8/2016 | So et al. |
| 2016/0281154 A1 | 9/2016 | So et al. |
| 2016/0362749 A1 | 12/2016 | Stephan et al. |
| 2017/0101674 A1 | 4/2017 | So et al. |
| 2018/0148756 A1 | 5/2018 | So et al. |
| 2019/0271044 A1 | 9/2019 | Stephan et al. |
| 2023/0357864 A1 | 11/2023 | Stephan et al. |

FOREIGN PATENT DOCUMENTS

| | | |
|---|---|---|
| EP | 1394272 B1 | 3/2006 |
| EP | 1546313 B1 | 4/2008 |
| EP | 1995330 A1 | 11/2008 |
| EP | 1573316 B1 | 8/2009 |
| EP | 0972024 B1 | 2/2011 |
| EP | 2318552 A2 | 5/2011 |
| EP | 1591541 B1 | 2/2012 |
| EP | 2481815 A1 | 8/2012 |
| EP | 2396430 B1 | 5/2013 |
| EP | 2610352 B1 | 10/2014 |
| EP | 2376659 B1 | 12/2015 |
| JP | 2002503954 A | 2/2002 |
| JP | 2003501071 A | 1/2003 |
| JP | 2010041985 A | 2/2010 |
| WO | WO-9015065 A1 | 12/1990 |
| WO | WO-9322456 A1 | 11/1993 |
| WO | WO-9914226 A2 | 3/1999 |
| WO | WO-0175160 A1 | 10/2001 |
| WO | WO-2004062483 A2 | 7/2004 |
| WO | WO-2004111603 A2 | 12/2004 |
| WO | WO-2005049849 A2 | 6/2005 |
| WO | WO-2004111603 A3 | 7/2005 |
| WO | WO-2005085473 A2 | 9/2005 |
| WO | WO-2005094357 A2 | 10/2005 |
| WO | WO-2005108583 A1 | 11/2005 |
| WO | WO-2006012361 A2 | 2/2006 |
| WO | WO-2005085473 A3 | 3/2006 |
| WO | WO-2006047787 A2 | 5/2006 |
| WO | WO-2004062483 A3 | 7/2006 |
| WO | WO-2006108627 A1 | 10/2006 |
| WO | WO-2006128463 A2 | 12/2006 |
| WO | WO-2006128463 A3 | 2/2007 |
| WO | WO-2007038792 A2 | 4/2007 |
| WO | WO-2007050465 A2 | 5/2007 |
| WO | WO-2007091228 A1 | 8/2007 |
| WO | WO-2007091230 A1 | 8/2007 |
| WO | WO-2007100243 A1 | 9/2007 |
| WO | WO-2007106432 A2 | 9/2007 |
| WO | WO-2007050465 A3 | 10/2007 |
| WO | WO-2007038792 A3 | 11/2007 |
| WO | WO-2008038259 A1 | 4/2008 |
| WO | WO-2008076406 A2 | 6/2008 |

(56) References Cited

FOREIGN PATENT DOCUMENTS

| WO | WO-2005094357 A3 | 12/2008 |
|---|---|---|
| WO | WO-2008147879 A1 | 12/2008 |
| WO | WO-2008157220 A1 | 12/2008 |
| WO | WO-2009004335 A1 | 1/2009 |
| WO | WO-2009038853 A2 | 3/2009 |
| WO | WO-2009046445 A1 | 4/2009 |
| WO | WO-2009102957 A2 | 8/2009 |
| WO | WO-2009108637 A1 | 9/2009 |
| WO | WO-2009114836 A1 | 9/2009 |
| WO | WO-2010028288 A2 | 3/2010 |
| WO | WO-2010036352 A1 | 4/2010 |
| WO | WO-2010045318 A2 | 4/2010 |
| WO | WO-2010045318 A3 | 8/2010 |
| WO | WO-2010094040 A1 | 8/2010 |
| WO | WO-2011025477 A1 | 3/2011 |
| WO | WO-2011106314 A2 | 9/2011 |
| WO | WO-2011140510 A2 | 11/2011 |
| WO | WO-2012018638 A2 | 2/2012 |
| WO | WO-2012103154 A1 | 8/2012 |
| WO | WO-2012142213 A2 | 10/2012 |
| WO | WO-2013036810 A1 | 3/2013 |
| WO | WO-2013066641 A1 | 5/2013 |
| WO | WO-2013112923 A1 | 8/2013 |
| WO | WO-2013113012 A2 | 8/2013 |
| WO | WO-2013119690 A1 | 8/2013 |
| WO | WO-2013173472 A1 | 11/2013 |
| WO | WO-2013190441 A2 | 12/2013 |
| WO | WO-2014130890 A1 | 8/2014 |
| WO | WO-2015089333 A1 | 6/2015 |
| WO | WO-2017139492 A1 | 8/2017 |

OTHER PUBLICATIONS

Krypuy et al., "High resolution melting analysis for the rapid and sensitive detection of mutations in clinical samples: KRAS codon 12 and 13 mutations in non-small cell lung cancer" 6 BMC Cancer 295 1-12 (Year: 2006).*
Samowitz et al. "Poor Survival Associated with the BRAF V600E Mutation in Microsatellite-Stable Colon Cancers" 65(14) Cancer Research 6063-6070 (Year: 2006).*
Gryfe et al., "Tumor Microsatellite Instability and Clinical Outcome In Young Patients With Colorectal Cancer" 342(2) The New England Journal of Medicine 69-77 (Year: 2000).*
Hirsch et al., "Combination of EGFR gene copy number and protein expression predicts outcome for advanced non-small-cell lung cancer patients treated with gefitinib" 18 Annals of Oncology 752-760 (Year: 2007).*
Co-pending U.S. Appl. No. 18/356,900, inventors Stephan; Dietrich et al., filed on Jul. 21, 2023.
Lips et al., "Reliable High-Throughput Genotyping and Loss-of-Heterozygosity Detection inf Formalin-Fixed, Paraffin-Embedded Tumors Using single Nucleotide Polyorphism Arrays" Cancer Research, 65(22): 2005; 10188-10891.
U.S. Appl. No. 15/183,655 Office Action dated Apr. 6, 2018.
U.S. Appl. No. 16/154,307 Office Action dated Feb. 24, 2023.
U.S. Appl. No. 16/154,307 Office Action dated Jul. 20, 2022.
Agrawal, et al. Tetrahedron Letters. 1990; vol. 31: 1543-1546.
Alazzouzi, et al. SMAD4 as a prognostic marker in colorectal cancer. Clin Cancer Res. Apr. 1, 2005;11(7):2606-11.
Albert, et al. Direct selection of human genomic loci by microarray hybridization. Nature Methods (2007), 4 (11):903-5.
Alizadeh, et al. Distinct types of diffuse large B-cell lymphoma identified by gene expression profiling. Nature. Feb. 3, 2000;403(6769):503-11.
Altschul, et al. Basic local alignment search tool. Journal of molecular biology. 1990; vol. 215. No. 3: 403-410.
Anker, et al. K-ras mutations are found in DNA extracted from the plasma of patients with colorectal cancer. Gastroenterology. Apr. 1997;112(4):1114-20.

Applied Biosystems: Designing TaqMan® MGB Probe and Primer Sets for Allelic Discrimination Assays Using Primer Express® Software Version 2.0 (2002).
Arber, et al. Celecoxib for the prevention of colorectal adenomatous polyps. N Engl J Med. Aug. 31, 2006;355(9):885-95.
Aureon Laboratories. Available at http://www.aureon.com. Accessed Feb. 5, 2009.
Bashiardes, et al. Direct genomic selection. Nat Methods. Jan. 2005;2(1):63-9.
Bazan, et al. Specific codon 13 K-ras mutations are predictive of clinical outcome in colorectal cancer patients, whereas codon 12 K-ras mutations are associated with mucinous histotype. Ann Oncol. Sep. 2002;13(9):1438-46.
Beaucage, et al. Tetrahedron Lett. 1981; vol. 22: 1859-1862.
Beck; et al., Profile of the circulating DNA in apparently healthy individuals. Clin Chem. Apr. 2009;55(4):730-8. doi: 10.1373/clinchem.2008.113597. Epub Jan. 30, 2009.
Belloch, et al. Detection of BRAF V600E mutation in colorectal cancer: comparison of automatic sequencing and real-time chemistry methodology. J Mol Diagn. Nov. 2006;8(5):540-3.
Bentley, et al. Accurate whole human genome sequencing using reversible terminator chemistry. Nature. Nov. 6, 2008;456(7218):53-9. doi: 10.1038/nature07517.
Bertagnolli, et al. Celecoxib for the prevention of sporadic colorectal adenomas. N Engl J Med. Aug. 31, 2006;355(9):873-84.
Bishop; E., Indicators, vol. 1. Pergamon Press, Oxford, 1972.
Blondal et al. Isolation and characterization of a thermostable RNA ligase 1 from a Thermus scotoductus bacteriophage TS2126 with good single-stranded DNA ligation properties. Nucleic Acid Research 33(1):135-142 (2005).
Braun, et al. Predictive biomarkers of chemotherapy efficacy in colorectal cancer: results from the UK MRC FOCUS trial. Journal of clinical oncology. Jun. 1, 2008; 26(16):2690-2698.
Brenner, et al. In vitro cloning of complex mixtures of DNA on microbeads: physical separation of differentially expressed cDNAs. Proc Natl Acad Sci U S A. Feb. 15, 2000;97(4):1665-70.
Brown et al. Chemical synthesis and cloning of a tyrosine tRNA gene. Methods Enzymol. 68:109-51 (1979).
Bunzli. Luminescent lanthanide probes as diagnostic and therapeutic tools. Metal Ions in Biological Systems. 2004; 42 ch2:39-75.
Campbell, et al. Identification of somatically acquired rearrangements in cancer using genome-wide massively parallel paired-end sequencing. Nat Genet. Jun. 2008;40(6):722-9. Epub Apr. 27, 2008.
Cancer Genome Atlas Research Network. Comprehensive genomic characterization defines human glioblastoma genes and core pathways. Nature. Oct. 23, 2008;455(7216):1061-8. Epub Sep. 4, 2008.
Cappuzzo, et al. EGFR FISH assay predicts for response to cetuximab in chemotherapy refractory colorectal cancer patients. Ann Oncol. Apr. 2008;19(4):717-23. Epub Oct. 31, 2007.
Cappuzzo, et al. Primary resistance to cetuximab therapy in EGFR FISH-positive colorectal cancer patients. Br J Cancer. Jul. 8, 2008;99(1):83-9. Epub Jun. 24, 2008.
Carbone. Biomarkers of response to gefitinib in non-small-cell lung cancer. Nat Clin Pract Oncol. Dec. 2004;1(2):66-7.
Carethers, J. M. Systemic treatment of advanced colorectal cancer: Tailoring therapy to the tumor. Therapeutic Advances in Gastroenterology. 2008; 1(1):33-42.
Caris Diagnostics Press Release. Caris Diagnostics Providing KRAS Mutational Analysis for Colon Cancer Patients. Dated Jun. 24, 2008. Available at http://www.redorbit.com/news/health/1447721/caris_diagnostics_providing_kras_mutational_analysis_for_colon_cancer_patients/index.html. Accessed May 23, 2011.
Caris life sciences. Website and information. http://web.archive.org/web/20080705021726/http://www.carisdx.com/pages/diagServ/giPath.html. Crawl date Jul. 5, 2008. Accessed Aug. 28, 2012.
Carlini, et al. UGT1A7 and UGT1A9 Polymorphisms Predict Response and Toxicity in Colorectal Cancer Patients Treated with Capecitabine/Irinotecan. Clin Cancer Res., Feb. 1, 2005, 11;1226.
Cascinu, et al. Vascular endothelial growth factor expression, S-phase fraction and thymidylate synthase quantitation in node-positive colon cancer: relationships with tumor recurrence and resistance to adjuvant chemotherapy. Ann Oncol. Feb. 2001;12(2):239-44.

(56) References Cited

OTHER PUBLICATIONS

Chabert, et al. Automated microdroplet platform for sample manipulation and polymerase chain reaction. Anal Chem. Nov. 15, 2006; 78(22): 7722-8.
Chang, et al. Estimating the cost of cancer: results on the basis of claims data analyses for cancer patients diagnosed with seven types of cancer during 1999 to 2000. J Clin Oncol. Sep. 1, 2004;22(17):3524-30.
Chen; et al., Microsatellite alterations in plasma DNA of small cell lung cancer patients. Nat Med. Sep. 1996;2(9):1033-5.
Chen, et al. Electrokinetically synchronized polymerase chain reaction microchip fabricated in polycarbonate. Anal Chem. Jan. 15, 2005; 77(2): 658-66.
Chen, et al. Mapping translocation breakpoints by next-generation sequencing. Genome Res. Jul. 2008;18(7):1143-9. Epub Mar. 7, 2008.
Cheng, et al. Performing microchannel temperature cycling reactions using reciprocating reagent shuttling along a radial temperature gradient. Analyst. Jun. 2005; 130(6): 931-40. Epub Apr. 22, 2005.
Chinese Office Action dated Dec. 15, 2017 for Chinese Patent Application No. CN201400228181. 3 pages.
Chiu; et al., Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63. doi: 10.1073/pnas.0810641105. Epub Dec. 10, 2008.
Chiuman, et al. Mapping AppDNA using T4 DNA ligase. Bioorganic Chemistry. 2002; 30:332-349.
Choi, et al. Genetic diagnosis by whole exome capture and massively parallel DNA sequencing. PNAS, vol. 106, No. 45, Sep. 2009, pp. 19096-19101.
Chong, et al. Detection of activated K-ras in non-small cell lung cancer by membrane array: a comparison with direct sequencing. Oncol Rep. Jul. 2007;18(1):17-24.
Ciaparrone, et al. Predictive role of thymidylate synthase, dihydropyrimidine dehydrogenase and thymidine phosphorylase expression in colorectal cancer patients receiving adjuvant 5-fluorouracil. Oncology. 2006;70(5):366-77. Epub Dec. 15, 2006.
Combimatrix. Available at http://www.combimatrix.com. Accessed Feb. 5, 2009.
Cote, et al. UGT1A1 polymorphism can predict hematologic toxicity in patients treated with irinotecan. Clin Cancer Res. Jun. 1, 2007;13(11):3269-75.
Dahl, et al. Multigene amplification and massively parallel sequencing for cancer mutation discovery. PNAS (2007), 104(22):9387-9392.
Dai, et al. Efficient Chemical Synthesis of AppDNA by Adenylation of Immobilized DNA-5'- monophosphate. Org. Lett., 2009, 11 (5), pp. 1067-1070.
Deininger et al. Prevalence of T315I, Dasatinib-Specific Resistant Mutations (F317L, V299L, and T315A), and Nilotinib-Specific Resistant Mutations (P-loop and F359) at the Time of Imatinib Resistance in Chronic-Phase Chronic Myeloid Leukemia (CP-CML). Blood, 2008, 112:3236.
Diehl, et al. Analysis of mutations in DNA isolated from plasma and stool of colorectal cancer patients. Gastroenterology. Aug. 2008;135(2):489-98. doi: 10.1053/j.gastro.2008.05.039. Epub May 15, 2008.
Diehl et al. Circulating mutant DNA to assess tumor dynamics. Nat Med 14(9):985-990 (2008).
Diehl, et al. Detection and quantification of mutations in the plasma of patients with colorectal tumors. Proc Natl Acad Sci U S A. Nov. 8, 2005;102(45):16368-73. Epub Oct. 28, 2005.
Dorfman, et al. Contamination-free continuous flow microfluidic polymerase chain reaction for quantitative and clinical applications. Anal Chem. Jun. 1, 2005; 77(11): 3700-4.
Draznin, et al. Cancers of the bowel and hepatobiliary tract. Updated On Cancer Therapeutics I. 2006;1(3):353-365.

Dressman, et al. Gene expression profiles of multiple breast cancer phenotypes and response to neoadjuvant chemotherapy. Clin Cancer Res. Feb. 1, 2006;12(3 Pt 1):819-26.
Druker, et al. Efficacy and safety of a specific inhibitor of the BCR-ABL tyrosine kinase in chronic myeloid leukemia. N Engl J Med. Apr. 5, 2001;344(14):1031-7.
Dunbar. Applications of luminex® xMAP™ technology for rapid, high-throughput multiplexed nucleic acid detection. Clinica Chimica Acta. 363 (2006): 71-82.
Edler, et al. Thymidylate synthase expression in colorectal cancer: a prognostic and predictive marker of benefit from adjuvant fluorouracil-based chemotherapy. J Clin Oncol. Apr. 1, 2002;20(7):1721-8.
Elaine R. Mardis. The impact of next-generation sequencing technology on genetics, Trends In Genetics, vol. 24, No. 3, Feb. 11, 2008, pp. 133-141, XP022498431.
Ellis, et al. Bevacizumab beyond progression: does this make sense? J Clin Oncol. Nov. 20, 2008;26(33):5313-5. Epub Oct. 14, 2008.
Erikson, et al. Future supply and demand for oncologists : challenges to assuring access to oncology services. J Oncol Pract. Mar. 2007;3(2):79-86.
European search report and opinion dated Jan. 31, 2014 for EP Application No. 11827484.
European search report and opinion dated Sep. 14, 2016 for EP Application No. 14754263.
European search report and opinion dated Jan. 2, 2012 for EP Application No. 09812316.9.
Extended European Search Report and Search Opinion dated Aug. 14, 2017 for European Patent Application No. EP16198444.8.
F. Eckstein (Ed.). Oligonucleotides and Analogues A Practical Approach. IRL Press, Oxford. 1991: pp. 1-24.
FDA. Genomics and personalized medicine. Available at http://www.fda.gov/fdac/features/2005/605_genomics.html. Accessed Feb. 5, 2009.
Fleischhacker, et al. Circulating nucleic acids (CNAs) and cancer—a survey. Biochim Biophys Acta. Jan. 2007;1775(1):181-232. doi: 10.1016/j.bbcan.2006.10.001. Epub Oct. 7, 2006.
Foreign Office Action dated Aug. 8, 2017 for European Patent Application No. EP11827484.4.
Frattini, et al. PTEN loss of expression predicts cetuximab efficacy in metastatic colorectal cancer patients. Br J Cancer. Oct. 22, 2007;97(8):1139-45. Epub Oct. 16, 2007.
Fredriksson, et al. Multiplex amplification of all coding sequences within 10 cancer genes by Gene-Collector. Nucleic Acids Res. 2007;35(7):e47. Epub Feb. 22, 2007.
Fuss; et al., Isolation of Whole Mononuclear Cells from Peripheral Blood and Cord Blood. Current Protocols in Immunology, 2009. 85:I:7.1:7.1.1-7.1.8.
Gadi, et al. Soluble donor DNA concentrations in recipient serum correlate with pancreas-kidney rejection. Clin Chem. Mar. 2006;52(3):379-82. Epub Jan. 5, 2006.
Gagnon, et al. Irinotecan inactivation is modulated by epigenetic silencing of UGT1A1 in colon cancer. Clin Cancer Res. Mar. 15, 2006;12(6):1850-8.
Gait; M.J., Oligonucleotide Synthesis: A Practical Approach. Oxford (1984).
Genomic Health. Available at http://www.genomichealth.com. Accessed Feb. 5, 2009.
Genoptix Medical Laborator. Webpage. Available at http://www.genoptix.com/genoptixAdvantage.html. Accessed Jun. 8, 2009.
Giusti et al. Synthesis and characterization of 5'-fluorescent-dye-labeled oligonucleotides. PCR Methods Appl. 2(3):223-227 (1993).
Gleevec. Available at http://www.gleevec.com/info/gist/index.jsp. Accessed Feb. 5, 2009.
Gnirke, et al. Solution Hybrid Selection with Ultra-long Oligonucleotides for Massively Parallel Targeted Sequencing. Nat. Biotechnol. (Feb. 1, 2009), 27(2):182-9.
Goemans, et al. Mutations in KIT and RAS are frequent events in pediatric core-binding factor acute myeloid leukemia. Leukemia. Sep. 2005;19(9):1536-42.
Grothey, et al. The Role of Biomarkers in Targeted Therapy for Colorectal Cancer. Medscape General Surgery. American Society of Clinical Oncology (ASCO) conference. 2008. http://www.medscape.org/viewarticle/577606. Accessed Aug. 28, 2012.

(56) References Cited

OTHER PUBLICATIONS

Growney et al. Activation mutations of human c-KIT resistant to imatinib mesylate are sensitive to the tyrosine kinase inhibitor PKC412. Blood. Jul. 15, 2005;106(2):721-4.
Gupta, et a. A general method for the synthesis of 3'-sulfhydryl and phosphate group containing oligonucleotides. Nucleic Acids Res. Jun. 11, 1991; 19(11): 3019-25.
Hafner, et al. Identification of microRNAs and other small regulatory RNAs using cDNA library sequencing. Methods. Jan. 2008;44(1):3-12.
Hames; et al., Nucleic Acid Hybridization: A Practical Approach. IRL Press, Oxford (1985).
Hanawa, et al. EGFR protein overexpression and gene amplification in squamous cell carcinomas of the esophagus. Int J Cancer. Mar. 1, 2006;118(5):1173-80.
Harris, et al. American society of clinical oncology 2007 update of recommendations for the use of tumor markers in breast cancer. J Clin Oncol. Nov. 20, 2007;25(33):5287-312. Epub Oct. 22, 2007.
Harris, et al. Single-molecule DNA sequencing of a viral genome. Science. Apr. 4, 2008;320(5872):106-9.
Harrison, et al. Polymer-stimulated ligation: enhanced ligation of oligo- and polynucleotides by T4 RNA ligase in polymer solutions. Nucleic Acids Res. Nov. 12, 1984;12(21):8235-51.
Haugland; et al., Handbook of Fluorescent Probes and Research Chemicals, 1992-1994. Molecular Probes, 1992.
Hegi, et al. MGMT gene silencing and benefit from temozolomide in glioblastoma. N Engl J Med. Mar. 10, 2005;352(10):997-1003.
Heinrich, et al. Kinase mutations and imatinib response in patients with metastatic gastrointestinal stromal tumor. Journal of Clinical Oncology. Dec. 11, 2003; 21(23):4342-4349.
Higgins, et al. Addition of oligonucleotides to the 5'-terminus of DNA by T4 RNA ligase. Nucleic Acids Res. Mar. 1979;6(3):1013-24.
Ho, et al. Bacteriophage T4 RNA ligase 2 (gp24.1) exemplifies a family of RNA ligases found in all phylogenetic domains. Proc. Natl. Acad. Sci. USA. Oct. 2002; 99(20), 12709-12714.
Ho, et al. Structure and Mechanism of RNA Ligase. Structure, vol. 12, Issue 2, Feb. 2004, pp. 327-339.
Hodges et al. Genome-wide in situ exon capture for selective resequencing. Nature Genetics (2007), 39:1522-7.
Holt et al. The new paradigm of flow cell sequencing. Genome Res. Jun. 2008;18(6):839-46.
Hoshida, et al. Gene Expression in Fixed Tissues and Outcome in Hepatocellular Carcinoma. N Engl J Med. Nov. 6, 2008;359(19):1995-2004. Epub Oct. 15, 2008.
Huang, et al. Codon 249 mutation in exon 7 of p53 gene in plasma DNA: maybe a new early diagnostic marker of hepatocellular carcinoma in Qidong risk area, China. World J Gastroenterol. Apr. 2003;9(4):692-5.
Huber et al. High-resolution liquid chromatography of DNA fragments on non-porous poly(styrene-divinylbenzene) particles. Nucleic Acids Res. Mar. 11, 1993;21(5):1061-6.
Ikediobi, et al. Mutation analysis of 24 known cancer genes in the NCI-60 cell line set. Mol Cancer Ther. Nov. 2006;5(11):2606-12. Epub Nov. 6, 2006.
Illumina. Infinium® DNA Analysis BeadChips. Illumina DNA Analysis. 2007. 4 pages. URL: <https://cancergenome.nih.gov/abouttcga/aboutdata/platformdesign/illuminahumanhap550chip>.
Ingenuity Systems. Available at http://www.ingenuity.com/products/prod_overview.html. Accessed Feb. 5, 2009.
International Preliminary Report on Patentability dated Mar. 8, 2011 for PCT Application No. US2009/56101.
International Preliminary Report on Patentability dated Sep. 3, 2015 for PCT Application No. US2014/017832.
International search report and written opinion dated Jul. 30, 2014 for PCT Application No. US2014/017832.
International search report dated May 7, 2010 for PCT Application No. US2009/56101.
Iqbal, et al. Determinants of prognosis and response to therapy in colorectal cancer. Current Oncology Reports. 2001; 3:102-108.

Japanese Office Action dated Jun. 1, 2017 for Japanese Patent Application No. JP2015-559024. 22 pages.
Jen, et al. Allelic loss of chromosome 18q and prognosis in colorectal cancer. N Engl J Med. Jul. 28, 1994;331(4):213-21.
Jia, et al. A Rotary Polydimethylsiloxane-Based Device for Polymerase Chain Reaction. Analytical Letters. 2005; 38.13: 2143-2149. DOI:10.1080/00032710500260787.
Kantarjian, et al. Hematologic and cytogenetic responses to imatinib mesylate in chronic myelogenous leukemia. N Engl J Med. Feb. 28, 2002;346(9):645-52.
Karapetis, et al. K-ras mutations and benefit from cetuximab in advanced colorectal cancer. New England Journal of Medicine. Oct. 23, 2008; 359(17):1757-1765.
Kato et al. A new packing for separation of DNA restriction fragments by high performance liquid chromatography. J Biochem. Jan. 1984;95(1):83-6.
Kim, et al. Fabrication and characterization of a PDMS-glass hybrid continuous-flow PCR chip. Biochemical Engineering Journal. Apr. 1, 2006; vol. 29. Issues 1-2: 91-97. DOI: 10.1016/j.bej.2005.02.032.
Kimbi, et al. 249ser p53 mutation in the serum of black southern African patients with hepatocellular carcinoma. J Gastroenterol Hepatol. Aug. 2005;20(8):1185-90.
Kimura, et al. EGFR mutation status in tumour-derived DNA from pleural effusion fluid is a practical basis for predicting the response to gefitinib. Br J Cancer. Nov. 20, 2006;95(10):1390-5. Epub Oct. 24, 2006.
Kinzler, et al. Identification of FAP locus genes from chromosome 5q21. Science. 1991; 253(5020): 61-65.
Kiss, et al. High-throughput quantitative polymerase chain reaction in picoliter droplets. Anal Chem. Dec. 1, 2008; 80(23): 8975-81.
Kopp, et al. Chemical amplification: continuous-flow PCR on a chip. Science. May 15, 1998; 280(5366): 1046-8.
Kopreski, et al. Somatic mutation screening: identification of individuals harboring K-ras mutations with the use of plasma DNA. J Natl Cancer Inst. Jun. 7, 2000;92(11):918-23.
Korshunova; et al., Massively parallel bisulphite pyrosequencing reveals the molecular complexity of breast cancer-associated cytosine-methylation patterns obtained from tissue and serum DNA. Genome Res. Jan. 2008;18(1):19-29. Epub Nov. 21, 2007.
Kuhn, et al. Template-independent ligation of single-stranded DNA by T4 DNA ligase. FEBS J. Dec. 2005;272(23):5991-6000.
Kury, et al. Combinations of cytochrome P450 gene polymorphisms enhancing the risk for sporadic colorectal cancer related to red meat consumption. Cancer Epidemiol Biomarkers Prev. Jul. 2007;16(7):1460-7.
Langmead, et al. Ultrafast and memory-efficient alignment of short DNA sequences to the human genome. Genome Biol. 2009; 10(3): R25. doi: 10.1186/GB-2009-10-3-r25. Epub Mar. 4, 2009.
Lau, et al. An Abundant Class of Tiny RNAs with Probable Regulatory Roles in Caenorhabditis elegans. Science Oct. 26, 2001:vol. 294, Issue 5543, pp. 858-862.
Leamon, et al. High-Throughput, Massively Parallel DNA Sequencing Technology for the Era of Personalized Medicine. Gene Therapy and Regulation. vol. 3, No. 1, Mar. 2007, pp. 15-31.
Lee, et al. Metabolic tumor burden predicts for disease progression and death in lung cancer. Int J Radiat Oncol Biol Phys. Oct. 1, 2007;69(2):328-33.
Ley, et al. DNA sequencing of a cytogenetically normal acute myeloid leukaemia genome. Nature. Nov. 6, 2008;456(7218):66-72.
Li, et al. BEAMing up for detection and quantification of rare sequence variants. Nat Methods. Feb. 2006;3(2):95-7.
Li, et al. Capping DNA with DNA. Biochemistry. Mar. 21, 2000;39(11):3106-14.
Li, et al. Distinct microRNA expression profiles in acute myeloid leukemia with common translocations. Proc Natl Acad Sci U S A. Oct. 7, 2008;105(40):15535-40. Epub Oct. 1, 2008.
Li, et al. Ready detection of donor-specific single-nucleotide polymorphisms in the urine of renal transplant recipients by matrix-assisted laser desorption/ionization time-of-flight mass spectrometry. Clin Chem. Oct. 2005;51(10):1903-4.
Li, et al. Structure-independent and quantitative ligation of single-stranded DNA. Anal Biochem. Feb. 15, 2006;349(2):242-6. Epub Nov. 18, 2005.

(56) References Cited

OTHER PUBLICATIONS

Li, et al. The Sequence Alignment/Map format and SAMtools. Bioinformatics. Aug. 15, 2009; 25(16): 2078-9. doi: 10.1093/bioinformatics/btp352. Epub Jun. 8, 2009.
Lindforss, et al. Persistence of K-ras mutations in plasma after colorectal tumor resection. Anticancer Res. Jan.-Feb. 2005;25(1B):657-61.
Livak, et al. Oligonucleotides with fluorescent dyes at opposite ends provide a quenched probe system useful for detecting PCR product and nucleic acid hybridization. PCR Methods Appl. Jun. 1995; 4(6): 357-62.
Maitland, et al. TPMT, UGT1A1 and DPYD: genotyping to ensure safer cancer therapy? Trends in Pharmacological Sciences. Aug. 1, 2006; 27(8):432-437.
Makino, et al. Efficacy of laser capture microdissection plus RT-PCR technique in analyzing gene expression levels in human gastric cancer and colon cancer. BMC Cancer. Jul. 25, 2008;8:210.
Mardis. Next-generation DNA sequencing methods. Annu Rev Genomics Hum Genet. 2008;9:387-402.
Margulies, et al. Genome sequencing in microfabricated high-density picolitre reactors. Nature. Sep. 15, 2005; 437(7057): 376-80. Epub Jul. 31, 2005.
Marone, et al. (1998) Analysis of Cyclin E and CDK2 in Ovarian Cancer: Gene Amplification and RNA Overexpression. International Journal of Cancer, 75:34-39.
Medeiros, et al. Tissue handling for genome-wide expression analysis: a review of the issues, evidence, and opportunities. Arch Pathol Lab Med. Dec. 2007;131(12):1805-16.
Miki, et al. Disruption of the APC gene by a retrotransposal insertion of L1 sequence in a colon cancer. Cancer Res. 1992; 52(3): 643-645.
Mitchell, et al. Circulating microRNAs as stable blood-based markers for cancer detection. PNAS, vol. 105, No. 30, May 2008, pp. 10513-10518.
Mitchell, et al. Inter-platform comparability of microarrays in acute lymphoblastic leukemia. BMC Genomics. Sep. 23, 2004;5:71.
Mitsiades, et al. Targeting BRAFV600E in thyroid carcinoma: therapeutic implications. Mol Cancer Ther. Mar. 2007;6(3):1070-8.
Munchow, et al. Automated chip-based device for simple and fast nucleic acid amplification. Expert Rev Mol Diagn. Jul. 2005; 5(4): 613-20.
Nadauld et al. Implementation of a precision cancer program in an integrated health care system. Journal of Clinical Oncology, 2015 ASCO Annual Meeting (May 29-Jun. 2, 2015). vol. 33, No. 15_suppl (May 20 supplement), Abstract No. e17647. (2015).
Nadauld et al. Precision medicine to improve survival without increasing costs in advanced cancer patients. Journal of Clinical Oncology, 2015 ASCO Annual Meeting (May 29-Jun. 2, 2015). vol. 33, No. 15_suppl (May 20 supplement), Abstract No. e17641. (2015).
Nagase, et al. Screening for germ-line mutations in familial adenomatous polyposis patients: 61 new patients and a summary of 150 unrelated patients. Hum. Mutat. 1992; 1(6): 467-473.
Nagrath, et al. Isolation of rare circulating tumour cells in cancer patients by microchip technology. Nature. Dec. 20, 2007;450(7173):1235-9.
Nakano, et al. Evaluations of biomarkers associated with 5-FU sensitivity for non-small-cell lung cancer patients postoperatively treated with UFT. Br J Cancer. Sep. 4, 2006;95(5):607-15. Epub Aug. 1, 2006.
Nakatsuru, et al. Somatic mutation of the APC gene in gastric cancer: frequent mutations in very well differentiated adenocarcinoma and signet-ring cell carcinoma. Hum. Mol. Genet. Nov. 1992; 1(8): 559-563.
Nandakumar, et al. RNA Substrate Specificity and Structure-guided Mutational Analysis of Bacteriophage T4 Rna Ligase 2 *. Jul. 23, 2004. The Journal of Biological Chemistry, 279, 31337-31347 ..
Narang, et al. Improved phosphotriester method for the synthesis of gene fragments. Methods Enzymol. 1979;68:90-8.

National Comprehensive Cancer Network. Available at http://www.nccn.org/Registration/login/login.aspx?s=PG. Accessed Feb. 5, 2009.
Nawroz; et al., Microsatellite alterations in serum DNA of head and neck cancer patients. Nat Med. Sep. 1996;2(9):1035-7.
NCCN. Clinical Practice Guidelines in Oncology Colon Cancer. NCCN Clinical Practice Guidelines in Oncology Colon Cancer V.1.2008. Sep. 19, 2007. National Comprehensive Cancer Network. 60 pages.
NCCN Clinical Practice Guidelines in Oncology. Colon Cancer. V.2.2008. National Comprehensive Cancer Network. Jun. 30, 2008, and Jul. 2, 2008. Available at http://www.pacificcancer.org/cancer-information/cancer-downloads/colorectal/NCCN_Guidelines_colon.pdf. Accessed Nov. 27, 2012.
NCCN clinical practice guidelines in oncology. Colon Cancer. V.2.2008 (V.1.2008 available). National Comprehensive Cancer Network. Available at http://www.nccn.org/professionals/physician_gls/pdf/colon.pdf. Accessed Jun. 8, 2008.
NCI. The Promise of Prevention and Early Diagnosis. Section III. The Nation's Investment in Cancer Research. National Cancer Institute. Available at http://plan.cancer.gov/The_Promise_of_Prevention_and_Early_Diagnosis.htm. Accessed Jun. 5, 2008.
NCI. The Promise of Prevention and Early Diagnosis. Section III. The Nation's Investment in Cancer Research. National Cancer Institute. Available at http://web.archive.org/web/20080518073705/http://plan.cancer.gov/The_Promise_of_Prevention_and_Early_Diagnosis.htm. Crawl date May 18, 2008. Accessed Nov. 27, 2012.
Nelson, et al. Bifunctional oligonucleotide probes synthesized using a novel CPG support are able to detect single base pair mutations. Nucleic Acids Res. Sep. 25, 1989; 17(18): 7187-94.
Newton, et al. Analysis of any point mutation in DNA. The amplification refractory mutation system (ARMS). Nucleic Acids Res. Apr. 11, 1989;17(7):2503-16.
Ng; et al, Targeted capture and massively parallel sequencing of 12 human exomes. Nature 461, 272-276 (Sep. 10, 2009).
Nicolantonio, et al. Wild-type BRAF is required for response to panitumumab or cetuximab in metastatic colorectal cancer. Journal of Clinical Oncology. Dec. 10, 2008; 26(35):5705-5712.
Nishisho, et al. Mutations of chromosome 5q21 genes in FAP and colorectal cancer patients. Science. Aug. 1991; 253(5020): 65-69.
Notice of allowance dated Feb. 24, 2016 for U.S. Appl. No. 13/239,226.
Notice of allowance dated Jul. 24, 2013 for U.S. Appl. No. 13/060,425. 10 pages.
Notice of Opposition dated Sep. 29, 2017 for European Patent Application No. EP09812316.9. 28 pages.
O'Brien, et al. Phase III trial comparing supportive care alone with supportive care with oral topotecan in patients with relapsed small-cell lung cancer. J Clin Oncol. Dec. 1, 2006;24(34):5441-7.
O'Dwyer, et al. Uridine diphosphate glucuronosyltransferase (UGT) 1A1 and irinotecan: practical pharmacogenomics arrives in cancer therapy. Journal of Clinical Oncology. Oct. 1, 2006; 24(28):4534-4538.
Office Action dated Jan. 27, 2017 for U.S. Appl. No. 14/075,996.
Office Action dated Feb. 8, 2017 for U.S. Appl. No. 14/927,254.
Office action dated Mar. 13, 2013 for U.S. Appl. No. 13/060,425. 16 pages.
Office action dated Mar. 29, 2016 for U.S. Appl. No. 14/300,048.
Office action dated Apr. 16, 2014 for U.S. Appl. No. 13/239,226.
Office action dated May 8, 2015 for U.S. Appl. No. 14/075,996. 32 pages.
Office action dated May 19, 2016 for U.S. Appl. No. 14/187,041. 31 pages.
Office action dated May 25, 2012 for U.S. Appl. No. 13/060,425. 37 pages.
Office Action dated Jun. 2, 2017 for U.S. Appl. No. 14/769,047.
Office action dated Jun. 4, 2015 for U.S. Appl. No. 13/239,226. 12 pages.
Office Action dated Jun. 14, 2017 for U.S. Appl. No. 14/300,048.
Office action dated Jun. 30, 2016 for U.S. Appl. No. 14/075,996. 29 pages.
Office action dated Jul. 28, 2016 for U.S. Appl. No. 14/927,254. 16 pages.
Office action dated Aug. 12, 2015 for U.S. Appl. No. 14/187,041.

(56) References Cited

OTHER PUBLICATIONS

Office action dated Aug. 22, 2014 for U.S. Appl. No. 14/075,984. 20 pages.
Office action dated Aug. 25, 2014 for U.S. Appl. No. 14/027,102. 29 pages.
Office action dated Sep. 9, 2014 for U.S. Appl. No. 14/075,996. 24 pages.
Office action dated Sep. 23, 2016 for U.S. Appl. No. 14/925,911. 30 pages.
Office action dated Sep. 24, 2014 for U.S. Appl. No. 13/239,226. 9 pages.
Office action dated Sep. 26, 2016 for U.S. Appl. No. 14/925,910. 19 pages.
Office action dated Nov. 25, 2016 for U.S. Appl. No. 14/300,048.
Office action dated Dec. 11, 2015 for U.S. Appl. No. 13/239,226.
Ogino, et al. Sensitive sequencing method for KRAS mutation detection by Pyrosequencing. J Mol Diagn. Aug. 2005;7(3):413-21.
Okou, et al. Microarray-based genomic selection for high through put resequencing. Nature Methods. 2007. 4:907-9.
Out, et al. Deep sequencing to reveal new variants in pooled DNA samples. Hum Mutat. Dec. 2009; 30(12): 1703-12. doi: 10.1002/humu.21122.
Pao et al. KRAS mutations and primary resistance of lung adenocarcinomas to gefitinib or erlotinib. PLoS Med. 2(1):e17 (Jan. 2005).
Parker, et al. Supervised risk predictor of breast cancer based on intrinsic subtypes. J Clin Oncol. Mar. 10, 2009;27(8):1160-7. Epub Feb. 9, 2009.
Pathwork Diagnostics. Available at http://www.pathworkdx.com. Accessed Feb. 5, 2009.
Pearson et al. Improved Tools for Biological Sequence Comparison. PNAS USA 85:2444-48 (1988).
Pfeffer, et al. Unit 26.4 Cloning of Small RNA Molecules. Current protocols in Molecular Biology, Nov. 2005, Chapter 26.
Pierce, et al. Linear-After-The-Exponential (LATE)-PCR: primer design criteria for high yields of specific single-stranded DNA and improved real-time detection. Proc Natl Acad Sci U S A. Jun. 14, 2005;102(24):8609-14. Epub Jun. 3, 2005.
Placido, et al. Modulation of 5-fluorouracil as adjuvant systemic chemotherapy in colorectal cancer: the IGCS-COL multicentre, randomised, phase III study. Br J Cancer. Oct. 17, 2005;93(8):896-904.
P-MARK. Validation of recently developed diagnostic and prognostic markers and identification of novel markers for prostate cancer using European databases. Available at ftp://ftp.cordis.europa.eu/pub/lifescihealth/docs/canpr210_en.pdf. Accessed Feb. 5, 2009.
Porreca, et al., Multiplex amplification of large sets of human exons. Nature Methods. 2007. 4: 931-6.
Powers, E. O. The NCCN guidelines: how do they related to community oncology practice. Available at http://www.communityoncology.net/journal/articles/0102098.pdf. Accessed Feb. 5, 2009.
Punia, et al. The quantitative amplification refractory mutation system. 2009. http://www.horizonpress.com/pcr/pdf/rtpcr/rtpcr09.pdf.
Redaelli et al. Activity of bosutinib, dasatinib, and nilotinib against 18 imatinib-resistant BCR/ABL mutants. J Clin Oncol. Jan. 20, 2009;27(3):469-71.
Response Genetics. Available at http://www.responsegenetics.com. Accessed Feb. 5, 2009.
Ribic, et al. Tumor microsatellite-instability status as a predictor of benefit from fluorouracil-based adjuvant chemotherapy for colon cancer. N Engl J Med. Jul. 17, 2003;349(3):247-57.
Rice, et al. Monoplex/multiplex linear-after-the-exponential-PCR assays combined with PrimeSafe and Dilute-'N'-Go sequencing. Nat Protoc. 2007;2(10):2429-38.
Rosenberg, et al. Comparison of two density gradient centrifugation systems for the enrichment of disseminated tumor cells in blood. Cytometry. Dec. 1, 2002;49(4):150-8.
Ryan, et al. A prospective study of circulating mutant KRAS2 in the serum of patients with colorectal neoplasia: strong prognostic indicator in postoperative follow up. Gut. Jan. 2003;52(1):101-8.
Sakurada, A. et al., Tissue heterogeneity of EGFR mutation in lung adenocarcinoma, Journal of Thoracic Oncology. May 2008; 3(5):527-529.
Sambrook; et al., Molecular Cloning: A Laboratory Manual. Second edition, Cold Spring Harbor Laboratory Press, 1989.
Sanchez, et al. Linear-after-the-exponential (LATE)-PCR: an advanced method of asymmetric PCR and its uses in quantitative real-time analysis. Proc Natl Acad Sci U S A. Feb. 17, 2004;101(7):1933-8. Epub Feb. 9, 2004.
Sartore-Bianchi, et al. PIK3CA mutations in colorectal cancer are associated with clinical resistance to EGFR-targeted monoclonal antibodies. Cancer Res. Mar. 1, 2009;69(5):1851-7. Epub Feb. 17, 2009.
Schmid, et al. Tumor burden index as a prognostic tool for cutaneous T-cell lymphoma: a new concept. Arch Dermatol. Oct. 1999;135(10):1204-8.
Schuster, Stephan C., Next-generation sequencing transforms today's biology, Nature Methods, vol. 5, No. 1, Jan. 1, 2008, pp. 16-18, XP0081006842.
Schuurman, M. Family history of colorectal cancer and the risk of colorectal cancer characterized by distinct molecular markers and phenotypes. Results from the Netherlands cohort study on diet and cancer. Thesis, Maastricht University. Mar.-Jul. 2008.
Schweiger, et al. Genome-wide massively parallel sequencing of formaldehyde fixed-paraffin embedded (FFPE) tumor tissues for copy-number- and mutation-analysis. PLoS One. 2009;4(5):e5548. Epub May 14, 2009.
Shedden, et al. Director's Challenge Consortium for the Molecular Classification of Lung Adenocarcinoma, et al. Gene expression-based survival prediction in lung adenocarcinoma: a multi-site, blinded validation study. Nat Med. Aug. 2008;14(8):822-7. Epub Jul. 20, 2008.
Shendure, et al. Accurate Multiplex Polony Sequencing of an Evolved Bacterial Genome. Science (2005), 309:1728-32.
Shendure, et al. Next-generation DNA sequencing. Nat Biotechnol. Oct. 2008;26(10):1135-45. doi: 10.1038/nbt1486.
Shendure JA, Porreca GJ, Church GM. 2008. Overview of DNA sequencing strategies Curr Protec Mol Biol Chapter 7: Unit 7.1; Supplement 81: 11 Pages.
Shinozaki, et al. Incidence of BRAF oncogene mutation and clinical relevance for primary cutaneous melanomas. Clin Cancer Res. Mar. 1, 2004;10(5):1753-7.
Shinozaki, et al. Utility of circulating B-RAF DNA mutation in serum for monitoring melanoma patients receiving biochemotherapy. Clin Cancer Res. Apr. 1, 2007;13(7):2068-74.
Shoemaker, et al. Quantitative phenotypic analysis of yeast deletion mutants using a highly parallel molecular bar-coding strategy. Nature Genetics, 14: 450-456 (1996).
Sigma. qPCR technical guide. Sigma Aldrich life sciences. 2008.
Simons, et al. Ultra-deep sequencing of EGFR from lung carcinoma patients reveals low abundance drug response mutations. XIV International HIV Drug Resistance Workshop in Quebec City, Canada , (2005).
Solexa. Solexa Genome Analysis System Brochure. Copyright 2006. 2 pages. Available at https://www.fasteris.com/pdf/System_Profile_Brochure_10_05_06.pdf. Accessed Oct. 7, 2016.
Solexa. Application note: DNA sequencing. 2006. Solexa 2 pages.
Soni, et al. Progress toward ultrafast DNA sequencing using solid-state nanopores. Clin Chem. Nov. 2007; 53(11): 1996-2001. Epub Sep. 21, 2007.
Sproat, et al. The synthesis of protected 5'-mercapto-2',5'-dideoxyribonucleoside-3'-O-phosphoramidites; uses of 5'-mercapto-oligodeoxyribonucleotides. Nucleic Acids Res. Jun. 25, 1987; 15(12): 4837-48.
Stroun, et al. Isolation and characterization of DNA from the plasma of cancer patients. Eur J Cancer Clin Oncol. Jun. 1987; 23(6): 707-12.

(56) References Cited

OTHER PUBLICATIONS

Su, et al. Detection of mutated K-ras DNA in urine, plasma, and serum of patients with colorectal carcinoma or adenomatous polyps. Ann N Y Acad Sci. Aug. 2008;1137:197-206. doi: 10.1196/annals.1448.027.
Su, et al. Human urine contains small, 150 to 250 nucleotide-sized, soluble DNA derived from the circulation and may be useful in the detection of colorectal cancer. J Mol Diagn. May 2004;6(2):101-7.
Sugarbaker, et al. Transcriptome sequencing of malignant pleural mesothelioma tumors. Proc Natl Acad Sci U S A. Mar. 4, 2008;105(9):3521-6. doi: 10.1073/pnas.0712399105. Epub Feb. 26, 2008.
Sutent. Available at http://www.sutent.com. Accessed Feb. 5, 2009.
Taldone, et al. Targeting Hsp90: small-molecule inhibitors and their clinical development. Curr Opin Pharmacol. Aug. 2008;8(4):370-4. Epub Jul. 31, 2008.
Tanaka, et al. Chromosome 18q deletion and Smad4 protein inactivation correlate with liver metastasis: A study matched for T- and N-classification. Br J Cancer. Dec. 4, 2006;95(11):1562-7.
Tessier, et al. Ligation of single-stranded oligodeoxyribonucleotides by T4 RNA ligase. Anal Biochem. Oct. 1986;158(1):171-8.
The Translational Genomics Research Institute. Research Overview. Available at http://www.tgen.org/research/index.cfm?pageid=6. Accessed Feb. 5, 2009.
Third Party Observations pursuant to Art. 115 EPC, mailed Jun. 17, 2016 for EP Application No. 11827484.4, 4 pages.
Thisted. What is a P value? The University of Chicago 1998. Corrections Feb. 14, 2010. http://www.stat.uchicago.edu/~thisted/.
Thomas, et al. High-throughput oncogene mutation profiling in human cancer. Nat Genet. Mar. 2007;39(3):347-51. Epub Feb. 11, 2007.
Thomas, et al. Sensitive mutation detection in heterogeneous cancer specimens by massively parallel picoliter reactor sequencing. Nat Med. Jul. 2006;12(7):852-5.
Thomas Jarvie, Next Generation sequencing technologies, Drug Discovery Today, vol. 2, No. 3, Oct. 1, 2005, pp. 255-260, XP005118465.
Torchia, et al. Archaeal RNA ligase is a homodimeric protein that catalyzes intramolecular ligation of single-stranded RNA and DNA. Nucleic Acids Res. Nov. 2008;36(19):6218-27. doi: 10.1093/nar/gkn602. Epub Oct. 1, 2008.
Trowe, et al. EXEL-7647 inhibits mutant forms of ErbB2 associated with lapatinib resistance and neoplastic transformation. Clin Cancer Res. Apr. 15, 2008;14(8):2465-75.
Tucker, et al. Massively Parallel Sequencing: The Next Big Thing in Genetic Medicine, The American Journal of Human Genetics, Aug. 14, 2009, 85:142-154.
Turner, et al. Massively parallel exon capture and library-free resequencing across 16 genomes. Nat Methods. May 2009; 6(5): 315-6. doi: 10.1038/nmeth.f.248. Epub Apr. 6, 2009.
Twelves, et al. Capecitabine as adjuvant treatment for stage III colon cancer. N Engl J Med. Jun. 30, 2005;352(26):2696-704.
U.S. Appl. No. 16/154,307 Office Action dated Dec. 7, 2021.
Vigneault, et al. Efficient microRNA capture and bar-coding via enzymatic oligonucleotide adenylation. Nature Methods 5, 777-779 (Aug. 2008).
Volkerding, et al. Next-generation sequencing: from basic research to diagnostics. Clin Chem. Apr. 2009; 55(4): 641-58. doi: 10.1373/clinchem.2008.112789. Epub Feb. 26, 2009.
Wang, et al. Digital karyotyping. Proc Natl Acad Sci U S A. Dec. 10, 2002;99(25):16156-61. Epub Dec. 2, 2002.
Wang, et al. Droplet-based micro oscillating-flow PCR chip. J. Micromech. Microeng. 2005; 15:1369-1377. doi:10.1088/0960-1317/15/8/001.
Wang, et al. Nrf2 enhances resistance of cancer cells to chemotherapeutic drugs, the dark side of Nrf2. Carcinogenesis. Jun. 2008;29(6):1235-43. Epub Apr. 15, 2008.
Warnex. Warnex Offers New Personalized Medicine Service: K-Ras Mutation Analysis for Colorectal Cancer. Feb. 3, 2009. http://www.warnex.ca/en/news-events/press-release.php?id=164. Access Aug. 23, 2012.
White, et al. Digital PCR provides sensitive and absolute calibration for high throughput sequencing. BMC Genomics. Mar. 19, 2009;10:116. doi: 10.1186/1471-2164-10-116.
Wolf, et al. Pharmacogenomics. BMJ. Apr. 8, 2000; 320:987-990.
Wong, et al. Using predictive biomarkers to select patients with advanced colorectal cancer for treatment with epidermal growth factor receptor antibodies. J Clin Oncol. Dec. 10, 2008;26(35):5668-70.
Xie et al. Pharmacogenomics steps toward personalized medicine. Personalized Medicine, vol. 2, No. 4. Published Online:Oct. 28, 2005. pp. 325-337.
Zhang, et al. A novel real-time quantitative PCR method using attached universal template probe. Nucleic Acids Res. Oct. 15, 2003;31(20):e123(pp. 1-8).
Zhang, et al. Copy number variation in human health, disease, and evolution. Annu Rev Genomics Hum Genet. 2009; 10:451-81. doi: 10.1146/annurev.genom.9.081307.164217.
Zhang, et al. Miniaturized PCR chips for nucleic acid amplification and analysis: latest advances and future trends. Nucleic Acids Res. 2007; 35(13): 4223-37. Epub Jun. 18, 2007.
Zhang, et al. Presence of donor- and recipient-derived DNA in cell-free urine samples of renal transplantation recipients: urinary DNA chimerism. Clin Chem. Oct. 1999;45(10):1741-6.
Zhang, et al. Single-Stranded DNA Ligation by T4 RNA Ligase for PCR Cloning of 5'-Noncoding Fragments and Coding Sequence of a Specific Gene. Nucl. Acids Res. (1996), 24(5): 990-991.
Zhelkovsky, et al. Structure-function analysis of Methanobacterium thermoautotrophicum RNA ligase—engineering a thermostable ATP independent enzyme. BMC Mol Biol. Jul. 18, 2012;13:24. doi: 10.1186/1471-2199-13-24.
Zuckermann, et al. Efficient methods for attachment of thiol specific probes to the 3'-ends of synthetic oligodeoxyribonucleotides. Nucleic Acids Res. Jul. 10, 1987; 15(13): 5305-21.
Blagosklonny, Mikhail. Analysis of FDA approved anticancer drugs reveals the future of cancer therapy. Cell Cycle. vol. 3(8)(2004):1035-42. Epub Aug. 16, 2004. PMID: 15254418.
Co-pending U.S. Appl. No. 18/418,774, inventors Stephan; Dietrich et al., filed on Jan. 22, 2024.
Co-pending U.S. Appl. No. 18/418,781, inventors Stephan; Dietrich et al., filed on Jan. 22, 2024.
Papadopoulou et al., Cell-free DNA and RNA in Plasma as a New Molecular Marker for Prostate and Breast Cancer, Ann. NY, Acad. Sci. 1075:235-243 (2006).
Sotiriou, Christos, et al. Breast cancer classification and prognosis based on gene expression profiles from a population-based study. Proceedings of the National Academy of Sciences of the United States of America vol. 100,18 (2003): 10393-8.
U.S. Appl. No. 16/154,307 Notice of Allowance dated Jan. 5, 2024.
U.S. Appl. No. 16/154,307 Notice of Allowance dated Mar. 20, 2024.
U.S. Appl. No. 16/154,307 Office Action dated Sep. 26, 2023.
U.S. Appl. No. 18/356,900 Notice of Allowance dated Mar. 20, 2024.
U.S. Appl. No. 18/356,900 Office Action dated Dec. 11, 2023.
Generali, Daniele, et al. EGFR mutations in exons 18-21 in sporadic breast cancer. Annals of oncology 18.1: 203-205. (2007).
Karakas, B. et al. Mutation of the PIK3CA Oncogene in Human Cancers. British Journal of Cancer 94(4):455-459 (2006).
Karakas, B., K. E. Bachman, and B. H. Park. Mutation of the PIK3CA oncogene in human cancers. British journal of cancer 94.4: 455-459. (2006).
Martinez-Lopez, Eva. et al. Allelic Loss on Chromosome 18q as a Prognostic Marker in Stage II Colorectal Cancer. Gastroenterology 114(6):1180-1187 (1998).
Minoo, P. et al. Role of BRAF-V600E in the Serrated Pathway of Colorectal Tumourigenesis. Journal of Pathology 212(2):124-133 (2007).
Momparler, Richard L., et al. DNA methylation and cancer. Journal of cellular physiology 183.2: 145-154. (2000).
Paradiso, Angelo. et al. Topoisomerase-I, Thymidylate Synthase Primary Tumour Expression and Clinical Efficacy of 5-FU/CPT-11 Chemotherapy in Advanced Colorectal Cancer Patients. International Journal of Cancer 111(2):252-258 (2004).

(56) References Cited

OTHER PUBLICATIONS

Ricci-Vitiani, Lucia. et al. Identification and Expansion of Human Colon-cancer-initiating Cells. Nature 445(7123):111-115 (2007).
U.S. Appl. No. 18/418,774 Office Action dated Jul. 12, 2024.
U.S. Appl. No. 18/418,781 Restriction Requirement dated Jul. 9, 2024.
U.S. Appl. No. 18/533,538 Office Action dated Jul. 11, 2024.
U.S. Appl. No. 18/418,781 Non-Final Office Action dated Aug. 9, 2024.
Wu, Tsu-Lan, et al. Cell-free DNA: measurement in various carcinomas and establishment of normal reference range. Clinica chimica acta 321.1-2: 77-87. (2002).

* cited by examiner

FIG. 2A

FIG. 2B
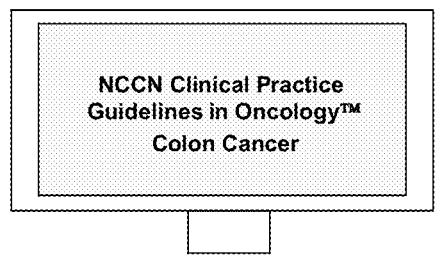
FIG. 2C
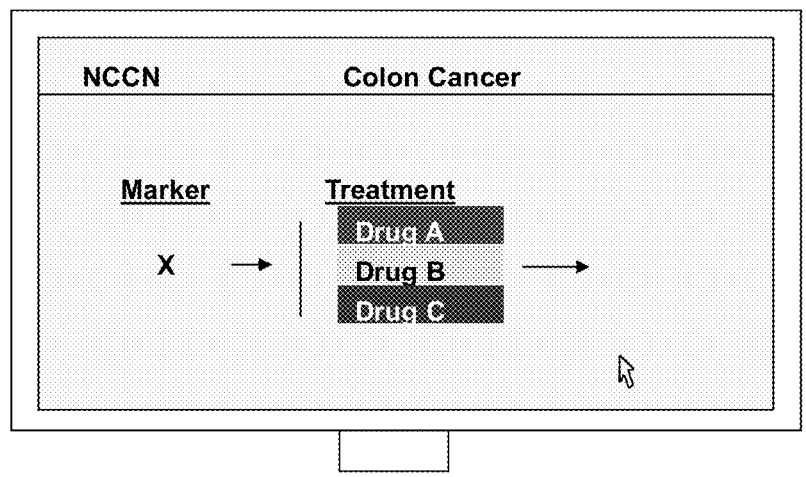

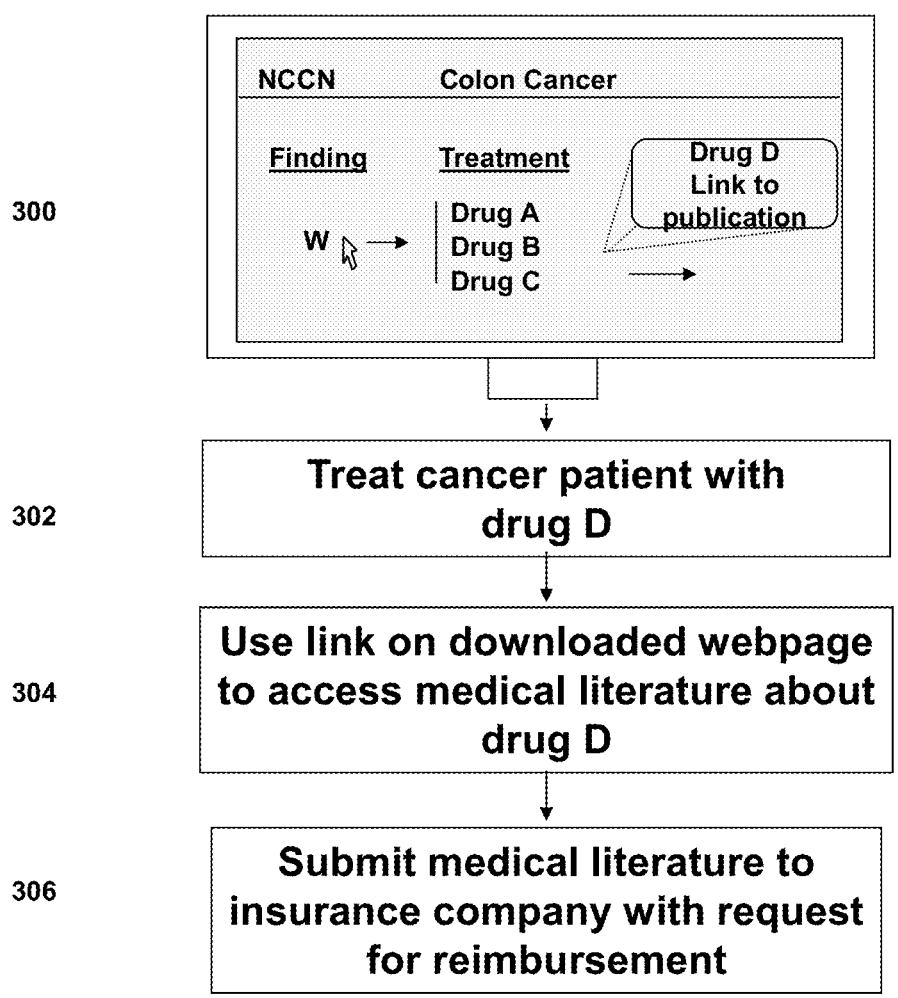

FIG. 6

| Marker*/Target | Genetic Variant | Drug/Therapeutic | Cancer | Test Method | Reference | Stage, grade, subclass | Notes |
|---|---|---|---|---|---|---|---|
| ER | | hormonal therapeutics | breast | IHC | | | |
| PR | | hormonal therapeutics | breast | IHC | | | |
| Oncotype Dx | expression profile | tamoxifen | breast | RT PCR | | | |
| ErbB2 | overexpression | | breast | | | metastatic | GSK Clin Trial enrolling 11/2008 |
| PAM 50 expression signature | expression | endocrine therapy | breast | RT PCR | Ellis, et al., 2008 J. Clin Oncology 26. ACOSOG trial Z1031 | response to endocrine therapy | Validation underway in CLIA lab |
| Philadelphia chromosome (bcr/abl) | Ph+ | imatinib mesylate (Gleevec) | CML | | | initial therapy, chronic phase, failure of interferon alpha thx. | |
| vras, kras | | bevacizumab (Avastin) | colon | | Grothey et al., ASCO, The Role of Biomarkers in Targeted Therapy for Colorectal Cancer www.medscape.com/viewarticle/577606 | metastatic | |
| | | capecitabine (Xeloda) | colon | | | metastatic, adjuvant Dukes C | |
| Veristrat serum protein signature | | cetuximab (Erbitux) | colon | tandem mass spec | David Carbone | predictive of response t | |
| kras | mutation | cetuximab (Erbitux) | colon | NCCN | FDA reviewing label recommendations 12/16/08 | | |
| EGFR | expression | cetuximab (Erbitux) | colon | | FDA approved for EGFR-expressing, metastatic colorectal carcinoma | irinotecan resistant tumors | Accel Approval, refractory to irinotecan chemo |
| BRAF | V600E | cetuximab | colon | Sequencing | Journal of Clinical Oncology, Vol 26, No 35 (December 10), 2008: pp 5705-5712 | | |

FIG. 6 (cont.)

| Marker*/Target | Genetic Variant | Drug/Therapeutic | Cancer | Test Method | Reference | Stage, grade, subclass | Notes |
|---|---|---|---|---|---|---|---|
| TOPO1 | low expression* | fluorouracil, 5-FU (Adrucil) | colon | IHC | Braun et al., J Clin Onc, 2008 26(16):2690 | use 5 fu alone, combination of irinotecan or oxaliplatin shows no benefit | |
| TOPO1 | mod/high expression* | fluorouracil, 5-FU (Adrucil) | colon | IHC | Braun et al., J Clin Onc, 2008 26(16):2690 | prolong survival in combination with irinotecan or oxaliplatin | |
| TOPO1* | | irinotecan (Camptosar) | colon | | | metastatic, recurrence or progression after 5-FU thx | |
| | | leucovorin (Leucovorin, Wellcovorin) | colon | | | combination with 5-FU, prolong survival, palliative | |
| | | levamisole (Ergamisol) | colon | | | Dukes Stage C, combination with 5-FU after surgical resection | |
| | | oxaliplatin (Eloxatin) | colon | | | metastatic, combination with 5FU/LV | |
| kras | mutation | panitumumab (Vectibix) | colon | NCCN, FDA reviewing label | FDA reviewing label recommendations 12/16/08 | metastatic | |
| | | celecoxib (Celebrex) | colon, FAP, polyp reductio | | | polyp reduction, FAPC | Accel Approval |
| | | capecitabine | colon, rectal | | NCCN | | |

FIG. 6 (cont.)

| Marker*/Target | Genetic Variant | Drug/Therapeutic | Cancer | Test Method | Reference | Stage, grade, subclass | Notes |
|---|---|---|---|---|---|---|---|
| kras | wild type | cetuximab | colon, rectal | Sequencing | NCCN | stage 4 COL 5, COL 9 COL 10 | for patients not able to tolerate cetuximab +irinotecan |
| | | Irinotecan | colon, rectal | | NCCN | | |
| kras | wild type | penitumumab | colon, rectal | | NCCN | stage 4 COL 5, COL 9 COL 10 | for patients not able to tolerate cetuximab +irinotecan |
| | | mitomycin C (Mitozytrex) | GI | | | disseminated adenocarcinoma, palliative | |
| CD117 positive (Kit positive) | expression, mutation | imatinib mesylate (Gleevec) | GI tumors | Expression and DNA sequencin | NCCN | malignant, metastatic, unresectable | |
| | | Cyclophosphamide (Neosar, Cytoxan) | lung | | | | |
| Nrf2 | | doxorubicin (Adriamycin) | lung | | Wang et al., Carcinogenesis, Jun 2008; 29: 1235 | drug resistance factor | research finding |
| DPD | negative | fluorouracil (5-FU) | lung, NSCLC | tandem MS | British Journal of Cancer (2006) 95, 607. | | |
| DPRT | positive | fluorouracil, 5-FU | lung, NSCLC | | British Journal of Cancer (2006) 95, 607. | | |
| TS | negative | fluorouracil, 5-FU | lung, NSCLC | | British Journal of Cancer (2006) 95, 607 | | |
| Topo1 | | fluorouracil, 5-FU | colon | | | combination therapy with 5-FU, progression free survival, overall survival | |
| biomarker correlation study Roche | | bevacizumab (Avastin) | lung, NSCLC | | Clinical trial enrolling patients Dec 2008 Roche | NSCL, metastatic, locally advanced | |
| | | docetaxel (Taxotere) | lung, NSCLC | | | metastatic | |

FIG. 6 (cont.)

| Marker*/Target | Genetic Variant | Drug/Therapeutic | Cancer | Test Method | Reference | Stage, grade, subclass | Notes |
|---|---|---|---|---|---|---|---|
| kras | mutation | gefitinib (Iressa) | lung, NSCLC | NCCN | Carbone (2004) Nature Clinical Practice Oncology 20Sjai | | randomized phase III trial |
| | | gemcitabine (Gemzar) | lung, NSCLC | | | first line, inoperable stage IIIA, IIIB or metastatic stage | |
| | | vinorelbine (Navelbine) | lung, NSCLC | | | unresectable advanced, alone or with cisplatin, Stage III, IV | |
| Serum protein signature (40 marker) | | erlotinib (Tarceva) | lung, NSCLC, ADC, SCC | Tandem Mass spec@Biode six CLIA lab | Clinical trial/Carbone | metastatic | seeking funding for Clin Trial |
| kras/EGFR | mutation | erlotinib (Tarceva) | lung, NSCLC, ADC, SCC | Pao et al., 2005 PLoS, Med., 2(1):e17 | | first line | |
| | | topotecan (Hycamtin) | lung, small cell | | | failure of first line or cancer progressing after initial response to chemo | |
| | | pemetrexed disodium (Alimta) | lung,NSCLC | | | locally advanced, metastatic | Accel Approval, clinical benefit not established |
| | | porfimer sodium (Photofrin) | lung,NSCLC | | | photdynamic therapy | |
| | | paclitaxel (Taxol) | lung,SSCLC | | | first line, comb with cisplatin | |

FIG. 6 (cont.)

| Marker*/Target | Genetic Variant | Drug/Therapeutic | Cancer | Test Method | Reference | Stage, grade, subclass | Notes |
|---|---|---|---|---|---|---|---|
| | | bleomycin (Blenoxane) | pleural effusion, MPE | | | malignant | |
| | | leucovorin (Leucovorin, Wellcovorin) | prostate | | | combination with 5-FU, prolong survival, palliative | |
| | | FDA Approved | | | | | |
| EGFR | overexpression | lapatinib | | sequencing, expression | Clinical Cancer Research 14, 2465-2475, April 15, 2008 | | confer drug resistance, |
| ErbB2 | mutations | leucovorin | | | NCCN | | |
| | | oxaliplatin | | | NCCN | | |
| Topo1 | | oxaliplatin | colon | IHC | Braun et al., J Clin Onc, 2008 26(16):2690 | | |
| | | etoposide phosphate (Etopos) | lung, small cell | | | | |
| *Validated markers are in black | | | | | | | |

Work Flow – Library preparation and sequencing

METHODS FOR SEQUENCING SAMPLES

CROSS-REFERENCE

This application is a continuation of U.S. application Ser. No. 16/154,307, filed Oct. 8, 2018, which is a continuation of U.S. application Ser. No. 15/183,655, filed Jun. 15, 2016, which is a divisional of U.S. application Ser. No. 14/927,254, filed Oct. 29, 2015, which is a continuation of U.S. application Ser. No. 14/075,996, filed Nov. 8, 2013, which is a continuation of U.S. application Ser. No. 13/060,425, filed Jun. 2, 2011, now U.S. Pat. No. 8,583,380, which is a National Stage Entry of International Application Serial No. PCT/US2009/056101, filed Sep. 4, 2009, which claims benefit of U.S. Provisional Patent Application Ser. No. 61/094,855, filed Sep. 5, 2008, U.S. Provisional Patent Application Ser. No. 61/155,477, filed Feb. 25, 2009, U.S. Provisional Patent Application Ser. No. 61/173,179, filed Apr. 27, 2009, and U.S. Provisional Patent Application Ser. No. 61/231,287, filed Aug. 4, 2009, which applications are incorporated herein by reference in their entireties.

BACKGROUND OF THE INVENTION

Approximately 50% of Americans will get cancer and approximately 50% of those will die from cancer. Ten cancers made up approximately 70% of the 1.4 million estimated new U.S. cases in 2008. The NIH estimated that the total costs of cancer in 2007 were $219.2 billion, with direct medical costs at $89.0 billion (total of all health expenditures), indirect morbidity costs at $18.2 billion (cost of lost productivity due to illness), and indirect mortality costs at $112.0 billion (cost of lost productivity due to premature death).

There are approximately 150 oncology drugs, and over 2000 in development. Many drugs have known or measurable targets. However, cancer patients are not routinely screened for the status of these targets (or markers), and markers are not used to determine which drug treatment options the patients receive. Rather, cancers are often treated by organ. Furthermore, an integrated source of knowledge regarding molecular markers and drug targets for physicians or patients is lacking.

Personalized medicine involves the use of molecular markers that characterize a patient's disease to direct the medical care the patient receives. The scientific literature provides examples where the efficacy of a cancer drug can be correlated with the status of a molecular marker. There is a need to improve the ability of health care providers to access and interpret information in the scientific literature regarding connections between molecular markers and drug efficacy. This information will allow health care providers to use molecular markers to select appropriate standard chemotherapy.

Another issue surrounding cancer treatment is the reimbursement of fees associated with treatments. Medicare can reimburse for off-label use of cancer drugs included in certain medical compendia. Additionally, peer-reviewed medical journals can provide guidance to Medicare contractors with respect to medically appropriate off-label uses of cancer drugs supported by results of clinical trials. There is a need to ensure the latest peer-reviewed information regarding off-label use of cancer drugs and information about experimental drugs supported by results of clinical trials is readily accessible to physicians and patients when a cancer drug treatment decision is made or when reimbursement from an insurance company is being sought.

SUMMARY OF THE INVENTION

In general, in one aspect, a method for generating a personalized cancer drug treatment option report is provided including obtaining a sample from a subject, determining the status of one or more molecular markers in the sample, stratifying one or more cancer drug treatment options in the report based on the status of the one or more molecular markers, and annotating the report based on the status of the one or more molecular markers.

The subject can be a cancer patient. The cancer patient can be a colon cancer patient. The sample can be a tumor biopsy. The sample can be preserved by formalin-fixing and paraffin-embedding. The determining can include nucleic acid amplification, DNA sequencing, FISH, qPCR, and/or IHC. The DNA sequencing can include de novo DNA sequencing. The de novo DNA sequencing can include bridge amplification of DNA. The sample can include genomic DNA from an FFPE sample and the determining can include bridge amplification and DNA sequencing.

The method can further include purifying cancer cells from the sample. The purifying can include flow sorting or laser capture microdissection. The sample can be a tumor biopsy obtained by fine needle aspiration, the sample can be frozen, and the purifying can include flow sorting.

The stratifying can include stratifying the drug treatment options for a condition in the NCCN Clinical Practice Guidelines in Oncology™ or the American Society of Clinical Oncology (ASCO) clinical practice guidelines. The condition can be colon cancer. The stratifying can be based on information in scientific literature. The stratifying can take into account the status of one or more molecular markers in drug absorption, distribution, metabolism, or excretion genes in a sample from the subject. The determining can include analyzing the sequence of UGT1A1 for one or more SNPs. The stratifying can take into account whether the subject is hypermetabolic. The stratifying can take into account the CYP450 status of the subject. The stratifying and/or the annotating can be based on clinical information for the subject. The stratifying can include ranking drug treatment options with a higher likelihood of efficacy higher than drug treatment options with a lower likelihood of efficacy or for which no information exists with regard to treating subjects with the determined status of the one or more molecular markers. The stratifying can include indicating on the report one or more drug treatment options for which scientific information suggests the one or more drug treatment options will be efficacious in a subject, based on the status of one or more molecular markers in the sample from the subject. The stratifying can include indicating on a report one or more drug treatment options for which some scientific information suggests the one or more drug treatment options will be efficacious in the subject, and some scientific information suggests the one or more drug treatment options will not be efficacious in the subject, based on the status of one or more molecular markers in the sample from the subject. The stratifying can include indicating on a report one or more drug treatment options for which scientific information indicates the one or more drug treatment options will not be efficacious for the subject, based on the status of one or more molecular markers in the sample from the subject. The stratifying can include color coding the listed drug treatment options on the report based on the rank of the predicted efficacy of the drug treatment options.

The annotating can include annotating a report for a condition in the NCCN Clinical Practice Guidelines in Oncology™ or the American Society of Clinical Oncology (ASCO) clinical practice guidelines. The annotating can include listing one or more FDA-approved drugs for off-label use, one or more drugs listed in a Centers for Medicare and Medicaid Services (CMS) anti-cancer treatment compendia, and/or one or more experimental drugs found in scientific literature, in the report. The annotating can include connecting a listed drug treatment option to a reference containing scientific information regarding the drug treatment option. The scientific information can be from a peer-reviewed article from a medical journal. The annotating can include using information provided by Ingenuity® Systems. The annotating can include providing a link to information on a clinical trial for a drug treatment option in the report. The annotating can include presenting information in a pop-up box or fly-over box near provided drug treatment options in an electronic based report. The annotating can include adding information to a report selected from the group consisting of one or more drug treatment options, scientific information concerning one or more drug treatment options, one or more links to scientific information regarding one or more drug treatment options, one or more links to citations for scientific information regarding one or more drug treatment options, and clinical trial information regarding one or more drug treatment options.

The sample can include colon cancer cells, the one or more molecular markers can include c-kit, and the one or more drug treatment options can include imatinib mesylate.

The sample can include colon cancer cells, the one or more molecular markers can include Kras, and the one or more drug treatment options can include cetuximab, panitumumab, or bevacizumab. If exon 2 of Kras does not have a mutation, the stratifying and/or annotating can include recommending cetuximab or panitumumab monotherapy for the subject. If exon 2 of Kras has a mutation, the stratifying and/or annotating can include recommending cetuximab or panitumumab monotherapy not be given to the subject.

The sample can include colon cancer cells, the one or more molecular markers can include BRAF, and the one or more drug treatment options can include cetuximab or panitumumab. The determining can include determining the presence or absence of the BRAF V600E mutation. If BRAF sequence encodes a V600E mutation, the stratifying and/or annotating can include providing a recommendation in the report to the treat the subject with sorafenib and cetuximab and/or panitumumab.

The determining can include determining the status of microsatellite sequences. If the microsatellite sequences display low-frequency microsatellite instability, and the sample is a stage II or stage III colon cancer, the stratifying and/or annotating can include recommending fluorouracil-based adjuvant chemotherapy for the subject. If the microsatellite sequences display high-frequency microsatellite instability, and the sample is a stage II or stage III colon cancer, the stratifying and/or annotating can include making a recommendation to not administer fluorouracil-based adjuvant chemotherapy for the subject.

The determining can include determining EGFR copy number. If EGFR copy number is increased relative to normal, the stratifying and/or annotating can include recommending cetuximab or panitumumab monotherapy to the subject.

The determining can include determining if the sample has 18q chromosome loss. If the subject is a stage II colorectal cancer patient with chromosome 18q allelic loss the stratifying and/or annotating can include recommending adjuvant therapy for the subject.

The determining can include determining thymidylate synthase levels. If thymidylate synthase levels are high, the stratifying and/or annotating can include recommending adjuvant 5-FU-based chemotherapy not be given to the subject in the report. If thymidylate synthase levels are low, the stratifying and/or annotating can include recommending to treat the subject with adjuvant 5-FU-based chemotherapy.

The sample can include colon cancer cells, the one or more molecular markers can include Topo1, and the one or more drug treatment options can include 5-FU, irinotecan, or capecitabine. If Topo1 expression is low, the stratifying and/or annotating can include making a recommendation to not treat the subject with irinotecan. If Topo1 expression is moderate to high, the stratifying and/or annotating can include making a recommendation to treat the subject with irinotecan.

The method can further include sending a kit to a health care provider that provides health care to the subject. The kit can include RNAlater®.

The method can further include establishing an in vitro culture using the sample. The method can further include high-throughput screening of FDA approved off-label drugs or experimental drugs using the in vitro culture.

The method can further include establishing a xenograft model using the sample. The method can further include high-throughput screening of FDA approved off-label drugs or experimental drugs using the xenograft model. The sample can be a tumor biopsy, the subject can be a cancer patient with end stage cancer, and results of the high-throughput screening can be used to determine an adjuvant therapy for administration to the cancer patient.

The method can further include monitoring tumor antigen for recurrence detection.

The determining can include de novo DNA sequencing and the stratifying can be based on analysis of a Kaplan-Meier survival curve.

The method can further include charging a fee for generating the report.

In another aspect, a method for generating a personalized cancer drug treatment option report is provided including: a) obtaining a sample from a subject; b) determining the status of one or more molecular markers in the sample; c) stratifying drug treatment options listed in a clinical practice guideline for a condition based on the status of the one or more molecular markers in the sample; and d) optionally annotating the report with information comprising information regarding one or more additional drug treatment options not listed in the clinical practice guideline for the condition, wherein the information is included based on the status of the one or more molecular markers in the sample. The clinical practice guideline can be the NCCN Clinical Practice Guidelines in Oncology or the American Society of Clinical Oncology (ASCO) clinical practice guidelines. The one or more additional drug treatment options can be described in National Comprehensive Cancer Network (NCCN) Drugs and Biologics Compendium™, Thomson Micromedex DrugDex®, Elsevier Gold Standard's Clinical Pharmacology, or American Hospital Formulary Service—Drug Information Compendium. The one or more additional drug treatment options can include a drug used in a clinical trial. The one or more additional drug treatment options can include a drug described in a scientific journal article.

The annotating can further include listing information in the report referencing one or more scientific journal articles that describe the use of one or more additional drug treatment options.

The one or more additional drug treatment options can target a molecular marker that is in a pathway for which the status of another molecular marker indicates that targeting the pathway would be efficacious for treating the subject. The stratifying can be indicated by color coding drug treatment options listed on the report. The color code can include a shade of green, a shade of yellow, and a shade of red. The drug treatment options associated with a green shade can be drugs that are recommended to the subject based on the status of the one or more molecular markers. The drug treatment options associated with a yellow shade can be drugs that have some information that supports recommending the drug as a treatment option to the subject based on the status of the one or more molecular markers and at least one piece of information does not support recommending the drug as a treatment option. The drug treatment options associated with a red shade can be drugs for which the status of the one or more molecular markers does not support recommending the drug treatment option to the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-2C illustrates a physician accessing a report provided by a personalized medicine business based on the NCCN Clinical Practice Guidelines in Oncology™ on a computer and finding the drug treatment options for colon cancer stratified based on the status of a molecular marker present in the cancer.

FIG. 3 illustrates a method for accessing a report provided by a personalized medicine business based on the NCCN Clinical Practice Guidelines in Oncology™ on a computer, selecting an annotated drug treatment, accessing scientific information regarding the drug treatment, and submitting the information to an insurance company.

FIG. 6 shows molecular markers or drug targets that can be identified in a subject and drug treatment options that can be recommended to the subject with the molecular marker, references, and methods of testing the status of a molecular marker.

DETAILED DESCRIPTION OF THE INVENTION

I. Overview

In general, methods are disclosed herein for a service that provides personalized cancer drug treatment options based on the status of one or more molecular markers in a patient's sample, e.g., a tumor biopsy. The disclosed methods can include stratifying cancer drug treatment options and/or annotating cancer drug treatment options with scientific information on a report, e.g., a printed form. The scientific information can be made accessible to a patient or one or more health care providers and can be used for insurance reimbursement purposes to aid selection of one or more drug treatment options.

Figure 1:
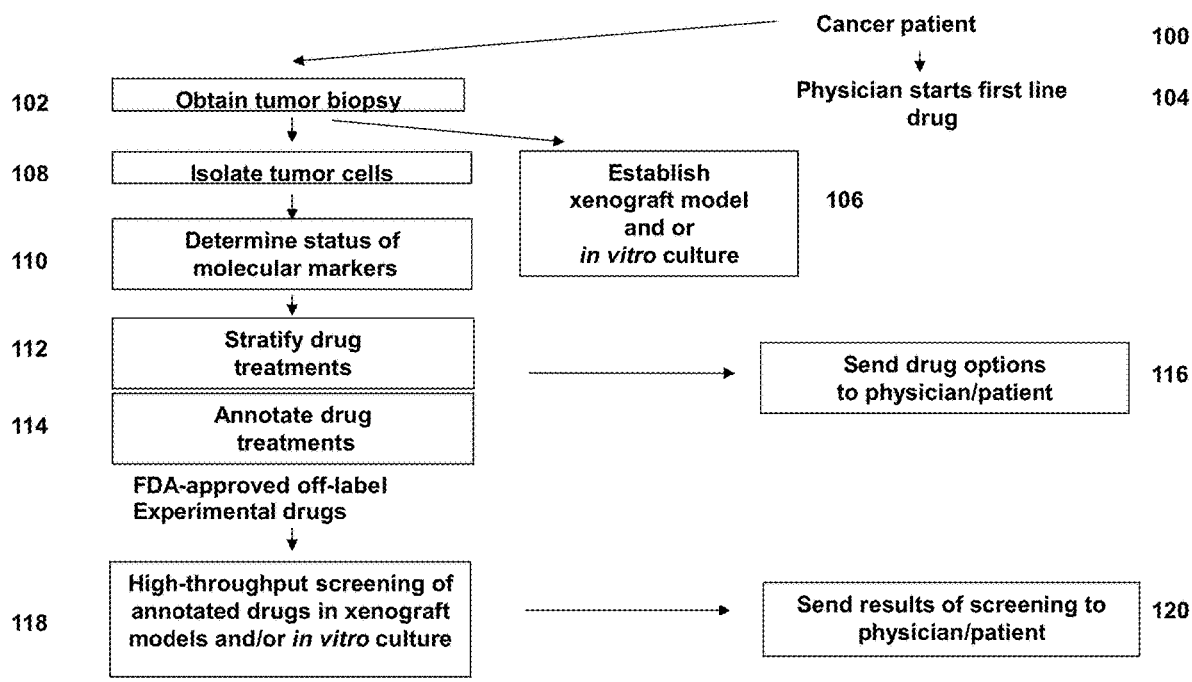
FIG. 1 is a flow diagram of a personalized medicine service.
Figure 4:
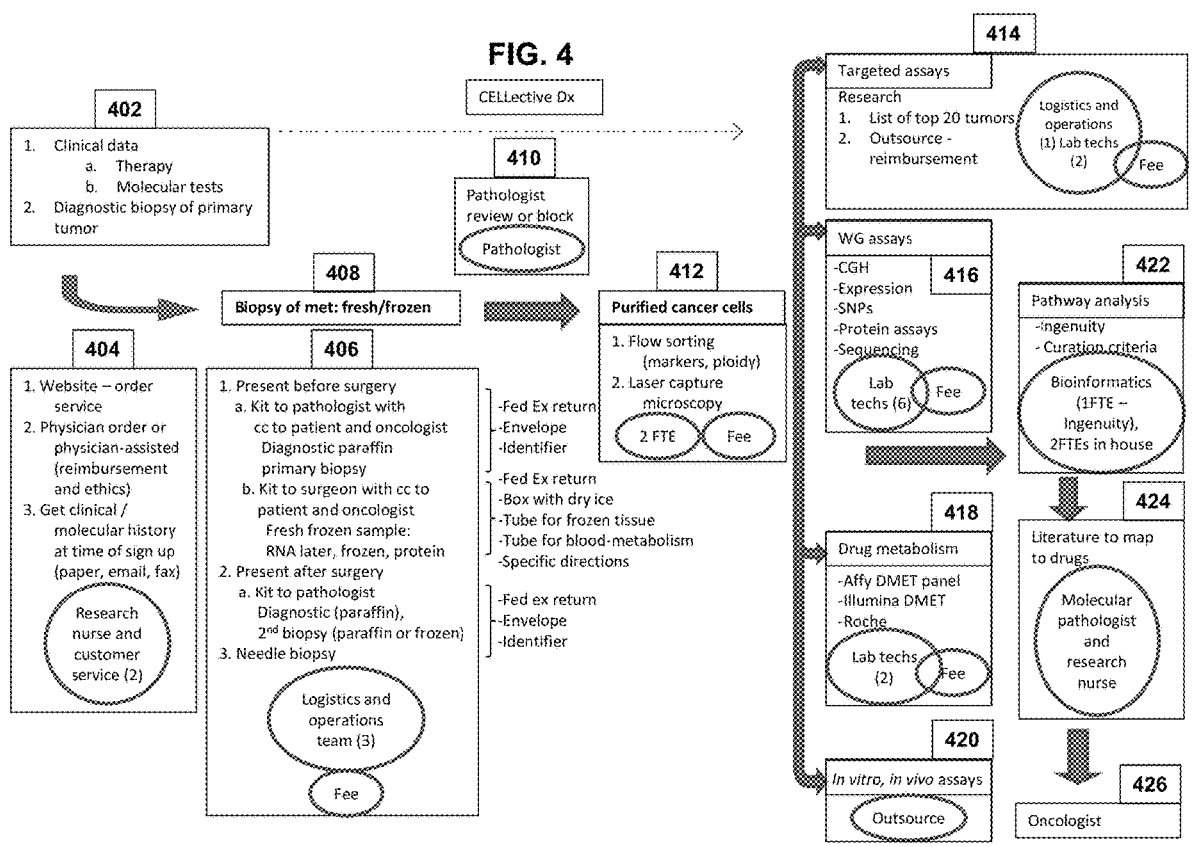
FIG. 4 illustrates a flow diagram for a personalized medicine service for identifying (determining the status of) molecular markers from a subject and reporting drug treatment options to the subject.

FIG. 1 provides an overview of one aspect of the provided method. A cancer patient (100) visits a health care provider, and the health care provider performs a tumor biopsy (102) and potentially begins a first line drug treatment (104). The tumor biopsy is then sent to a personalized medicine business for analysis and testing. In one pathway (106), the tumor is used to establish an in vitro culture and/or xenograft model for future drug testing. In another pathway, the tumor cells can be isolated from non-tumor cells in the biopsy (108) and used to identify (determine the status of) molecular markers (110). For example, the status of one or more molecular markers can be determined by comparative genomic hybridization (CGH), high density expression, de novo sequencing, or genotyping. The molecular markers can then be used to stratify a list of cancer drug treatments (112). The identified molecular markers can also be used as the basis for annotating the drug treatment options by, for example, providing links to scientific information for experimental drugs and FDA-approved drugs for off-label use (114). The links to scientific literature can be used to send literature to insurance companies for reimbursement purposes. The stratified and annotated cancer drug treatment options can then be provided in the form of a report to the health care provider and/or patient (116), who can use the information to select a second line drug treatment therapy, for example, if the first line therapy fails. The stratified and annotated drug treatment options can be tested in high-throughput screens using the established in vitro cultures or xenograft models (118). Results of the screens can be given to the physician (120), who can use the information to select adjuncts for end stage administration, for example. One or more fees can be charged by the personalized medicine business in exchange for any of the services.

In one aspect, a method is provided that includes a) obtaining a sample from a subject, b) identifying (determining the status of) one or more molecular markers in the sample, c) stratifying one or more drug treatment options based on the status of one or more molecular markers, and d) annotating drug treatment options based on the status of one or more molecular markers.

In another aspect, a method is provided that provides personalized cancer drug treatment options, including a) receiving an order, b) obtaining a sample from a subject, c)

purifying cancer cells from the sample, d) identifying (determining the status of) one or more molecular markers in the cancer cells, e) stratifying one or more drug treatment options in a report, f) annotating one or more drug treatment options in a report, and g) charging a fee for one or more of steps (a)-(f).

In another aspect, a method for generating a personalized cancer drug treatment option report is provided including a) obtaining a sample from a subject; b) determining the status of one or more molecular markers in the sample; c) stratifying drug treatment options listed in a clinical practice guideline for a condition based on the status of the one or more molecular markers in the sample; and d) optionally annotating the report with information comprising information regarding one or more additional drug treatment options not listed in the clinical practice guideline for the condition, wherein the information is included based on the status of the one or more molecular markers in the sample.

Figure 5:
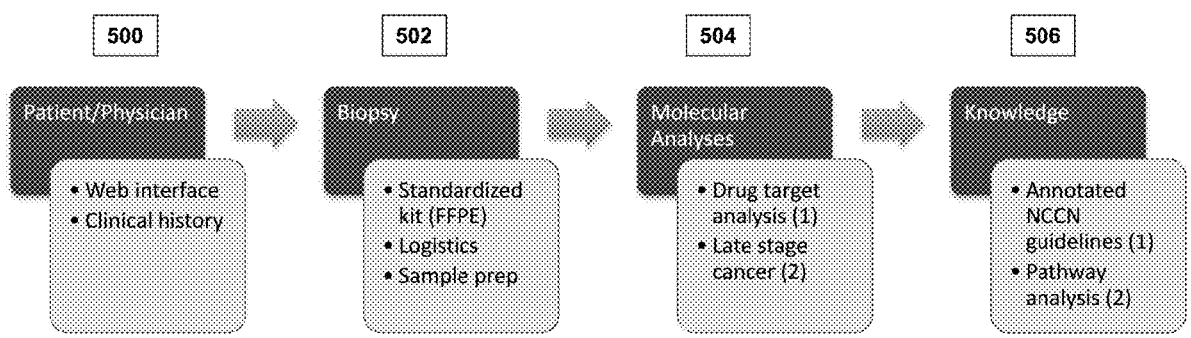
FIG. 5 is a flow diagram for providing personalized treatment options to a patient or physician.

Another aspect of a method of the provided invention is shown in FIG. 5, in which a patient or physician interfaces with a personalized medicine business (500), a biopsy is performed (502), a molecular analysis is performed (504), and information is analyzed to provide recommendations to the patient or physician (506) based on the status of one or more molecular markers. The information can be scientific literature and/or clinical trial information. The analysis can include annotating a clinical practice guideline for a condition (e.g., NCCN Clinical Practice Guidelines in Oncology) with information (e.g., references to scientific journal articles; other drug treatment options). The analysis can include analysis of molecular pathways that include drug targets, e.g., drug targets not recommended in the clinical practice guideline for the condition, that may be efficacious for the patient based on the status of one or more molecular markers in the biopsy.

II. Obtaining a Sample

The subject from whom a sample is taken can be a patient, for example, a cancer patient or a patient suspected of having cancer. The subject can be a mammal, e.g., a human, and can be male or female. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

A. Receiving an Order

The methods of the provided invention can include a step in which a personalized medicine business receives an order. The order received by the personalized medicine business can be placed by a health care provider, including, for example, a physician, physician assistant, nurse, veterinarian, dentist, chiropractor, paramedic, dermatologist, oncologist, gastroenterologist, or surgeon. The order can be placed on behalf of a subject from whom a sample is taken, e.g., a cancer patient. The order can be placed by the subject from whom a sample has been or will be taken, and the subject can place the order with the guidance or supervision of a health care provider. The order can be submitted to the personalized medicine business using any of a variety of means. For example, an order can be placed using a computer website (a web interface), by sending an email, a facsimile, or a text message, or by placing a phone call to the personalized medicine business. If a website or web interface is used, the website or web interface can be maintained by the personalized medicine business. The person placing the order can create or be given a username and/or password. An order form can be downloaded from a website, sent through the mail, sent using email, or sent by facsimile. The order can be placed by filling out one or more forms and submitting it (them) to the personalized medicine business using a computer (e.g., web interface, email) or through a mail or other delivery service, for example, the U.S. Postal Service, a courier service, Federal-Express, DHL, or UPS.

A diagnostic biopsy of a primary tumor can be taken before or after an order is placed. The status of one or more molecular markers in a tumor of the subject can be identified (determined) before or after an order is placed. The subject from whom the sample is taken can be provided one or more therapies before or after an order is placed.

The order can include information regarding a sample or subject. The information can include a description of the sample, e.g., the date the sample was taken, type of sample, or other properties of the sample. The order can include information regarding the subject from whom the sample is taken. For example, this information can include height, weight, eye color, hair color, age, ethnicity, gender; clinical information, e.g., blood pressure, LDL cholesterol levels, HDL cholesterol levels, and triglyceride levels, heart rate; personal medical history, including cancer treatments already received; family medical history of the subject; and information on molecular markers.

The order can include billing information and/or insurance information. The order can contain a barcode that identifies the order. The order can contain comments or notes about the sample and/or the subject (e.g., patient). This information can be sent with the sample to the personalized medicine business.

A customer service representative employed by the personalized medicine business can process the order (e.g., enter information in the order into a database operated by the personalized medicine business). An employee of the personalized medicine business, for example, a research nurse, can review and process the clinical information. A fee can be charged by the personalized medicine business in exchange for receiving and/or processing the clinical information.

B. Kit for Processing Samples and/or Submitting Samples to a Personalized Medicine Business The personalized medicine business can provide a kit to a health care provider (e.g., a surgeon, pathologist, oncologist) involved in the care of a subject from whom a sample will be taken. A kit can contain contents that can be used to process or transport a sample from the subject.

A kit can include a reagent that protects RNA in fresh specimens including, e.g., RNAlater® Tissue Collection: RNA Stabilization Solution (Applied Biosystems) or RNA-Safer™ RNA Stabilization Reagent (SABiosciences). Compositions for preserving RNA in cells and tissues are described, for example, in U.S. Pat. Nos. 6,204,375, 7,056, 673, and 7,138,226. A kit of the provided invention can contain instruments or tools for processing a sample.

A kit can contain instructions for processing a sample. The kit can contain instructions for performing a biopsy. For example, the kit can contain instructions for performing fine needle aspiration. The kit can include instructions and/or reagents for preparing formalin-fixed, paraffin-embedded tissue or for freezing (e.g., fresh frozen) a sample. The kit can contain dry ice (e.g., pelleted dry ice). A kit can contain one or more pre-paid shipping labels. A kit can contain educational materials (e.g., a pamphlet containing information about a specific cancer).

A kit of the provided invention can contain instructions for shipping a sample, for example, to an entity that will analyze the sample.

A kit can include one or more containers, e.g., an envelope, a box, and/or a tube that can be used to transport one or more samples to the personalized medicine business. The one or more containers can be provided with identifying information, e.g., information identifying the subject from whom a sample is taken, information identifying a health care provider that will perform/has performed a biopsy, information identifying the sample type to be sent to the personalized medicine business, and information regarding a shipping address to which the sample can be sent (e.g., address of the personalized medicine business). A kit can contain logistics information; for example, the kit can contain preprinted information that can be attached to the one or more sample containers that can be returned to the personalized medicine business. The shipping information can contain a barcode for tracking the shipment or for identifying the sample. The preprinted information can contain an adhesive that permits the information to adhere to a container.

One or more logistics and operation personnel employed by the personalized medicine business can send a kit to and/or receive a kit from a health care provider. A fee can be charged by the personalized medicine business in exchange for sending a kit. Multiple individuals can be informed when a kit has been sent by the personalized medicine business; for example, the subject from whom the sample is taken (e.g., cancer patient) or an oncologist that will review the subject's information, can be informed by the personalized medicine business that a kit has been sent to a health care provider.

A kit can be sent to a pathologist and/or pathology laboratory for preparing a diagnostic paraffin primary biopsy, and the subject (e.g., cancer patient) and an oncologist can be notified that the kit has been sent to the pathologist. The pathology laboratory can be a College of American Pathologists (CAP) accredited laboratory. The laboratory can be a Clinical Laboratory Improvement Amendments (CLIA) certified laboratory. A kit for processing a biopsy can be sent to the person who will perform the biopsy (e.g., surgeon), and the subject (e.g., patient) and an oncologist can be notified that the kit was sent. A kit can be sent to a person (e.g., a surgeon), for example, after surgery, for processing a second biopsy.

C. Performing a Biopsy and Submitting a Sample

Any biopsy technique used by those skilled in the art can be used for isolating a sample from a subject. The biopsy can be an open biopsy, in which general anesthesia is used or a closed biopsy, in which a smaller cut is made than in an open biopsy. The biopsy can be a core or incisional biopsy, in which part of the tissue is removed; an excisional biopsy, in which attempts to remove an entire lesion are made; or a needle aspiration (percutaneous) biopsy (fine needle aspiration biopsy), in which a sample of tissue or fluid is removed with a needle. The needle can be a thin, hollow needle, and it can be inserted into a mass to extract cells from the mass. Tissue can be obtained by lumpectomy or mastectomy. Tissue can be obtained by colectomy (e.g., a total colectomy or partial colectomy). Tissue can be obtained by a prostatectomy.

The biopsy can be performed by a health care provider, including, for example, a physician, physician assistant, nurse, veterinarian, dentist, chiropractor, paramedic, dermatologist, oncologist, gastroenterologist, or surgeon.

The biopsy can be processed. For example, the biopsy can be preserved by formalin-fixing and paraffin-embedding (FFPE) the tissue. The biopsy can be processed into smaller pieces. The biopsy can be treated to preserve RNA, e.g., with RNAlater® or RNASafer™. The biopsy can be stored on wet ice (approximately 4° C.), at room temperature (approximately 25° C.), stored at approximately −20° C., or at approximately −80° C., e.g., stored on dry ice, or frozen in liquid nitrogen or a dry ice/alcohol slurry. The tissue can be frozen within 0.5, 1, 5, 10, 15, 30, 60, 120, or 240 minutes of surgical resection. Fixative agents that can be used on the biopsy tissue include, for example, methanol-acetone, Carnoy's fixative (60% ethanol, 30% chloroform, 10% glacial acetic acid), Bouin's fixative, ethanol, acetone, formalin, methacam (substitute 60% methanol for the ethanol in Carnoy), UMFIX (universal molecular fixative), Omnifix, and FINEfix.

The sample can be one or more cells or tissue from, e.g., liver, lung, colon, pancreas, bladder, brain, breast, cervix, esophagus, eye, gallbladder, kidney, stomach, ovary, penis, prostate, pituitary, salivary gland, skin, testicle, uterus, and vagina. The sample can be, for example, blood or urine. The sample can contain nucleic acid, for example, genomic DNA, amplified genomic DNA, cDNA, amplified cDNA, RNA, amplified RNA, unspliced RNA, spliced RNA, messenger RNA, or microRNA. The sample can be a cell-free sample that contains nucleic acid, for example, DNA or RNA.

The sample can be a bone marrow core or clot. The clot can be decalcified. The sample can be one or more unstained slides from an FFPE block. The one or more slides can be air-dried (unbaked). The slides can be charged or uncharged. The sample can be a pleural/ascitic fluid. The pleural/ascitic fluid can be formalin fixed and parafilm-embedded in a cell block.

The sample can contain greater than 10% tumor, greater than 15% tumor, greater than 20% tumor, greater than 25% tumor, greater than 30% tumor, greater than 35% tumor, greater than 40% tumor, greater than 45% tumor, greater than 50% tumor, greater than 55% tumor, greater than 60% tumor, greater than 65% tumor, greater than 70% tumor, greater than 75% tumor, greater than 80% tumor, greater than 85% tumor, greater than 90% tumor, greater than 95% tumor, or greater than 99% tumor. The sample can contain 100% tumor. The type of sample submitted to a personalized medicine business can depend on the type of molecular analysis to be performed on the sample (e.g., DNA microarray, DNA sequencing, IHC).

The sample (e.g., biopsy) can be obtained by a personalized medicine business by receiving it from, for example, the health care provider who removed the sample from the subject. The sample can be obtained by a personalized medicine business through a mail or delivery service; for example, a physician can perform a tumor biopsy and arrange to send the tumor biopsy. Parafilm-embedded tissue can be sent to a personalized medicine business in an envelope. The paraffin embedded sample can be a diagnostic primary biopsy. A fresh-frozen sample can be sent to a personalized medicine business in a container, and the container can include dry ice. A blood sample can be sent in a container, e.g., a tube. A sample can be sent in a container with an ice-water mixture. A sample can be sent to a personalized medicine business in a container provided by the personalized medicine business.

One or more employees of a personalized medicine business can review the samples that are obtained by the personalized medicine business. The samples can be reviewed by a pathologist employed by the personalized medicine business. The personalized medicine business can request that one or more additional samples be sent to the personalized medicine business, for example, after receiving an initial sample from the subject.

D. Purifying Cancer Cells

The methods of the provided invention can include a step in which primary tumor cells are separated/purified from non-tumor cells in a sample, e.g., a biopsy sample. Any technique used by those skilled in the art can be appropriate for isolating primary tumor cells from non-tumor cells in the tumor biopsy. For example, the tumor cells can be isolated using techniques that include optical cell sorting, flow-cytometry, flow-sorting, fluorescence activated cell sorting (FACS), magnetic cell sorting (MACS; e.g., using antibody coated magnetic particles), size-based separation (e.g., using a sieve, an array of obstacles, a filter), sorting in a microfluidics device, antibody-based separation, sedimentation, affinity adsorption, affinity extraction, or density gradient centrifugation. Fresh-frozen or FFPE samples can be used for flow-sorting. Sorting can be based on cell size, morphology, or intracellular or extracellular markers. Methods for isolating or sorting tumor cells are described, for example, in Nagrath S. et al. (2007) Nature 450:1235-1239; U.S. Pat. Nos. 6,008,002, 7,232,653, and 7,332,288; PCT Publication No. WO2008157220A1; and US Patent Application Nos. US20080138805A1 and US20090186065; and Rosenberg R. et al. (2002) Cytometry 49:150-158, each of which is herein incorporated by reference in their entireties.

Fluorescence-activated cell sorting (FACS) uses light scattering and fluorescent characteristics to sort cells. A fluorescent property can be imparted on a cell using, e.g., nucleic acid probes or antibodies conjugated to a fluorescent dye. A cell suspension can form a stream of flowing liquid. The stream of cells forms drops that contain approximately one cell per drop. Before the stream forms drops, a fluorescent characteristic of each cell is measured. A charge is placed on an electrical charging ring prior to fluorescence intensity measurement and the opposite charge is carried on the drop as it breaks from the stream. The charged drops pass through two high voltage deflection plates that divert drops into different containers based upon their charge. The charge can be directly applied to the stream and the drop breaking off retains the charge of the same sign as the stream. The stream is then returned to neutral after the drop breaks off.

Direct or indirect immunofluorescence can be used in FACS. In direct immunofluorescence, an antibody is directly conjugated to a fluorescent dye. In indirect immunofluorescence, the primary antibody is not labeled, and a secondary antibody is conjugated to a fluorescent dye.

Different types of cancer cells can be sorted based on one or more different molecular markers, and these markers can be on the surface of the cancer cells. Cells, e.g., circulating tumor cells, can be isolated from a sample, e.g., blood, using technology from, e.g., CELLective Dx Corporation.

A sample can be obtained from a subject, e.g., a colon cancer patient, by fine needle aspiration biopsy, the sample can be stored fresh-frozen, and the cancer cells in the sample can be isolated by flow-sorting.

Cancer cells can be purified by laser capture microdissection. In laser capture microdissection, a transparent transfer film is applied on the surface of a tissue section. Cells to be removed are identified using a microscope, and a near infrared (IR) laser diode is activated. The laser beam fuses the transfer film to the underlying cells. The film can then be removed with the desired cells attached. Fresh-frozen and paraffin embedded tissue may be used for laser capture microdissection.

Cancer cells can be purified using Panomics (Affymetrix®) Cancer Cell Isolation Kit (Catalog number CI0002, CI0004, or CI0010). Cancer cells can be isolated using CytoSelect™ Clonogenic Tumor Cell Isolation Kit (Catalog number CBA-155 or CBA-155-5) from Cell Biolabs, Inc.

A fee can be charged by a personalized medicine business in exchange for purifying cancer cells from a sample.

III. Molecular Markers

A. Techniques for Determining the Status of Molecular Markers

The methods of the provided invention can include analyzing a sample for the status of one or more molecular markers. The sample can be analyzed for one or more molecular markers that can include, for example, nucleic acids, including DNA and RNA, proteins, including antibodies, autoantibodies, and cell surface receptors, gene or protein expression profiles, carbohydrates, and lipids. The status of one or more molecular markers in the sample can be identified (determined) using techniques that include, for example, comparative genomic hybridization (CGH) or chromosomal microarray analysis (CMA), in which copy number changes of DNA in a tumor are detected, expression profiling, DNA microarray, high-density oligonucleotide microarray, whole-genome RNA expression array, peptide microarray, enzyme-linked immunosorbent assay (ELISA), genome sequencing, de novo sequencing, 454 sequencing, pyrosequencing, Helicos True Single Molecule Sequencing, SOLiD™ sequencing, SOLEXA sequencing, nanosequencing, chemical-sensitive field effect transistor (chemFET) array sequencing, polony sequencing, copy number variation (CNV) analysis sequencing, small nucleotide polymorphism (SNP) analysis, immunohistochemistry (IHC), immunoctyochemistry (ICC), mass spectrometry, tandem mass spectrometry, matrix-assisted laser desorption ionization time of flight mass spectrometry (MALDI-TOF MS), in-situ hybridization, fluorescent in-situ hybridization (FISH), chromogenic in-situ hybridization (CISH), silver in situ hybridization (SISH), polymerase chain reaction (PCR), digital PCR (dPCR), reverse transcription PCR, quantitative PCR (Q-PCR), single marker qPCR, real-time PCR, nCounter Analysis (Nanostring technology), Western blotting, Southern blotting, SDS-PAGE, gel electrophoresis, and Northern blotting.

The status of one or more molecular markers corresponding to genetic polymorphisms between members of a population can be detected by numerous methods well-established in the art e.g., PCR-based sequence specific amplification, restriction fragment length polymorphisms (RFLPs), isozyme markers, northern analysis, allele specific hybridization (ASH), array based hybridization, amplified variable sequences of the genome, self-sustained sequence replication, simple sequence repeat (SSR), single nucleotide polymorphism (SNP), random amplified polymorphic DNA ("RAPD") or amplified fragment length polymorphisms (AFLP).

Techniques for determining the status of one or more molecular markers can use hybridization of a probe nucleic acid to nucleic acids corresponding to the molecular marker (e.g., amplified nucleic acids produced using genomic DNA as a template). Hybridization formats for allele detection can include, for example, solution phase, solid phase, mixed phase, or in situ hybridization assays. A guide to the hybridization of nucleic acids is found in Tijssen (1993) Laboratory Techniques in Biochemistry and Molecular Biology—Hybridization with Nucleic Acid Probes Elsevier, N.Y.

The status of a molecular marker can include, for example, gene expression level (e.g., messenger RNA level)

or protein expression level. The expression level can be, for example, higher than normal, normal, or below normal. The status of a molecular marker can include absence of a mutation (e.g., wild-type) or presence of one or more mutations (e.g., de novo mutation, nonsense mutation, missense mutation, silent mutation, frameshift mutation, insertion, substitution, point mutation, single nucleotide polymorphism (SNP), deletion, rearrangement, amplification, chromosomal translocation, interstitial deletion, chromosomal inversion, loss of heterozygosity, loss of function, gain of function, dominant negative, or lethal); nucleic acid modification (e.g., methylation); or presence or absence of a post-translational modification on a protein (e.g., acetylation, alkylation, amidation, biotinylation, glutamylation, glycosylation, glycation, glycylation, hydroxylation, iodination, isoprenylation, lipoylation, prenylation, myristoylation, farnesylation, geranylgeranylation, ADP-ribosylation, oxdiation, palmitoylation, pegylation, phosphatidylinositol addition, phosphopantetheinylation, phosphorylation, polysialyation, pyroglutamate formation, arginylation, sulfation, or selenoylation).

B. De Novo DNA Sequencing Techniques

The methods of the provided invention can use de novo sequencing to determine the status of one or more molecular markers in a sample, e.g., a sample from a colon cancer patient. De novo sequencing techniques include, for example, Helicos True Single Molecule Sequencing (tSMS) (Harris T. D. et al. (2008) *Science* 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to flow cell surface. The templates can be at a density of about 100 million templates/cm². The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step.

Another example of a de novo DNA sequencing technique that can be used to determine the status of one or more molecular markers in a sample is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a de novo DNA sequencing technique that can be used to determine the status of one or more molecular markers in a sample is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a de novo sequencing technology that can be used to determine the status of one or more molecular markers in a sample is SOLEXA sequencing (Illumina). SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of de novo sequencing technology that can be used to determine the status of one or more molecular markers in a sample is the single molecule, real-time (SMRT™) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off Detection of the corresponding fluorescence of the dye indicates which base was incorporated. The process is repeated.

Another example of de novo sequencing that can be used to determine the status of one or more molecular markers in a sample is nanopore sequencing (Soni G V and Meller A. (2007) *Clin Chem* 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of de novo sequencing that can be used to determine the status of one or more molecular markers in a sample involves using a chemical-sensitive field effect transistor (chemFET) array to sequence DNA (as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Any one of the de novo sequencing techniques described herein can be used to determine the status of one or more molecular markers in the methods of the provided invention.

Figure 9:
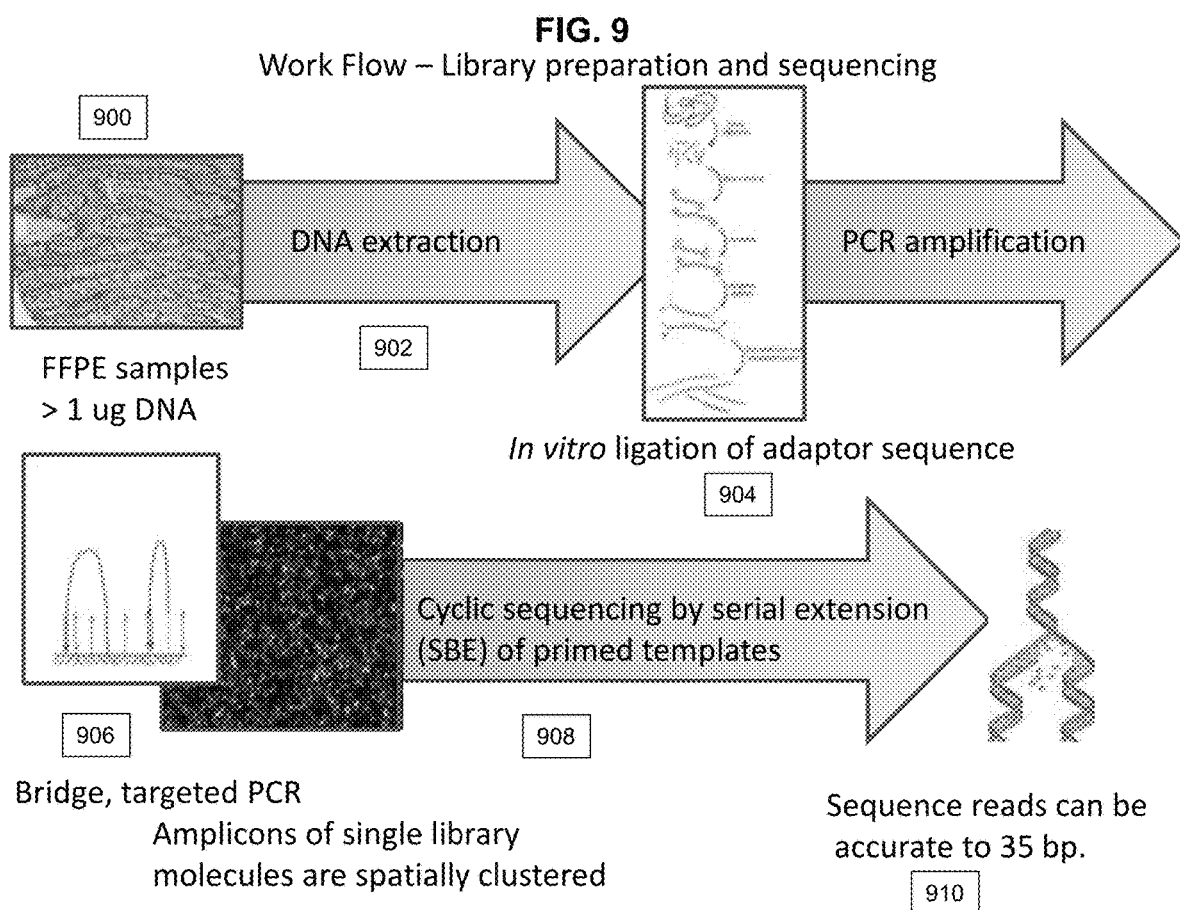
FIG. 9 illustrates a process for sequencing DNA from FFPE samples.

DNA can be extracted from an FFPE sample and the DNA can be bridge amplified and sequenced. The sequences generated can be used to determine the status (e.g., wild-type or mutant) of one or more molecular markers (e.g., genes). An example of the process is illustrated in FIG. 9. Greater than 1 µg of DNA can be extracted (902) from an FFPE sample (900). Adaptor sequences can be ligated to the DNA in an in vitro ligation reaction (904). The extracted DNA can be bridge amplified to generate a library of single molecules that are spatially clustered (906). The bridge amplified DNA can then be sequenced by serial extension of primed templates (908). The accuracy of sequence reads can be up to 35 bp (910). The sequences can be used to determine the status (e.g., wild-type or mutant) of one or more genes in the sample.

DNA from an FFPE tissue sample, including a historic FFPE tissue sample, can be sequenced, for example using 454 sequencing, to determine the status of one or more molecular markers (Thomas R K et al. (2006) *Nature Medicine* 12:852-855). Sequences from one or more historic samples can be compared to sequences from a sample from a subject, e.g., a cancer patient. The status of one or more molecular markers in a historic sample can be correlated with one or more treatment outcomes, and the correlation of a treatment outcome with molecular marker status in one or more historic samples can be used to predict treatment outcomes for the subject, e.g., a cancer patient. These predictions can be the basis for determining whether or not to recommend a drug treatment option to the subject.

The status of one or more molecular markers can be determined by de novo DNA sequencing of samples from cancer patients, and cancer patients can be grouped based on the status of the one or more molecular markers. For instance, cancer patients with wild-type Kras can be grouped together, and patients with mutant Kras can be grouped together. The survival of untreated patients in each group can be followed over time, and patient survival can be plotted to generate a Kaplan-Meier curve. A Kaplan-Meier plot can be used to illustrate the fraction of patients alive after a certain amount of time. The survival of cancer patients in each group after treatment with a drug can be followed over time, and patient survival can be plotted to generate a Kaplan-Meier curve. Analysis of a previously generated Kaplan-Meier curve can be used to recommend one or more drug treatment options to a subject (e.g., a cancer patient), based on the status of one or more molecular markers in a sample from the subject (e.g., a cancer patient).

C. Business Considerations

A personalized medicine business can outsource or sub-contract the determining of the status of one or more molecular markers to a Clinical Laboratory Improvement Amendments (CLIA) certified laboratory. The personalized medicine business can outsource or sub-contract the determining of the status of one or more molecular markers, for example, whole genome analysis, to another company, for example, Illumia® or Affymetrix®. Mass spectrometry (e.g., matrix-assisted laser desorption ionization time of flight mass spectrometry (MALDI-TOF MS)) can be performed at, e.g., Biodesix. Only a portion of the whole genome analysis data can be reported to a patient and/or health care provider, and the rest of the data can be stored by the personalized medicine business. The stored data can be sent to the subject and/or health care provider at a later date.

Other in vitro or in vivo tests can be performed on a sample. The personalized medicine business can outsource or sub-contract another company to perform the in vitro or in vivo tests.

A fee can be charged by the personalized medicine business in exchange for performing the techniques and/or identifying (determining the status of) one or more molecular markers. The molecular marker analysis can be performed by one or more employees of the personalized medicine business, for example, one or more laboratory technicians.

IV. Drug Metabolism

The methods of the provided invention can include analyzing a sample from a subject for the status of one more markers related to drug absorption, distribution, metabolism, and excretion. The sample to be analyzed can be, for example, a tumor biopsy, blood, cheek (buccal) swab, or other fluid or tissue taken from the subject. Any test known by those skilled in the art to investigate drug absorption, distribution, metabolism, or excretion genes can be used. For example, the Affymetrix® Drug Metabolizing Enzymes and Transporters (DMET)—Early Access Solution can be used to analyze drug metabolism biomarkers. CYP450 status can be assessed using the Roche® AmpliChip CYP450

Test, which tests for gene variations in CYP2D6 and CYP2C19. The Human1M BeadChip from Illumina®, Human1M-Duo DNA Analysis BeadChip from Illumina®, and HumanExon510S-Duo DNA Analysis BeadChip from Illumina® can be used to identify SNPs in ADME (absorption, distribution, metabolism, and excretion) genes. The status of ADME associated genes can be investigated using DTEx™ Gene Expression Analysis from NoAb BioDiscoveries.

A sample can be analyzed for one or more SNPs in the UGT1A1 gene, which encodes UDP-glucuronosyltransferase. Identification of UGT1A1 promoter polymorphisms can be used to predict the toxicity of treatment with CPT-111 (irinotecan). Irinotecan is a topoisomerase I inhibitor that can be used for treating colon cancer. Irinotecan is activated by hydrolysis to SN-38, and SN-38 is inactivated by glucuronidation by UGT1A1. Subjects with the *28 variant ((TA)$_7$ allele) of UGT1A1 express reduced amounts of UGT1A1 in their liver, and they do not clear irinotecan as rapidly as others. This can correspond to increased rates of severe diarrhea and neutropenia. Patients with polymorphisms in the UGT1A1 gene (e.g., *28 variant) have been recommended by the FDA to receive reduced doses of irinotecan. If a sample from a subject, e.g., a cancer patient, has a *28 variant UGT1A1 allele, a recommendation can be made in a report to treat the subject with a reduced amount of irinotecan.

A fee can be charged by the personalized medicine business for analyzing one or more molecular markers related to absorption, distribution, metabolism, or excretion of one or more drugs. The analysis of one or more molecular markers related to drug absorption, distribution, metabolism, or excretion can be performed by one or more laboratory technicians employed by the personalized medicine business.

Stratifying drug treatment options and annotating drug treatment options in a report regarding the use of a drug treatment option can be done based on the status of one or more molecular markers that regulate drug absorption, distribution, metabolism, or excretion in a sample from a subject.

V. Stratifying Drug Treatment Options

The methods of the provided invention can include using the status of one or more molecular markers identified in a sample to stratify (rank) drug treatment options for the subject from whom the sample was taken (target-drug approach). The stratifying of drug treatments can be based on scientific information regarding the molecular markers. For example, the scientific information can be data from one or more studies published in one or more scientific journals (e.g., *New England Journal of Medicine* (*NEJM*), *Lancet*, etc.). The scientific information can be data provided in a commercial database (e.g., data stored in a database provided by Ingenuity® Systems). One or more pieces of scientific information can be used to stratify the treatments.

A. Classes of Drugs

Drug treatment options can be stratified into classes based on the status of one or more molecular markers in a sample. For example, a first class of drug treatment options can be those for which scientific information predicts a drug will be efficacious for a subject whose sample has one or more molecular markers of a particular status. Drugs in this first class can be a recommended drug treatment option for a subject.

A second class of drug treatment options can be those for which some scientific information predicts a drug will be efficacious for a subject with one or more molecular markers of a particular status, and some scientific information does not support use of the drug for the subject, based on one or more molecular markers of a particular status in a sample from a subject. For example, a sample may contain a marker whose status indicates the drug will be efficacious in the subject and another marker (e.g., a mutant version of a drug metabolism gene) that indicates the drug would also have a toxic affect on the subject. Up to 9 molecular markers in a sample from a patient can indicate that a drug is likely to be efficacious for treating a subject from whom the sample was taken, and one molecular marker, for instance a drug metabolism marker, can indicate that the drug would have a high level of toxicity in the subject.

This second class can also include drugs for which there is indirect scientific support for drug efficacy in a subject (e.g., the drug targets a protein that is in the same molecular pathway as a molecular marker in a sample). For example, a drug in this class could target a kinase that functions downstream of an overexpressed cell surface receptor that is known to be targeted by an efficacious drug. A drug in this second class can be a recommended drug treatment option for a subject.

A third class of drugs can be those for which scientific information indicates the drug will not be efficacious in the subject based on the status of one or more molecular markers in a sample from the subject. For example, a drug that targets a cell surface receptor may not display efficacy if a downstream kinase is mutated. It can be recommended that a subject not be treated with a drug in this third class.

Figure 7:
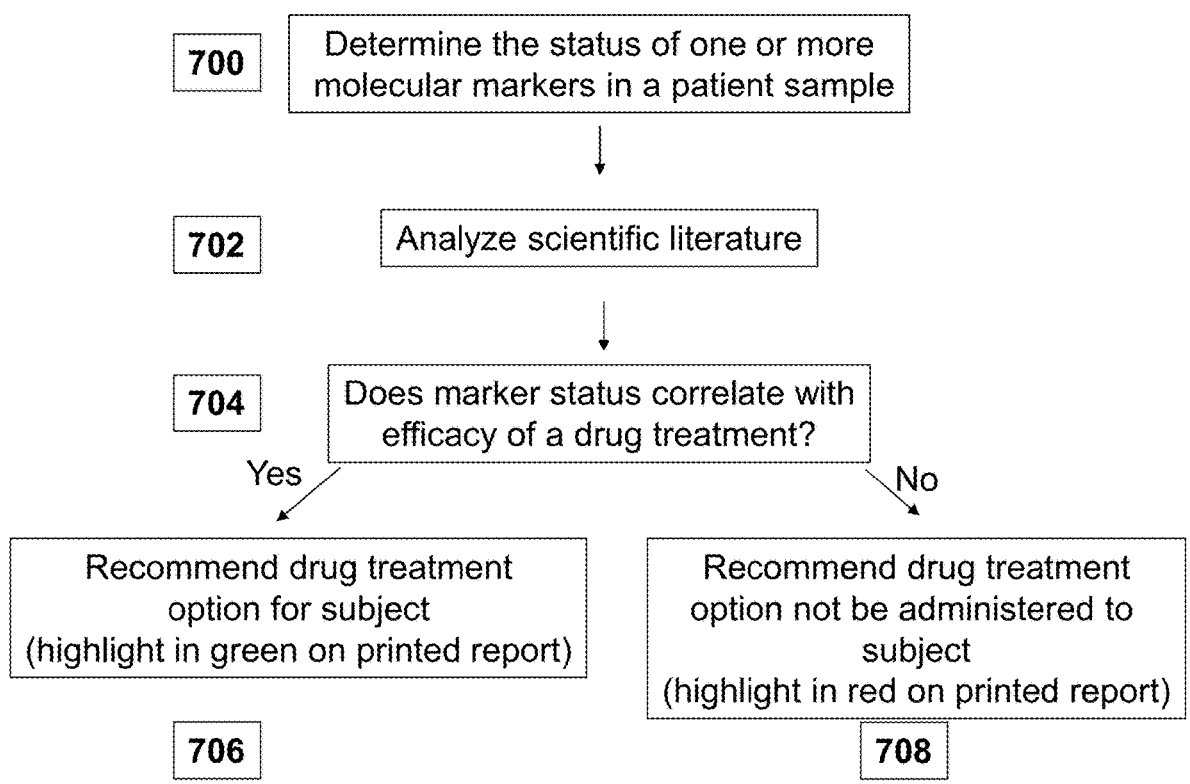
FIG. 7 shows an algorithm for determining which drug treatment options to recommend to a subject with one or more molecular markers of a particular status.

The drug treatment options can be stratified using an algorithm-based approach. An example of an algorithm for selecting a marker is shown in FIG. 7. The status of one or more molecular markers in a patient sample is determined (700). The scientific literature is analyzed for information related to the status of the molecular marker and the efficacy of one or more different drugs (702, 704). If the status of a molecular marker correlates with efficacy of a drug, then a recommendation can be made to treat the subject with that drug (706). If the status of a molecular marker does not correlate with efficacy of a drug, then a recommendation can be made not to treat a subject with the drug (708). A computer and computer readable medium can be used to stratify the drug treatment options.

A list of stratified drug treatment options can be presented in the form of a report. The stratification of drug treatment options can be indicated by color coding. For example, drugs in the first class can be color coded in green, drugs in the second class can be color coded in yellow, and drugs in the third class can be color coded in red.

The recommendation of a drug treatment option for a subject can be based on the stage of the cancer of the subject, e.g., a late stage cancer. Drug treatment options can also be stratified based on other factors, e.g., the type of cancer, age of the subject, status of drug metabolism genes (genes involved in absorption, distribution, metabolism, and excretion), efficacy of other drugs the patient has received, clinical information regarding the subject, and family medical history.

A fee can be charged by the personalized medicine business in exchange for stratifying the drug treatment options. The drug treatment options can be stratified by one or more employees of the personalized medicine business, for example, a molecular pathologist and research nurse.

B. Examples of Molecular Marker/Drug Relationships and Drugs Used for Cancer Treatment Drug treatment options can be stratified based on a relationship between the status of one or more molecular markers in the sample and the efficacy of a drug treatment used on other subjects with the one or more molecular markers of a particular status. The scientific literature contains multiple examples of drugs that have efficacy in treating subjects with tumors with certain molecular markers.

The status of c-kit (also known as CD117, KIT, PBT, SCFR) in a sample from a subject can be determined by, e.g., expression or DNA sequencing, and can be used to determine whether to recommend imatinib mesylate (Gleevec) as a drug treatment option for the subject, e.g., a gastrointestinal tumor patient with a metastatic and/or unresectable malignant tumor (NCCN Clinical Practice Guidelines in Oncology; Henrich M C et al. (2003) *J. Clin. Oncol.* 21:4342-4349). C-kit is a receptor for cytokine stem cell factor (SCF, steel factor, or c-kit ligand). When c-kit binds to SCF it forms a dimer which activates signaling through second messengers. Signaling through c-kit plays a role in cell survival, proliferation, and differentiation. Imatinib mesylate (Gleevec) is an inhibitor of receptor tyrosine kinases. If a sample from a subject with a metastatic and/or unresectable malignant gastrointestinal stromal tumor expresses c-kit or c-kit with activating mutations, a recommendation can be made to treat the subject with imatinib mesylate (Gleevec). If a sample from a subject does not express c-kit or c-kit with activating mutations, a recommendation can be made to not treat the subject with imatinib mesylate (Gleevec). Imatinib mesylate (Gleevec) is efficacious in GIST patients with activating mutations in the juxtamembrane (JM) domain of c-kit.

The presence of Bcr-Abl in a sample from a subject can be used to determine whether to recommend imatinib mesylate (Gleevec) as a drug treatment option to the subject, e.g., a chronic myeloid leukemia (CML) patient. For example, a patient with CML with the Philadelphia chromosome (Philadelphia translocation) that produces the Bcr-Abl protein, a tyrosine kinase, can be recommended to be treated with imatinib mesylate (Gleevec). Approximately 95% of people with CML have the Philadelphia chromosome. Imatinib mesylate (Gleevec) can be recommended as an initial therapy for a CML patient. Imatinib mesylate (Gleevec) can be recommended for use while a CML patient is in the first phase of CML (the chronic phase) (Kantarjian H. et al. (2002) *NEJM* 356:645-652). Imatinib mesylate (Gleevec) can be recommended to a CML patient if interferon alpha therapy fails (Druker B J et al. (2001) *NEJM* 344:1031-1037).

The status of PDGFR in a sample can be used to determine whether to recommend imatinib mesylate (Gleevec) as a drug treatment option to a subject, e.g., a cancer patient. Cancer cells overexpressing platelet derived growth factor receptor (PDGFR), a tyrosine kinase, or with activating mutations in PDGFR can be targeted with imatinib mesylate (Gleevec) (Heinrich M C et al. (2003) *J Clin. Oncol.* 21:4342-4349). If a sample from a subject overexpresses PDGFR, or expresses PDGFR with activating mutations, a recommendation can be made to treat the subject with imatinib mesylate (Gleevec). If a sample from a subject does not overexpress PDGFR, a recommendation can be made to not treat the subject with imatinib mesylate (Gleevec).

A subject with renal cell carinoma (RCC) or imatinib-resistant GIST that expresses the marker PDGFR can be treated with Sutent (Sunitib or SU11248), a receptor tyrosine kinase inhibitor. If a sample from a subject with RCC or imatinib-resistant GIST expresses PDGFR, a recommendation can be made to treat the subject with Sutent (Sunitib).

The status of secreted protein acidic and rich in cysteine (SPARC; also known as ON, osteonectin) in a sample can be used to determine whether to recommend Abraxane as a drug treatment option for a subject, e.g., a metastatic breast cancer patient. SPARC is a matrix-associated protein that can elicit alterations in cell shape, inhibit cell-cycle progression, and influence the synthesis of the extracellular matrix (ECM). Pre-clinical studies indicate that a patient with a tumor expressing SPARC, which binds albumin, can be targeted with a paclitaxel albumin-stabilized nanoparticle formulation (Abraxane) and that Abranxe may have a higher level of efficacy in these patients compared with patients whose tumors do not express SPARC. If a sample from a subject expresses SPARC, a recommendation can be made to treat the subject with Abraxane. If a sample from a subject does not express SPARC, a recommendation can be made to not treat the subject with Abraxane. Abraxane is indicated for the treatment of breast cancer after failure of combination chemotherapy for metastatic disease or relapse within 6 months of adjuvant chemotherapy.

The status of HSP90 (also known as HSPN; LAP2; HSP86; HSPC1; HSPCA; Hsp89; HSP89A; HSP90A; HSP90N; HSPCAL1; HSPCAL4; FLJ31884; HSP90AA1) in a sample can be used to determine whether to recommend CNF2024 (BIIB021) as a drug treatment option for a subject. Hsp90 is a molecular chaperone that can facilitate the maturation and stabilization of mutated, overexpressed and constitutively or persistently active oncoproteins (Taldone T, *Curr Opin Pharmacol.* (2008) August; 8(4):370-374). A patient with GIST expressing heat shock protein 90 (HSP90) can be targeted with CNF2024 (BIIB021), an oral inhibitor of HSP90. If a sample from a subject expresses HSP90, a recommendation can be made to treat the subject with CNF2024 (BIIB021). If a sample from a subject does not express HSP90, a recommendation can be made to not treat the subject with CNF2024 (BIIB021).

The status of MGMT (O-6-methylguanine-DNA methyltransferase) promoter methylation in a sample can be used to determine whether to recommend temozolomide (Temodar, Temodal) as a drug treatment option for a subject, e.g., a glioblastoma patient. The MGMT gene is located on chromosome 10q26. MGMT encodes a DNA-repair protein that removes alkyl groups from the O6 position of guanine, a site of DNA alkylation. O6-methylguanine lesions induced by chemotherapy that remain unrepaired can trigger cytotoxicity and apoptosis. High levels of MGMT activity in cancer cells can reduce the therapeutic effect of an alkylating agent. Loss of MGMT expression and reduced DNA-repair activity are associated with epigenetic silencing of the MGMT gene by promoter methylation. Temozolomide (Temodar, Temodal) is an alkylating agent. Data suggest that MGMT promoter methylation is associated with a favorable outcome after temozolomide chemotherapy in patients with recently diagnosed glioblastoma (Hegi M E et al. (2005) *NEJM* 352:997-1003). If a sample from a subject has MGMT promoter methylation, a recommendation can be made to treat the subject with temozolomide. If a sample from a subject does not have MGMT promoter methylation, a recommendation can be made to not treat the subject with temozolomide.

The status of HER2 (also known as ERBB2, NEU, NGL, TKR1, CD340, HER-2, HER-2/neu) in a sample can be determined by, e.g., IHC, PCR, SISH/CISH/FISH, and can be used to determine whether to recommend trastuzumab (Herceptin) as a drug treatment option for a subject, e.g., a breast cancer patient. HER2 is an epidermal growth factor receptor. HER2 can bind to other ligand-bound EGF receptor family members to form a heterodimer. This binding can stabilize ligand binding and enhance kinase-mediated activation of downstream signaling pathways, such as those involving mitogen-activated protein kinase and phosphatidylinositol-3 kinase. Amplification and/or overexpression of HER2 is reported in numerous cancers, including breast and ovarian tumors. Breast cancer patients that overexpress the HER2 receptor can be treated with trastuzumab (Herceptin), a monoclonal antibody that can bind to the domain IV of the extracellular segment of HER2. Herceptin is approved for adjuvant treatment of HER2-overexpressing metastatic breast cancer. As a single agent, Herceptin is approved for treatment of HER2-overexpressing breast cancer in patients who have received one or more chemotherapy regimens for metastatic disease. If a sample from a subject (e.g., a breast cancer patient) overexpresses HER2, a recommendation can be made to treat the subject with trastuzumab (Herceptin). If a sample from a subject (e.g., a breast cancer patient) does not overexpress HER2, a recommendation can be made to not treat the subject with trastuzumab (Herceptin).

The status of human epidermal growth factor receptor 1 (also known as HER1, EGFR, ERBB, mENA, ERBB1, PIG61) in a sample can be used to determine whether to recommend Erlotinib (Tarceva) as a drug treatment option for a subject. EGFR is a transmembrane glycoprotein receptor for epidermal growth factor family members. Binding of the EGFR to a ligand induces receptor dimerization and tyrosine autophosphorylation and leads to cell proliferation. Mutations in HER1 are associated with lung cancer. Erlotinib (Tarceva) binds to the ATP binding site of the EGFR tyrosine kinase. Tarceva monotherapy is indicated for the treatment of patients with locally advanced or metastatic non-small cell lung cancer after failure of at least one prior chemotherapy regimen. Tarceva in combination with gemcitabine is indicated for the first-line treatment of patients with locally advanced, unresectable or metastatic pancreatic cancer. Erlotinib (Tarceva) is efficacious in patients with pancreatic cancer and non-small cell lung cancer that are positive by immunohistochemistry (IHC) for EGFR. If a sample from a subject expresses EGFR, erlotinib (Tarceva) can be recommended as a drug treatment option for the subject. If a sample from a subject does not express EGFR, a recommendation can be made to not treat the subject with erlotinib (Tarceva).

The status of vascular endothelial growth factor (VEGF) can be used to determine whether to recommend Bevacizumab (Avastin) as a drug treatment option. VEGF is a glycosylated mitogen that can act on endothelial cells. VEGF can mediate increased vascular permeability, inducing angiogenesis, vasculogenesis and endothelial cell growth, promote cell migration, and inhibit apoptosis. Bevacizumab (Avastin) is a recombinant humanized monoclonal antibody directed to VEGF. Bevacizumab (Avastin) can block tumor growth by inhibiting the formation of new blood vessels. Bevacizumab (Avastin) is indicated for first or second-line treatment of patients with metastatic carcinoma of the colon or rectum in combination with intravenous 5-fluorouracil-based chemotherapy. Bevacizumab (Avastin) is also indicated for the first-line treatment of unresectable, locally advanced, recurrent or metastatic non-squamous non-small cell lung cancer in combination with carboplatin and paclitaxel. Bevacizumab (Avastin) is also indicated for the treatment of patients who have not received chemotherapy for metastatic HER2-negative breast cancer in combination with paclitaxel. Bevacizumab (Avastin) is indicated for the treatment of metastatic renal cell carcinoma in combination with interferon alpha. If a sample from a subject expresses VEGF, Bevacizumab (Avastin) can be recommended as a drug treatment option. If a sample from a subject does not express VEGF, a recommendation can be made to not treat the subject with Bevacizumab (Avastin).

The status of ER (also known as estrogen receptor; ESR; Era; ESRA; NR3A1; DKFZp686N23123; ESR1) in a sample from a subject can be determined by, e.g., IHC, and can be used to determine whether to recommend hormonal therapeutics to the subject, e.g., a subject with breast cancer. ER is a ligand-activated transcription factor that includes domains for hormone binding, DNA binding, and activation of transcription. ER can localize to the nucleus and can form a homodimer or a heterodimer with estrogen receptor 2. If a sample, e.g., a biopsy from a breast cancer patient, is analyzed by IHC and receives a score that establishes it as ER-positive, a recommendation can be made to treat the subject with hormonal therapeutics. If the sample from a subject (e.g., a breast cancer patient) is determined to be ER-negative, a recommendation can be made to not treat the subject with hormonal therapeutics.

The status of PR (also known as progesterone receptor; NR3C3; PGR) in a sample from a subject can be determined by, e.g., IHC, and can be used to determine whether to recommend hormonal therapeutics to the subject, e.g., a subject with breast cancer. PR is a member of the steroid receptor superfamily and mediates the physiological effects of progesterone. If a sample, e.g., a biopsy from a breast cancer patient, is analyzed by IHC and receives a score that establishes it as PR-positive, a recommendation can be made to treat the subject with hormonal therapeutics. If the sample from a subject (e.g., a breast cancer patient) is determined to be PR-negative (by, e.g., IHC), a recommendation can be made to not treat the subject with hormonal therapeutics.

The expression status of 21 genes in a sample from a subject (e.g., a breast cancer patient) can be determined using the Oncotype Dx assay (Genomic Health Inc.), which involves reverse transcription followed by RT-PCR of FFPE samples from primary breast cancer. The levels of expression are used to calculate an RS (Recurrence Score®), which can be used to assign a patient to a treatment group. The score generated from the analysis can be used to determine whether to recommend tamoxifen as a drug treatment option for a breast cancer patient. Tamoxifen is a selective estrogen receptor modulator (SERM). The Oncotype Dx test can be used after surgery (e.g., lumpectomy or mastectomy) but before a decision on adjuvant therapy is made.

The status of the PAM 50 expression signature in sample from a subject can be determined by, e.g., RT-PCR, and can be used to determine whether to recommend endocrine therapy for the subject, e.g., a breast cancer patient (Parker J S et al. (2009) *J Clin Oncol.* 27:1160-1167). The 50-gene PAM50 subtype predictor can be used to assign intrinsic subtypes to tumor samples and can be used to assess the likelihood of efficacy from neoadjuvant chemotherapy.

The status of vras and Kras in a sample from a subject can be used to determine whether to recommend bevacizumab (Avastin) as a drug treatment option to the subject, e.g., a colon cancer patient or a patient with metastatic colon cancer. (Grothey A and Turja J H (2008) cme.medscape-.com/viewarticle/577606).

Capecitabine (Xeloda) can be recommended as an adjuvant to a subject with colorectal cancer Stage III (Dukes' C) colon cancer (Twelves C. et al. (2005) *NEJM* 352:2696-2704) or as a first-line monotherapy for metastatic colorectal cancer. Capecitabine (Xeloda) is a prodrug that can be converted to 5-fluorouracil (5-FU) in a tumor. 5-FU inhibits DNA synthesis, thereby slowing tumor growth.

The status of a VeriStrat® (Biodesix) serum protein signature in a sample from a subject can be determined by, e.g., matrix-assisted laser desorption ionization time of flight mass spectrometry (MALDI-TOF MS), and can be used to determine whether to recommend cetuximab (Erbitux) as a drug treatment option for the subject, e.g., a colon cancer patient. The VeriStrat® test can predict the response to EGFR tyrosine kinase inhibitors (e.g., gefitinib or erlotinib) for patients with non-small cell lung cancer (NSCLC), and can be used to determine whether to recommend erlobtinib (Tarceva) or gefitinib (Iressa) to a subject, e.g., a metastatic lung cancer patient, non-small-cell lung cancer patient, adenocarinoma (ADC) patient, or squamous cell carcinoma (SCC) patient. Erlotinib (Tarceva) can target the epidermal growth factor receptor (EGFR) tyrosine kinase.

The status of EGFR expression in a sample from a subject can be used to determine whether to recommend cetuximab (Erbitux) as a drug treatment option for a subject, e.g., a colon cancer patient with an irinotecan resistant tumor (irinotecan (Camptosar) is a topoisomerase 1 inhibitor). For example, if a sample from a subject is determined to be an EGFR-expressing, metastatic colorectal carcinoma and the subject is refractory to irinotecan-based chemotherapy, a recommendation can be made to treat the subject with cetuximab (Erbitux).

The status of TOPO1 (also known as DNA topoisomerase; TOPI; TOP1) expression in a sample from a subject can be determined by, e.g., IHC, and can be used to determine whether to recommend fluorouracil (5-FU; F5U; Adrucil) with or without irinotecan or oxaliplatin for the subject, e.g., a colon cancer patient (Braun M. S. et al. (2008) *J Clin Oncol.* 26:2690-2698). TOPO1 can alter the topologic states of DNA by catalyzing the transient breaking and rejoining of a single strand of DNA which allows the strands to pass through one another. Fluorouracil (Adrucil) is a pyrimidine analog that can act as an inhibitor of thymidylate synthase, which makes thymidine for DNA replication. If a biopsy from a colon cancer patient is determined to have low TOPO1 expression by, e.g., IHC, 5-FU (Adrucil) can be recommended as a drug treatment option without irinotecan or oxaliplatin. If a biopsy from a colon cancer patient is determined to have moderate or high TOPO1 expression by, e.g., IHC, 5-FU (Adrucil) treatment with irinotecan or oxaliplatin can be recommended as a drug treatment option for the colon cancer patient.

The status of TOPO1 in a sample from a subject can be used to determine whether to recommend irinotecan (Camptosar) as a drug treatment option for the subject, e.g., a metastatic colon cancer patient. Irinotecan can be recommended to a metastatic colon cancer patient after recurrence of colon cancer or progression after 5-FU therapy.

The status of Phosphatase and Tensin Homolog (PTEN) in a sample from a subject can be used to determine whether to recommend cetuximab (Erbitux) or panitumumab (Vectibix) for the subject, e.g., a metastatic colorectal cancer patient (Frattini M. et al. (2007) *Br J Cancer* 97:1139-1145). PTEN can regulate the cell cycle. PTEN dephosphorylates phosphoinositide substrates. PTEN can regulate the intracellular levels of phosphatidylinositol-3,4,5-triphosphate and can act as a tumor suppressor by negatively regulating the Akt/PKB signalling pathway. If a sample from a subject expresses PTEN, a recommendation can be made to treat the subject with cetuximab (Erbitux) or panitumumab (Vectibix). If a sample from a subject does not express PTEN, a recommendation can be made to not treat the subject with cetuximab (Erbitux) or panitumumab (Vectibix).

The status of PIK3CA in a sample from a subject can be used to determine whether to recommend cetuximab (Erbitux) or panitumumab (Vectibix) for the subject, e.g., a metastatic colorectal cancer patient (Satore-Bianchi A et al. (2009) *Cancer Res* 69:1851-1857). PIK3CA encodes the 110 kDa catalytic subunit or phosphatidylinositol 3-kinase (which is also composed of an 85 kDa regulatory subunit). The catalytic subunit can phosphorylate PtdIns, PtdIns4P and PtdIns(4,5)P2. Membrane localization of PIK3CA inhibits PTEN and promotes AKT1 phosphorylation. If a sample from a subject has wild-type PIK3CA, a recommendation can be made to treat the subject with cetuximab (Erbitux) or panitumumab (Vectibix). If a sample from a subject has mutations in PIK3CA, a recommendation can be made to not treat the subject with cetuximab (Erbitux) or panitumumab (Vectibix).

Leucovorin (Wellcovorin, folinic acid) can be recommended as a drug treatment option for a subject, e.g., a colon cancer patient, in combination with 5-FU to prolong survival and promote palliative care. Leucovorin enhances the binding of 5-FU to thymidylate synthase and as a result prolongs the life span of 5-FU. This results in an anti-cancer effect of 5-FU.

Levamisole (Ergamisol) can be recommended as a drug treatment option for a subject, e.g., a patient with Dukes' Stage C colon cancer, in combination with 5-FU after surgical resection.

Oxaliplatin (Eloxatin) can be recommended as a drug treatment option for a subject, e.g., a patient with metastatic colon cancer, in combination with 5-FU and leucovorin (LV). Oxaliplatin (Eloxatin) is a platinum-based chemotherapy drug thought to inhibit DNA synthesis. Oxaliplatin (Eloxatin) used in combination with infusional 5-FU/LV is indicated for adjuvant treatment of stage III colon cancer patients who have undergone complete resection of the primary tumor and for treatment of advanced carcinoma of the colon or rectum.

Celecoxib (Celebrex) can be recommended as a drug treatment option for a subject, e.g., a colon cancer patient, a patient with familial adenomatous polyposis (FAP), a patient with colonic polyps, or a patient with colonic polyposis syndrome (FAPC) (Bertagnolli M M et al. (2006) *NEJM* 355:873-884; Arber N et al. (2006) *NEJM* 355:885-895). Celecoxib (Celebrex) is a nonsteroidal anti-inflammatory drug (NSAID) that is a specific COX-2 inhibitor.

The status of Kras (also known as v-Ki-ras2 Kirsten rat sarcoma viral oncogene homolog; NS3; KRAS1; KRAS2; RASK2; KI-RAS; C-K-RAS; K-RAS2A; K-RAS2B; K-RAS4A; K-RAS4B) in sample from a subject can be used to determine whether to recommend cetuximab (Erbitux) as a drug treatment option to the subject, e.g., a colon or rectal cancer patient with stage IV disease (COL-5, COL-9, COL-10) (NCCN Clinical Practice Guidelines in Oncology). Kras is a member of the small GTPase superfamily. Cetuximab (Erbitux), a monoclonal antibody that targets the epidermal growth factor receptor (EGFR), is efficacious in colorectal cancer patients with wild-type Kras (Karapetis C S et al. *NEJM* 359, 1757-1765). Cetuximab is indicated for treatment of locally or regionally advanced squamous cell carcinoma of the head and neck in combination with radiation therapy and recurrent or metastatic squamous cell carcinoma of the head and neck progressing after platinum-based therapy. If a sample from a subject has wild-type Kras, a recommendation can be made to treat the subject with cetuximab (Erbitux). If a sample from a subject has mutated Kras, a recommendation can be made to not treat the subject with cetuximab (Erbitux). If a sample from a subject has mutations in Kras in codon 12 or 13, a recommendation can be made to not treat the subject with cetuximab (Erbitux). A recommendation can be made to treat a subject, e.g., a colon or rectal cancer patient, with cetuximab (Erbitux) if the patient is not able to tolerate cetuximab and irinotecan.

Irinotecan (Camptosar) can be recommended as a drug treatment option for a subject, e.g., a colon or rectal cancer patient (NCCN Clinical Practice Guidelines in Oncology). Irinotecan (Camptosar) is indicated as a component of first-line therapy in combination with 5-fluorouracil and leucovorin for patients with metastatic carcinoma of the colon or rectum. Irinotecan (Camptosar) is also indicated for patients with metastatic carcinoma of the colon or rectum whose disease has recurred or progressed following initial fluorouracil-based therapy.

The status of epidermal growth factor receptor (EGFR) can be used to determine whether to recommend panitumumab (Vectibix) as a drug treatment option to a subject, e.g., a metastatic colon or rectal cancer patient. Panitumumab (Vectibix) is a human monoclonal antibody that can target epidermal growth factor receptor (EGFR). Panitumumab (Vectibix) is indicated as a single agent for the treatment of EGFR-expressing metastatic colorectal carcinoma (mCRC) with disease progression on or following fluoropyrimidine-, oxaliplatin-, and irinotecan-containing chemotherapy regimens. If a sample from a subject is determined to be an EGFR-expressing metastatic colorectal cancer, panitumumab (Vectibix) can be recommended as a drug treatment option for the subject. If a sample from a subject is not an EGFR-expressing metastatic colorectal cancer, a recommendation can be made to not treat the subject with panitumumab (Vectibix).

The status of Kras in a sample from a subject can be used to determine whether to recommend panitumumab (Vectibix) as a drug treatment option for the subject, e.g., a metastatic colon or rectal cancer patient with stage IV disease (COL-5, COL-9, COL-10) (NCCN Clinical Practice Guidelines in Oncology). If a metastatic colorectal cancer sample from a subject has wild-type Kras, a recommendation can be made to treat the subject with panitumumab (Vectibix). If a metastatic colorectal cancer sample from a subject has mutated Kras, a recommendation can be made not to treat the subject with panitumumab (Vectibix). If a metastatic colorectal cancer sample from a subject has mutations in Kras in codons 12 or 13, a recommendation can be made to not treat the subject with panitumumab (Vectibix). A recommendation can be made to treat a subject, e.g., a colon or rectal cancer patient, with panitumumab (Vectibix) if the subject is not able to tolerate cetuximab and irinotecan.

Mitomycin C (Mitozytrex) can be recommended as a drug treatment option for a subject, e.g., a gastrointestinal cancer patient, for palliative treatment of disseminated adenocarcinoma of the stomach or pancreas. Mitomycin C is a DNA crosslinker.

Cyclophosphamide (Neosar, Cytoxan) can be recommended as a drug treatment option for treating a subject, e.g., a lung cancer patient. Cyclophosphamide is a nitrogen mustard alkylating agent.

The status of Nrf2 (also known as nuclear factor (erythroid-derived 2)-like 2; NFE2L2) in a sample from a subject can be used to determine whether to recommend doxorubicin (Adriamycin) as a drug treatment option for the subject, e.g., a lung cancer patient (Wang et al. (2008) *Carcinogenesis* 29:1235-1243). Overexpression of Nrf2 resulted in enhanced resistance of cancer cells to doxorubicin (Adriamycin). NFE2, NFE2L1, and NFE2L2 comprise a family of human genes encoding basic leucine zipper (bZIP) transcription factors. Doxorubicin (Adriamycin) can intercalate DNA. If a sample from a subject overexpresses Nrf2, a recommendation can be made to not treat the subject with doxorubicin (Adriamycin). If a sample from a subject does not overexpress Nrf2, a recommendation can be made to treat the subject with doxorubicin (Adriamycin).

The status of DPD (also known as dihydropyrimidine dehydrogenase; DHP; DHPDHASE; MGC70799; MGC132008; DPYD) in a sample from a subject can be determined by, e.g., tandem mass spectrometry, and can be used to determine whether to recommend fluorouracil (5-FU) as a drug treatment option for the subject, e.g., a lung cancer patient or a non-small-cell lung cancer patient (Nakano J et al. (2006) *British Journal of Cancer* 95:607-615). DPD protein is a pyrimidine catabolic enzyme and the initial and rate-limiting factor in the pathway of uracil and thymidine catabolism. Mutations in DPD can result in dihydropyrimidine dehydrogenase deficiency, an error in pyrimidine metabolism associated with thymine-uraciluria and an increased risk of toxicity in cancer patients receiving 5-fluorouracil chemotherapy. If a sample from a subject is negative for DPD expression, a recommendation can be made to treat the subject with 5-FU. If a sample from a subject is positive for DPD expression, a recommendation can be made to not treat the subject with 5-FU. 5-FU is a pyrimidine analog that can act as a thymidylate synthase inhibitor. A dose of 5-FU can be recommended based on the level of DPD expression in a sample from a subject.

The status of OPRT (also known as uridine monophosphate synthetase; UMPS uridine monophosphate synthase; OPRtase; OMPdecase; UMP synthase; orotidine 5'-phosphate decarboxylase; orotate phosphoribosyltransferase phosphoribosyltransferase; orotate phosphoribosyl transferase; orotidine-5'-decarboxylase) in a sample from a subject can be used to determine whether to recommend 5-FU as a drug treatment option for the subject, e.g., a lung cancer patient or a non-small-cell lung cancer patient (Nakano J et al. (2006) *British Journal of Cancer* 95:607-615). For example, if a sample from a subject is positive for OPRT expression, a recommendation can be made to treat the subject with 5-FU. If a sample from a subject is negative for OPRT expression, a recommendation can be made to not treat the subject with 5-FU.

The status of TS (also known as thymidylate synthetase; TMS; TSase; HsT422; MGC88736; TYMS) in a sample from a subject can be used to determine whether to recommend 5-FU as a drug treatment option for the subject, e.g., a lung cancer patient or a non-small-cell lung cancer patient (Nakano J et al. (2006) *British Journal of Cancer* 95:607-615; Cascinu S et al. (2001) *Ann Oncol* 2:239-244). Thymidylate synthase catalyzes the methylation of deoxyuridylate to deoxythymidylate using 5,10-methylenetetrahydrofolate (methylene-THF) as a cofactor. This function maintains the dTMP (thymidine-5-prime monophosphate) pool critical for DNA replication and repair. TS is considered to be the primary site of action for 5-fluorouracil, 5-fluoro-2-prime-deoxyuridine, and some folate analogs. If a sample from a subject is negative for TS expression (or has low TS expression), a recommendation can be made to treat the subject with 5-FU. If a sample from a subject is positive for TS expression (or has high TS expression), a recommendation can be made to not treat the subject with 5-FU.

Bevacizumab (Avastin) can be recommended as a drug treatment option for a subject, e.g., a lung or NSCLC patient.

Docetaxel (Taxotere) can be recommended as a drug treatment option for a subject, e.g., a metastatic lung cancer patient, a non-small-cell lung cancer patient, a breast cancer patient, a prostate cancer patient, a gastric cancer patient, or a head and neck cancer patient. Docetaxel (Taxotere) an anti-mitotic that stabilizes microtubules. Docetaxel (Taxotere) is indicated for the treatment of patients with locally advanced or metastatic breast cancer after failure of prior chemotherapy, and it is indicated in combination with doxorubicin and cyclophosphamide for the adjuvant treatment of patients with operable node-positive breast cancer. Docetaxel (Taxotere) as a single agent is indicated for the treatment of patients with locally advanced or metastatic non-small cell lung cancer (NSCLC) after failure of prior platinum-based chemotherapy. Docetaxel (Taxotere) in combination with cisplatin is indicated for the treatment of patients with unresectable, locally advanced or metastatic NSCLC who have not previously received chemotherapy for this condition. Docetaxel (Taxotere) in combination with prednisone is indicated for the treatment of patients with androgen independent (hormone refractory) metastatic prostate cancer. Docetaxel (Taxotere) in combination with cisplatin and fluorouracil is indicated for the treatment of patients with advanced gastric adenocarcinoma, including adenocarcinoma of the gastroesophageal junction, who have not received prior chemotherapy for advanced disease. Docetaxel (Taxotere) in combination with cisplatin and fluorouracil is indicated for the induction treatment of patients with locally advanced squamous cell carcinoma of the head and neck (SCCHN).

The status of Kras in a sample from a subject can be used to determine whether to recommend gefitinib (Iressa) as a drug treatment option for the subject, e.g., a lung cancer patient or a non-small-cell lung cancer patient (Carbone D P (2004) *Nature Clinical Practice Oncology* 1:66-67). For example, if a sample from a subject expresses wild-type Kras, a recommendation can be made to treat the subject with gefitinib (Iressa). If a sample from a subject expresses mutated Kras, a recommendation can be made to not treat the subject with gefitinib (Iressa). If a sample from a subject has mutations in Kras in exon 2, a recommendation can be made to not treat the subject with gefitinib (Iressa) (Pao W et al. (2005) *PLoS Med* 2(1): e17. doi:10.13711journal.pmed.0020017). Gefitinib (Iressa) is an anticancer drug that can inhibit tyrosine kinase activity of EGFR.

Gemcitabine (Gemzar) can be recommended as a drug treatment option for a subject, e.g., a lung cancer patient, a ovarian cancer patient, a pancreatic cancer patient, or a NSCLC patient. Gemcitabine (Gemzar) is a nucleoside analog in which the hydrogen atoms on the 2' carbons of deoxycytidine are replaced by fluorine atoms. Gemcitabine (Gemzar) can be recommended as a first line drug treatment option for inoperable stage IIIA, IIIB, or metastatic stage IV lung cancer. Gemcitabine (Gemzar) is indicated in combination with carboplatin for a patient with ovarian cancer that has returned at least 6 months after the patient had finished platinum-based therapy. Gemcitabine (Gemzar) is indicated in combination with cisplatin for the first-line treatment of patients with locally advanced (Stage IIIA or Stage IIIB) or metastatic (Stage IV or cancer that has spread) non-small cell lung cancer for whom surgery is not possible. Gemcitabine (Gemzar) in combination with paclitaxel is approved by the FDA for the first-line treatment of patients with metastatic breast cancer after they have received anthracycline, unless their medical condition did not allow them to receive an anthracycline. Gemcitabine (Gemzar) is indicated as a single agent first-line treatment for patients with locally advanced (Stage II or Stage III when surgery is not an option) or metastatic (Stage IV) adenocarcinoma of the pancreas. Gemcitabine (Gemzar) is also indicated for pancreatic cancer patients previously treated with 5-FU.

Vinorelbine (Navelbine) can be recommended as a drug treatment option for a subject, e.g., a lung cancer patient, a breast cancer patient, or NSCLC patient with and unresectable advanced tumor. Vinorelbine (Navelbine) can be recommended as a drug treatment option alone or in combination with cisplatin. Vinorelbine (Navelbine) can be recommended as a drug treatment option for a patient with Stage III or Stage IV lung cancer or NSCLC. Vinorelbine (Navelbine) is a 5'NOR semi-synthetic vinca alkaloid that can interfere with microtubule assembly.

The status of Kras or EGFR in a sample from a subject can be used to determine whether to recommend erlotinib (Tarceva) as a drug treatment option for the subject, e.g., a lung cancer patient, non-small-cell lung cancer patient, adenocarinoma (ADC) patient, or squamous cell carcinoma (SCC) patient (Pao W. et al. (2005) *PLOS Medicine* 2(1):e17). For example if a sample has wild-type Kras, a recommendation can be made to treat the subject with erlotinib (Tarceva). If a sample has mutated Kras, a recommendation can be made to not treat the subject with erlotinib (Tarceva). If a sample has mutated EGFR, a recommendation can be made to treat the subject with erlotinib (Tarceva). If a sample from a subject has mutations in exons 18-21 of EGFR, a recommendation can be made to treat the subject with erlotinib (Tarceva). If a sample has wild-type EGFR, a recommendation can be made to not treat the subject with erlotinib (Tarceva). Erlotinib (Tarceva) can be recommended as a first line therapy.

A recommendation can be made to administer topotecan (Hycamtin) to a subject, e.g., a lung cancer patient or a small cell lung cancer patient, that has failed a first line of therapy or has cancer progression after an initial response to chemotherapy (O'Brien M E et al. (2006) *J Clin Oncol* 24:5441-5447). Topotecan (Hycamtin) is a topoisomerase 1 inhibitor.

Pemetrexed disodium (Alimta) can be recommended as a drug treatment option for a subject, e.g., a lung cancer patient or non-small-cell lung cancer patient that has locally advanced or metastatic cancer. Pemetrexed disodium is a member of the folate antimetabolite class of chemotherapy drugs. Pemetrexed can inhibit three enzymes used in purine and pyrimidine synthesis: thymidylate synthase (TS), dihydrofolate reductase (DHFR), and glycinamide ribonucleotide formyltransferase (GARFT). Pemetrexed for injection (Alimta) is approved by the FDA in combination with cisplatin for the initial treatment of advanced nonsquamous non-small cell lung cancer (NSCLC). Pemetrexed for injection (Alimta) as a single agent is approved for maintaining the initial treatment effect of chemotherapy in patients with advanced nonsquamous non-small cell lung cancer whose disease has not worsened after initial therapy. Pemetrexed for injection (Alimta) is approved by the FDA as a single agent for the treatment of patients with advanced nonsquamous non-small cell lung cancer (NSCLC) after prior chemotherapy. Pemetrexed for injection (Alimta) is a treatment for malignant pleural mesothelioma (MPM), a cancer that affects the inside lining of the chest cavity. Pemetrexed for injection (Alimta) can be given with cisplatin when surgery is not an option.

Porfimer sodium (Photofrin) can be recommended as a drug treatment option for a subject, e.g., a lung cancer patient or non-small-cell lung cancer patient who is undergoing photodynamic therapy. Porfimer sodium is a sensitizer that can be administered intravenously for use in photodynamic therapy. Photofrin is indicated for palliation of patients with completely obstructing esophageal cancer, or of patients with partially obstructing esophageal cancer who, in the opinion of their physician, cannot be satisfactorily treated with Nd:YAG laser therapy. Photofrin is indicated for treatment of microinvasive endobronchial non-small-cell lung cancer (NSCLC) in patients for whom surgery and radiotherapy are not indicated. Photofrin is indicated for reduction of obstruction and palliation of symptoms in patients with completely or partially obstructing endobronchial NSCLC.

Paclitaxel (Taxol) can be recommended as a drug treatment option for a subject, e.g., a lung cancer patient or non-small-cell lung cancer patient, as a first line therapy and/or in combination with cisplatin. Paclitaxel is a mitotic inhibitor that stabilizes microtubules.

Bleomycin (Blenoxane) can be recommended as a drug treatment option for a subject, e.g., a patient with pleural effusion or malignant pleural effusion (MPE), the accumulation of fluid in the pleural space that can result from cancer metastasis. Bleomycin (Blenoxane) can be recommended to be used in the management of the following conditions as either a single agent or in combination with other chemotherapeutic agents: squamous cell carcinoma (head and neck, including: mouth, tongue, tonsil, nasopharynx, oropharynx, sinus, palate, lip, buccal mucosa, gingivae, epiglottis, skin, larynx; penis, cervix, and vulva); Hodgkin's Disease and non-Hodgkin's lymphoma; and testicular carcinoma (embryonal cell, choriocarcinoma, and teratocarcinoma). Bleomycin (Blenoxane) is a glycopeptide that can induce DNA strand breaks.

Leucovorin (folinic acid, Wellcovorin) can be recommended as a drug treatment option for a subject, e.g., a prostate cancer patient, in combination with 5-FU to prolong survival or provide palliative care.

The status of EGFR can be determined by, e.g., sequencing or detection of expression, and be used to determine whether to recommend lapatinib as a drug treatment option (Trowe T. et al. (2008) *Clinical Cancer Research* 14:2465-2475). Lapatinib is a tyrosine kinase inhibitor. If a sample overexpresses EGFR, a recommendation can be made to treat the subject with lapatinib. If a sample does not overexpress EGFR, a recommendation can be made to not treat the subject with lapatinib.

The status of ErbB2 (also known as HER2, NEU, NGL, TKR1, CD340, HER-2, HER-2/neu) can be used to determine whether to recommend leucovorin as a drug treatment option for a subject, e.g, a cancer patient (NCCN).

The status of TOPO1 can be determined by, e.g., IHC, and can be used to determine whether to recommend oxaliplatin as a drug treatment option for a subject, e.g., a colon cancer patient (Braun M. S. et al. (2008) *J Clin Oncol* 26:2690-2698). Oxaliplatin is thought to inhibit DNA synthesis.

Etoposide phosphate (Etopophos) can be recommended as a drug treatment option for a subject, e.g., a lung cancer or small cell lung cancer patient. Etoposide phosphate is an inhibitor of topoisomerase II.

In the methods of the provided invention, one or more recommendations in a report for treating or not treating a subject with one or more drugs can be made based on one or more correlations between one or more molecular markers of a particular status and one or more drugs. A recommendation in a report (e.g., treat with a drug or do not treat with a drug) can be made based on the subject's type of cancer.

C. Examples of Marker/Drug Combinations for Colon Cancer

In the methods of the provided invention a drug can be recommended as a treatment option (first class or second class) or recommended not to be used as a treatment option (third class) based on the status of one or more molecular markers in a sample in a subject, e.g., a colon cancer patient.

The status of c-kit (CD117) in a sample from a colon cancer patient can be determined by, e.g., flow cytometry and/or sequencing, and imatinib mesylate (Gleevec) can be recommended for the subject based on the status of c-kit. For example, if flow cytometry indicates the expression of c-kit in the sample, and the protein sequence has key mutations, imatinib mesylate (Gleevec) can be recommended for the subject as a drug treatment option. If a sample from a colon cancer patient does not express c-kit or have c-kit with key mutations, a recommendation can be made to not treat the subject with imatinib mesylate (Gleevec).

The status of the Kras in a sample from a subject can be determined by, e.g., sequencing, and cetuximab (Erbitux) or panitumumab (Vectibix) monotherapy can be recommended for the subject based on the status of the Kras sequence. For example, if the sample from a colon cancer patient has a wild type Kras sequence (e.g., as determined by exon 2 genotyping or sequencing), cetuximab (Erbitux) or panitumumab (Vectibix) monotherapy can be recommended as a drug treatment option for the colon cancer patient. If the sample from a colon cancer patient has a mutant Kras sequence (e.g., as determined by exon 2 genotyping or sequencing), a recommendation can be made not to treat the colon cancer patient with cetuximab (Erbitux) or panitumumab (Vectibix) monotherapy.

The status of BRAF in a sample from a colon cancer patient can be determined by, e.g., sequencing, and cetuximab (Erbitux) or panitumumab (Vectibix) can be recommended to a subject based on the status of BRAF (Nicolantonio D et al. (2008) *J Clin. Oncol.* 26:5705-5712; Cappuzzo F et al. (2008) *Br J Cancer* 99:83-89). For example, if a subject does not have a V600E mutation in its BRAF sequence (e.g., as determined by V600E genotyping or sequencing), cetuximab (Erbitux) or panitumumab (Vectibix) can be recommended as a drug treatment option. If a subject has a V600E mutation in its BRAF sequence (e.g., as determined by V600E genotyping or sequencing), then a recommendation can be made not to treat the patient with cetuximab (Erbitux) or Panitumumab (Vectibix). Treatment of subjects with the BRAF V600E mutation with the BRAF inhibitor sorafenib can restore sensitivity to cetuximab (Erbitux) or panitumumab (Vectibix) monotherapy. If a sample from a subject has a V600E mutation in its BRAF sequence, then a recommendation can be made to treat the subject with sorafenib and cetuximab (Erbitux) and/or panitumumab (Vectibix).

The presence or absence of microsatellite stability in a sample from a subject, e.g., a colon cancer patient, can be used to determine whether or not to recommend fluorouracil-based adjuvant chemotherapy to the subject. Fluorouracil-based adjuvant chemotherapy benefited patients with stage II or stage III colon cancer with microsatellite-stable tumors or tumors exhibiting low-frequency microsatellite instability but not those with tumors exhibiting high-frequency microsatellite instability (Ribic C M et al. (2003) *NEJM* 349:247-257). If a sample from a subject with stage II or stage III colon cancer has a microsatellite-stable tumor or a tumor exhibiting low-frequency microsatellite instability, a recommendation can be made to treat the subject with fluorouracil-based adjuvant chemotherapy. If a subject with stage II or stage III colon cancer has a tumor that exhibits high-frequency microsatellite instability, a recommendation can be made not to treat the subject with fluorouracil-based adjuvant chemotherapy. Microsatellite stability can be determined by DNA sequencing.

The status of EGFR copy number in a sample from a subject, e.g. a colon cancer patient, can be determined by, e.g., FISH or qPCR, and can be used to determine whether to recommend cetuximab (Erbitux) or panitumumab (Vectibix) to the subject. An increased copy number of EGFR correlates with a good response to cetuximab (Erbitux) or panitumumab (Vectibix) monotherapy (Cappuzzo F et al. (2007) *Annals of Oncology* 19:717-723). If a sample from a subject has an increased copy number of EGFR, a recommendation can be made to treat the subject with cetuximab (Erbitux) or panitumumab (Vectibix) monotherapy.

The status of the 18q chromosome in a sample from a subject, e.g., a colon cancer patient, can be determined by, e.g., qPCR, and can be used to determine whether to treat the subject with adjuvant therapy (Jen J. et al. (1994) *NEJM* 331:213-221). The status of chromosome 18q has prognostic value in patients with stage II colorectal cancer. Stage II colorectal cancer patients with chromosome 18q allelic loss have a prognosis that is similar to that in patients with stage III cancer, who are thought to benefit from adjuvant therapy. In contrast, stage II colorectal cancer patients who do not have chromosome 18q allelic loss in their tumor have a survival rate similar to that of patients with stage I disease and may not require additional therapy. If a sample from a subject (e.g., a stage II colon cancer patient) has chromosome 18q allelic loss, then a recommendation can be made to treat the subject with adjuvant therapy as if the patient were a stage III cancer patient. If a sample from a subject (e.g., a stage II colon cancer patient) does not have chromosome 18q allelic loss, a recommendation can be made to not treat the subject with adjuvant therapy.

The status of thymidylate synthase levels in a sample from a subject, e.g., a colon cancer patient, can be determined by, e.g., IHC, and can be used to determine whether to treat the subject with 5-FU-based chemotherapy (Elder D. (2002) *J. Clin. Oncol.* 20:1721-1728; Cascinu S et al. (2001) *Ann Oncol* 2:239-244; Ciaparrone M. et al. (2006) *Oncology* 70:366-377).

If a sample from a subject (e.g., a colon cancer patient) has a high TS level (as determined by, e.g., IHC), a recommendation can be made to treat or to not treat the subject with adjuvant 5-FU-based chemotherapy. If a sample from a subject (e.g., a colon cancer patient) has a low TS level, a recommendation can be made to treat or to not treat the subject with adjuvant 5-FU-based chemotherapy.

The status of Topo1 expression levels in a sample from a subject, e.g., a colon cancer patient, can be determined by, e.g., IHC, and can be used to determine whether to treat the subject with irinotecan. Progression-free survival (PFS) was not improved in patients with low Topo1 by the addition of irinotecan, but patients with moderate/high Topo1 benefited from the addition of irinotecan (Braun M S et al. (2008) *J. Clin. Oncol.* 26:2690-2698). If a sample from a subject has low Topo1 expression, then a recommendation can be made to not treat the subject with irinotecan. If a sample from a subject has moderate to high Topo1 expression, then a recommendation can be made to treat the subject with irinotecan.

The status of Kras in a sample from a colon cancer patient can be determined by, e.g., sequencing, and bevacizumab (Avastin) can be recommended as a drug treatment option based on the status of Kras.

The status of TOPO1 in a sample from a colon cancer patient can be determined by, e.g., immunohistochemistry (IHC) and/or sequencing, and can be used to determine whether to recommend 5-FU or capecitabine (Xeloda) as a drug treatment option. For example, if TOPO1 expression can be detected by IHC or if TOPO1 has a certain sequence, then capecitabine (Xeloda), or fluorouracil (5-FU) with or without irinotecan (Camptosar), can be recommended as a drug treatment option.

Combinations of markers/targets, drug/therapeutics, and cancers can be found in FIG. 6.

D. Drugs with Inhibitors of DNA Synthesis

Other cancer drug therapies that can be recommended to a subject include, for example, FOLFOX. FOLFOX is a chemotherapy regimen that can be used to treat colorectal cancer. The FOLFOX regimen includes folinic acid (leucovorin), fluorouracil (5-FU), and oxaliplatin (Eloxatin). 5-FU can act as an inhibitor of thymidylate synthase, which can block synthesis of thymidine, which can affect DNA replication. Capecitabine (Xeloda) is a prodrug that can be converted enzymatically to 5-FU.

Capecitabine (Xeloda) can be used to treat metastatic breast cancer and colorectal cancer. Irinotecan (Camptosar) is an inhibitor of topoisomerase 1 that can be used for treatment of colon cancer. FOLFIRI is a chemotherapy regimen that can be used to treat colorectal cancer. The FOLFIRI regimen includes folinic acid (leucovorin), fluorouracil (5-FU), irinotecan (Camptosar). CapeOx is a chemotherapy regimen that includes capecitabine (Xeloda) and oxaliplatin (Eloxatin).

E. Patient Metabolism

The stratifying of cancer drug treatments can take into account the role of genes that affect drug absorption, distribution, metabolism, and excretion (the pharmacokinetics and pharmacodynamics of the drug treatment). The stratifying of drug treatments can take into account whether the subject or patient is hypermetabolic. The stratifying of drug treatments can take into account the cytochrome P450 (CYP450) status of said subject or patient. The CYP450 status of a subject or a patient can be determined, for example, from assessments made by genotyping genes encoding CYP450 (e.g., CYP2D6, CYP2C19, and CYP2C9). For example, the CYP450 status can be assessed using the Roche® AmpliChip CYP450 Test, which tests for gene variations in CYP2D6 and CYP2C19. The stratifying of one or more drug treatment options can be based on tests for defects in the enzyme thiopurine methyltransferase (TMPT), which can prevent metabolism of the anti-cancer drug 6-mercaptopurine (6MP). Results from Affymetrix® Drug Metabolizing Enzymes and Transporters (DMET)— Early Access Solution, The Human1M BeadChip from Illumina®, Human1M-Duo DNA Analysis BeadChip from Illumina®, and HumanExon510S-Duo DNA Analysis BeadChip from Illumina®, can be used to stratify the cancer drug treatment options.

F. Sources of Drug Treatment Options

The list of drug treatments to be stratified can be compiled from information sources available to those skilled in the art. The drugs can be described in scientific literature, and the drugs can be those used in unpublished clinical trials (clinicaltrials.gov/). The drugs can be listed in the Centers for Medicare and Medicaid Services (CMS) anti-cancer treatment compendia for determining which drugs may be covered under Medicare Part B to treat cancer patients, including the National Comprehensive Cancer Network (NCCN) Drugs and Biologics Compendium™ Thomson Micromedex DrugDex®, and Elsevier Gold Standard's Clinical Pharmacology compendium, and American Hospital Formulary Service—Drug Information Compendium. The drugs can be those listed for a specific cancer on the NCCN Clinical Practice Guidelines in Oncology™ website or in the American Society of Clinical Oncology (ASCO) clinical practice guidelines.

G. Types of Cancers

The NCCN Clinical Practice Guidelines in Oncology™ website provides clinical practice guidelines for treating a variety of cancers. These clinical practice guidelines can be downloaded. The guidelines provide information regarding care options that take into account risks and benefits associated with a procedure.

The condition for which one or more drug treatment options can be stratified and/or annotated can include a cancer listed on the NCCN website. The conditions or cancers can include, for example, acute myeloid leukemia; bladder cancer, including upper tract tumors and urothelial carcinoma of the prostate; bone cancer, including chondrosarcoma, Ewing's sarcoma, and osteosarcoma; breast cancer, including noninvasive, invasive, phyllodes tumor, Paget's disease, and breast cancer during pregnancy; central nervous system cancers, adult low-grade infiltrative supratentorial astrocytoma/oligodendroglioma, adult intracranial ependymoma, anaplastic astrocytoma/anaplastic oligodendroglioma/glioblastoma multiforme, limited (1-3) metastatic lesions, multiple (>3) metastatic lesions, carcinomatous lymphomatous meningitis, nonimmunosuppressed primary CNS lymphoma, and metastatic spine tumors; cervical cancer; chronic myelogenous leukemia (CML); colon cancer, rectal cancer, anal carcinoma; esophageal cancer; gastric (stomach) cancer; head and neck cancers, including ethmoid sinus tumors, maxillary sinus tumors, salivary gland tumors, cancer of the lip, cancer of the oral cavity, cancer of the oropharynx, cancer of the hypopharynx, occult primary, cancer of the glottic larynx, cancer of the supraglottic larynx, cancer of the nasopharynx, and advanced head and neck cancer; hepatobiliary cancers, including hepatocellular carcinoma, gallbladder cancer, intrahepatic cholangiocarcinoma, and extrahepatic cholangiocarcinoma; Hodgkin disease/lymphoma; kidney cancer; melanoma; multiple myeloma, systemic light chain amyloidosis, Waldenström's macroglobulinemia; myelodysplastic syndromes; neuroendocrine tumors, including multiple endocrine neoplasia, type 1, multiple endocrine neoplasia, type 2, carcinoid tumors, islet cell tumors, pheochromocytoma, poorly differentiated/small cell/atypical lung carcinoids; Non-Hodgkin's Lymphomas, including chronic lymphocytic leukemia/small lymphocytic lymphoma, follicular lymphoma, marginal zone lymphoma, mantle cell lymphoma, diffuse large B-Cell lymphoma, Burkitt's lymphoma, lymphoblastic lymphoma, AIDS-Related B-Cell lymphoma, peripheral T-Cell lymphoma, and mycosis fungoides/Sezary Syndrome; non-melanoma skin cancers, including basal and squamous cell skin cancers, dermatofibrosarcoma protuberans, Merkel cell carcinoma; non-small cell lung cancer (NSCLC), including thymic malignancies; occult primary; ovarian cancer, including epithelial ovarian cancer, borderline epithelial ovarian cancer (Low Malignant Potential), and less common ovarian histologies; pancreatic adenocarcinoma; prostate cancer; small cell lung cancer and lung neuroendocrine tumors; soft tissue sarcoma, including soft-tissue extremity, retroperitoneal, intra-abdominal sarcoma, and desmoid; testicular cancer; thymic malignancies, including thyroid carcinoma, nodule evaluation, papillary carcinoma, follicular carcinoma, Hirthle cell neoplasm, medullary carcinoma, and anaplastic carcinoma; uterine neoplasms, including endometrial cancer and uterine sarcoma.

Medical information regarding cancers can be found at websites, for example, www.cancer.gov, www.nexcura.cancer.com, www.asco.org, and nccn.org/professionals/physician.

H. How Stratification is Indicated on a Report

Figure 8:
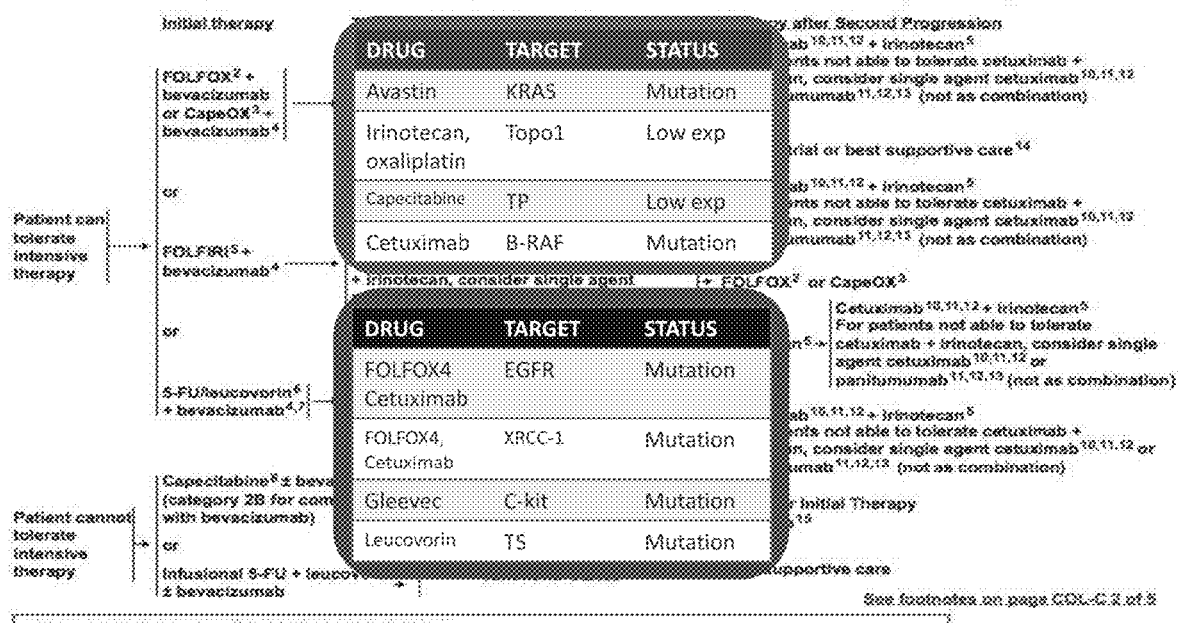
FIG. 8 illustrates an example of a report generated by a method of the provided invention.

The stratifying of drug treatment options can be indicated by markings on a form downloaded from a website, for example, the NCCN Clinical Practice Guidelines in Oncology™ or in the American Society of Clinical Oncology (ASCO) clinical practice guidelines, or on a printed report. For example, color coding of drug treatment options can be used to indicate stratification of drug treatment options on information downloaded or printed, for example, from the NCCN Clinical Practice Guidelines in Oncology™ website. The drug treatment options that can be stratified include those found in the American Society of Clinical Oncology (ASCO) clinical practice guidelines. The drug treatment options can be stratified such that drug treatment options most likely to be efficacious (first class; recommend the subject be treated with the drug), based on the status of one of more molecular markers of the sample or tumor, are highlighted or written in green or a shade of green; drugs that may have some efficacy are highlighted or written in yellow or a shade of yellow (second class; recommend the subject be treated with the drug with some caution or caveat), and drugs for which no information is available or for which the scientific literature indicates the drug will not be efficacious or will be toxic in light of the status of the subject's one or more molecular markers are highlighted or written in red or a shade of red (third class; recommend the subject not be treated with the drug). FIGS. 2A-2C illustrate an example in which (FIG. 2A) a health care provider accesses a report on a computer based on (FIG. 2B) the NCCN Clinical Practice Guidelines in Oncology related to colon cancer, and (FIG. 2C) drugs treatment options are classified (stratified) by colors. FIG. 8 illustrates a printed hard copy example of a report in which drug, target (molecular marker), and status of a target (molecular marker) are indicated. Other identifiers, such as number ranking, separate groups, asterisks, etc., can be used to indicate stratification of the drug treatment options for a condition.

The report can contain other information, including, e.g., type of assay or technique used for determining the status of a molecular marker, different type of molecular marker status (e.g., wild-type or mutant sequence; e.g., DNA, RNA, or protein sequence; high expression or low expression levels, e.g., mRNA expression or protein expression; etc.). The report can contain information on a drug dosing recommendation based on the status of one or molecular markers.

The report with the stratified treatment options can be provided by the personalized medicine business to a health care professional (e.g., oncologist) and/or the subject for whom the report is prepared. The report can be made available online or be delivered in hardcopy form by a delivery service. An alert, such as an email, text message, phone call, facsimile, etc. can be sent to a subject or health care provider indicating that the report is available. A fee can be charged by the personalized medicine business in exchange for preparing and/or sending the report.

I. Validation of Tumor Markers

The methods of the provided invention can be used to validate molecular markers. A molecular marker to be validated for a particular cancer can be selected by analyzing the literature. Stored samples from subjects whose treatment outcome is known (retrospective sample) can be used to validate a molecular marker of a condition, e.g., a cancer. Validating a tumor marker can include determining a DNA sequence variation and correlating the variation to RNA expression. Hundreds of markers can be validated in parallel. Quantitative cellular heterogeneity can be used as a measure of survival. A validation study can be a FFPE retrospective validation study. A validation study can be a prospective validation study. A validation study can be a multi-marker retrospective correlation study.

V. Annotating Cancer Drug Treatment Options

A. Annotating with Information Regarding Experimental Drugs and FDA-Approved Drugs for Off-Label Use The methods of the provided invention can include obtaining a sample, determining the status of one or more molecular markers, stratifying one or more drug treatment options based on the status of the one or more molecular markers, and annotating drug treatment options in a report based on the status of the one or more molecular markers. The annotated information can be used by a health care provider to select other drug treatment options and/or provide information about drug treatment options to an insurance company. The method can include annotating the drug treatment options for a condition in, for example, the NCCN Clinical Practice Guidelines in Oncology™ or the American Society of Clinical Oncology (ASCO) clinical practice guidelines.

The drug treatment options that are stratified in a report can be annotated in the report by listing additional drug treatment options. An additional drug treatment can be an FDA-approved drug for an off-label use. A provision in the 1993 Omnibus Budget Reconciliation Act (OBRA) requires Medicare to cover off-label uses of anticancer drugs that are included in standard medical compendia. The drugs used for annotating lists can be found in CMS approved compendia, including the National Comprehensive Cancer Network (NCCN) Drugs and Biologics Compendium™, Thomson Micromedex DrugDex®, Elsevier Gold Standard's Clinical Pharmacology compendium, and American Hospital Formulary Service—Drug Information Compendium®.

The drug treatment options can be annotated by listing an experimental drug that may be useful in treating a cancer with one or more molecular markers of a particular status. The experimental drug can be a drug for which in vitro data, in vivo data, animal model data, pre-clinical trial data, or clinical-trial data are available. The data can be published in peer-reviewed medical literature found in journals listed in the CMS Medicare Benefit Policy Manual, including, for example, *American Journal of Medicine, Annals of Internal Medicine, Annals of Oncology, Annals of Surgical Oncology, Biology of Blood and Marrow Transplantation, Blood, Bone Marrow Transplantation, British Journal of Cancer, British Journal of Hematology, British Medical Journal, Cancer, Clinical Cancer Research, Drugs, European Journal of Cancer* (formerly the *European Journal of Cancer and Clinical Oncology*), *Gynecologic Oncology, International Journal of Radiation, Oncology, Biology, and Physics, The Journal of the American Medical Association, Journal of Clinical Oncology, Journal of the National Cancer Institute, Journal of the National Comprehensive Cancer Network* (NCCN), *Journal of Urology, Lancet, Lancet Oncology, Leukemia, The New England Journal of Medicine*, and *Radiation Oncology*.

B. Annotating with Scientific Information about the Drugs

The drug treatment options can be annotated by providing a link on an electronic based report connecting a listed drug to scientific information regarding the drug. For example, a link can be provided to information regarding a clinical trial for a drug (clinicaltrials.gov). If the report is provided via a computer or computer website, the link can be a footnote, a hyperlink to a website, a pop-up box, or a fly-over box with information, etc. The annotated information can become available when a computer user clicks on a condition or a treatment option on the downloaded and annotated Clinical Practice Guidelines in Oncology™ (FIG. 3). The report and the annotated information can be provided on a printed form, and the annotations can be, for example, a footnote to a reference.

The information for annotating one or more drug treatment options in a report can be provided by a commercial entity that stores scientific information, for example, Ingenuity® Systems. A health care provider can treat a subject, such as a cancer patient, with an experimental drug listed in the annotated information, and the health care provider can access the annotated drug treatment option, retrieve the scientific information (e.g., print a medical journal article) and submit it (e.g., a printed journal article) to an insurance company along with a request for reimbursement for providing the drug treatment. Physicians can use any of a variety of Diagnosis-related group (DRG) codes to enable reimbursement.

A drug treatment option in a report can also be annotated with information regarding other molecular components in a pathway that a drug affects (e.g., information on a drug that targets a kinase downstream of a cell-surface receptor that is a drug target). The drug treatment option can be annotated with information on drugs that target one or more other molecular pathway components. The identification and/or annotation of information related to pathways can be outsourced or subcontracted to another company, for example Ingenuity®.

The annotated information can be, for example, a drug name (e.g., an FDA approved drug for off-label use; a drug found in a CMS approved compendium, and/or a drug described in a scientific (medical) journal article), scientific information concerning one or more drug treatment options, one or more links to scientific information regarding one or more drugs, clinical trial information regarding one or more drugs (e.g., information from clinicaltrials.gov/), one or more links to citations for scientific information regarding drugs, etc.

The annotated information can be inserted into any location in a report. Annotated information can be inserted in multiple locations on a report. Annotated information can be inserted in a report near a section on stratified drug treatment options. Annotated information can be inserted into a report on a separate page from stratified drug treatment options. A report that does not contain stratified drug treatment options can be annotated with information.

VI. Screening Drugs Using Xenograft Models and In Vitro Cultures

The provided methods can also include means for investigating the effects of drugs on sample (e.g. tumor cells) isolated from a subject (e.g. cancer patient). An in vitro culture using a tumor from a cancer patient can be established using techniques known to those skilled in the art.

The provided method can also include establishing a xenograft model using said sample. The sample can be a tumor biopsy from a human subject. Cells from tumor biopsy can be transplanted to a species that includes, for example, a pig, mouse, severe combined immunodeficiency (SCID) mouse, rat, nude rat, etc.

The provided method can also include high-throughput screening of FDA approved off-label drugs or experimental drugs using said in vitro culture and/or xenograft model.

The provided method can also include monitoring tumor antigen for recurrence detection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Prophetic Example 1: Stratifying Colon Cancer Drug Treatment Options

A colon cancer patient visits a physician, and the physician performs a tumor biopsy. The physician arranges to submit the tumor biopsy to a personalized medicine business for characterization of molecular markers. In the meantime, the physician prescribes a first line drug treatment for the cancer patient selected from those disclosed in the NCCN Clinical Practice Guidelines in Oncology™ guidelines for Colon Cancer.

The tumor biopsy is obtained by the personalized medicine business, and primary tumor cells are separated from non-tumor cells by flow-sorting. The isolated primary tumor cells are tested for the status of one or more molecular marker(s) by comparative genomic hybridization (CGH), DNA sequencing, and high density expression. The status of the one or more molecular markers is used to analyze scientific publications for literature related to responses of tumors with molecular markers of a similar status to drug treatment options. The analysis is completed by one or more individuals with knowledge or expertise in colon cancer treatment employed by the personalized medicine business or outsourced or subcontracted to another company. The treatment options listed in the NCCN Clinical Practice Guidelines in Oncology™ guidelines for Colon Cancer are evaluated in light of the status of the one or more molecular markers identified in the tumor cells and in light of available scientific information regarding those markers and colon or other cancer drug treatment options. An individual or teams ranks or classifies the drug treatment options based on predicted efficacy given the status of the molecular markers in the cancer patient's sample. Those drug treatment options predicted to have the highest efficacy are highlighted in green, those predicted to have lower efficacy are highlighted in yellow, and those for which a marker indicates a drug will not be efficacious or will be toxic are indicated in red.

In addition, scientific literature and clinical trial information are reviewed for other drug treatment options not listed in the NCCN Clinical Practice Guidelines in Oncology™ guidelines for Colon Cancer. Based on these information sources, a report containing the NCCN Clinical Practice Guidelines in Oncology™ guidelines for Colon Cancer is annotated by listing other drug treatment options that include FDA-approved drugs for an off-label use and/or experimental drugs. The downloaded version of the guidelines lists the annotated drug, and a link is provided from each listed drug treatment option to scientific information related to the use of that drug.

The stratified drugs treatment options and annotated drug treatment options are shared with the patient and/or the physician in the form of an electronic or hard copy report. The physician and/or patient make a second line treatment decision to use an experimental drug based on the molecular marker data. The health care provide can access the modified NCCN Clinical Practice Guidelines in Oncology™ guidelines for Colon Cancer on a computer, point to the annotated drug, which brings up a pop-box with a link to a journal article concerning the experimental drug. The health care provider can submit the journal article to an insurance provider to seek reimbursement for the treatment.

Prophetic Example 2: Xenograft and In Vitro Cultures

A colon cancer patient visits a physician, and the physician performs a tumor biopsy. The physician submits the biopsy to a personalized medicine business for molecular characterization. In addition, an in vitro culture and nude rat xenograft model are established. A series of experimental drugs are identified as described in Prophetic Example 1 that may be helpful for the patient. While the patient is in a first line drug therapy, a high-throughput screen is performed with the experimental drugs and the in vitro culture and xenograft models. Results of the high-throughput screen are reported to the patient and the physician, who use the information in deciding on a second-line therapy if the first line therapy fails or an adjunct in the end stage administration if appropriate.

Prophetic Example 3: Annotating Treatment Options on the NCCN Website

The scientific literature lists a treatment X for cancer A and cancer B. Treatment Y is useful in treating cancer B, but the affect of treatment Y on cancer A, however, is not known or studied. A report with the NCCN Clinical Practice Guidelines in Oncology™ on a website is annotated with information describing the relationship between treatment Y and cancer B and treatment X and cancers A and B, and a note is added that treatment Y may be effective for off-label use in treating cancer A.

Prophetic Example 4: Physician Use of NCCN Website with Stratified Treatment Options A physician (FIG. 2A) accesses a NCCN Clinical Practice Guidelines in Oncology™ file on Colon Cancer (FIG. 2B) in which a patient's treatment options have been stratified based on the status of the patient's molecular markers (FIG. 2C). The highest ranked drug treatment option for a patient with marker X and is marked in green (Drug A). The next ranked drug is marked in yellow (Drug B). The drug marked in red (Drug C) does not display efficacy based on the status of the molecular marker X.

Prophetic Example 5: Physician Use of NCCN Website with Annotated Treatment Options A physician accesses a NCCN Clinical Practice Guidelines in Oncology™ file on Colon Cancer that has been annotated with an additional drug treatment option D (FIG. 3; 300). Option D is an experimental drug with published data in vitro on treating a tumor with a marker whose status is shared with the physician's patient. The physician treats the patient with drug D (302). The physician follows the link on the page to a medical journal article on the use of drug D in the in vitro study (304) and submits the article to an insurance company with a request for reimbursement (306).

FIG. 8 depicts a report with annotated treatment options. The markers (targets), status of the markers (targets), and drugs are listed. Annotated information appears in multiple places on the report.

Prophetic Example 6: Stratification and Annotation of a Combination Regimen Drug Treatment Option An oncologist submits an order to a personalized medicine business on behalf of a colon cancer patient. The oncologist submits a tumor biopsy from the colon cancer patient to the personalized medicine business, and the personalized medicine business identifies molecular markers in the sample. FOLFOX is a chemotherapy regimen that can be used to treat colorectal cancer. The FOLFOX treatment regimen includes the drugs folinic acid (leucovorin), fluorouracil (5-FU), and oxaliplatin (Eloxatin). The molecular marker information in the sample from a colon cancer patient indicates that two of the drugs in FOLFOX will be efficacious, while the molecular marker information indicates that one of the drugs will not. The personalized medicine business highlights the drug in yellow in the list of drug treatment options, and annotates the report with scientific information. A computer downloadable report is prepared by the personalized medicine business and transmitted to the subject and the subject's oncologist with the FOLFOX drug listing highlighted in yellow. When the subject or the oncologist click on the FOLFOX drug listing, a pop-up box appears that indicates the two drugs in the FOLFOX regimen that are likely to be efficacious and the one drug that is not likely to be efficacious in treating the subject.

Prophetic Example 7: Platinum-Based Drug Treatment Options

Platinum-based drug treatment options include cisplatin, caroplatin, picoplatin, satraplatin, oxaliplatin. The efficacy or resistance of some platinum-based therapies can be correlated with certain expression profiles. A platinum-based drug is listed as a drug treatment option in a report and is annotated to indicate which expression profiles are correlated with efficacy or resistance.

Prophetic Example 8: An Aspect of a Method of the Provided Invention

A health care provider performs a diagnostic biopsy of a primary tumor in a subject. A therapy is begun, and the tumor is tested for the status of one or more molecular markers (402). An order is placed to the personalized medicine business (404). A physician places the order, or assists the subject (e.g., cancer patient) in placing the order. The order can contain clinical information and molecular information regarding the subject and the tumor of the subject at the time the order is placed (404). The order can be placed on a website (404). The clinical and/or molecular information is transmitted to the personalized medicine business via one or more paper documents, emails, or facsimiles. A customer service representative employed by the personalized medicine business processes the order and a research nurse processes the clinical and molecular information (404).

One or more kits are sent by the personalized medicine business before the second biopsy (406). The patient and an oncologist are notified that a kit is sent to a pathologist, and the patient and the oncologist are notified that a kit is sent to a surgeon (406). The kit sent to the pathologist contains instructions for preparing a diagnostic paraffin primary biopsy, an envelope for sending the sample to the personalized medicine business, and identifier information (406). The kit sent to the surgeon contains RNAlater® and instructions for freezing the sample (406). A kit is presented to the pathologist after the surgery (406). A logistics and operations team employed by the personalized medicine business sends the kits (406), and a fee is charged for sending the kits (406).

A biopsy of the sample is performed by a surgeon and the sample is frozen (408). The frozen sample is sent by FedEx in a box with dry ice (406). The frozen tissue is sent in a tube, and a blood sample from the patient is sent to the personalized medicine business for analyzing metabolism genes (406). Specific directions are provided for sending the sample (406). Parafilm embedded, frozen, and/or fine needle biopsies are sent to the personalized medicine business (406).

A pathologist reviews or blocks the samples (410). Cancer cells are purified from a sample that is sent (412). The cancer cells are purified by flow sorting (using markers and/or ploidy) or by laser capture microscopy (412). Two full-time employees (FTE) of the personalized medicine business are available to purify the cancer cells. A fee is charged in exchange for purifying the cancer cells.

Cells, e.g., circulating tumor cells, can be isolated from a sample, e.g., blood, using technology from, e.g., CELLective Dx Corporation.

The purified cancer cells are analyzed by a variety of assays by the personalized medicine business. The personalized medicine business performs targeted assays dependent on the tumor type (414). A logistics and operations employee and two laboratory technicians perform these services (414). A fee is charged for the services (414). Some of the targeted assays are outsourced (414).

The personalized medicine business performs whole genome analysis assays (416). These assays include comparative genomic hybridization (CGH), high density expression, analysis for small nucleotide polymorphisms (SNPs), proteins assays, and sequencing (416). Up to six laboratory technicians perform these tests, and a fee is charged in exchange for performing these tests.

Molecular tests are performed to analyze drug metabolism genes (418). These tests include the Affymetrix® Drug Metabolizing Enzymes and Transporters (DMET)—Early Access Solution, Human1M BeadChip from Illumina®, Human1M-Duo DNA Analysis BeadChip from Illumina®, HumanExon510S-Duo DNA Analysis BeadChip from Illumina®, and the Roche® AmpliChip CYP450 Test (418). Laboratory technicians employed by the personalized medicine business perform the tests. The personalized medicine business charges a fee in exchange for performing the tests.

Other in vitro and in vivo assays are outsourced by the personalized medicine business to another company (420).

The information from the targeted assays, whole genome assays, drug metabolism tests, and/or in vitro and in vivo assays are provided to Ingenuity®. Ingenuity® as well as bioinformatics employees of the personalized medicine business identify scientific information related to cancer drugs and the status of the molecular markers in the patient's sample(s) (422). A molecular pathologist and research nurse annotate the drug information with links to appropriate scientific literature (424). A report is sent to an oncologist (426).

Prophetic Example 9: Drug Treatment Recommendations

A cancer patient contacts a personalized medicine business to obtain a report regarding personalized drug treatment options based on the status of molecular markers in his tumor. The cancer patient submits a sample to the personalized medicine business. DNA is extracted from the sample and is subjected to massively parallel DNA sequencing. The sample is also subjected to qPCR. The sequence of Kras is determined and EGFR copy number is determined. The Kras sequence is determined to be wild-type, and EGFR copy number is determined to be higher than normal. A report is prepared in which cetuximab (Erbitux) and panitumumab (Vectibix) are recommended for the colon cancer patient. The drug treatment option names are highlighted in green on the report. Each drug treatment option is annotated with a number for a footnote, which list references that support the use of cetuximab (Erbitux) and panitumumab (Vectibix) for cancer patients with tumors with wild-type Kras and increased EGFR copy number.

What is claimed is:

1. A method comprising:
   (a) obtaining a cell-free deoxyribonucleic acid (DNA) sample from a subject wherein said cell-free DNA sample comprises molecular markers;
   (b) detecting sequences of a panel of said molecular markers, wherein said molecular markers comprise: (1) Receptor Tyrosine Kinase KIT Proto-Oncogene (KIT); (2) Epidermal Growth Factor Receptor (EGFR) gene; and (3) another molecular marker selected from the group consisting of GTPase KRAS Proto-Oncogene (KRAS), Serine/Threonine Kinase B-Raf Proto-Oncogene (BRAF), a microsatellite sequence, chromosome 18q allelic loss, thymidylate synthase gene, and DNA Topoisomerase I (TOP1) gene; and
   (c) providing a cancer treatment option in a report based on said sequences of said panel of said molecular markers.

2. The method of claim 1, wherein said subject is suspected of having cancer.

3. The method of claim 1, wherein said subject has a cancer.

4. The method of claim 3, wherein said subject has a lung cancer, a non-small-cell lung cancer, a breast cancer, a prostate cancer, a gastric cancer, a head and neck cancer, an advanced gastric adenocarcinoma, a squamous cell carcinoma, a pancreatic adenocarcinoma, Hodgkin's Disease, non-Hodgkin's lymphoma; a testicular carcinoma, a colon cancer, a rectal cancer, an esophageal cancer, a hepatocellular carcinoma, a cholangiocarcinoma, a chronic myeloid leukemia, a chronic lymphocytic leukemia, a small lymphocytic lymphoma, or a follicular lymphoma.

5. The method of claim 1, wherein said cell-free DNA sample comprises blood.

6. The method of claim 1, wherein said cell-free DNA sample comprises genomic DNA.

7. The method of claim 1, further comprising detecting a presence or absence of a substitution, an insertion, a deletion, a rearrangement, a de novo mutation, a nonsense mutation, a missense mutation, a silent mutation, a frameshift mutation, a gene amplification, an interstitial deletion, a chromosomal inversion, a loss of heterozygosity, a loss of function mutation, a gain of function mutation, or a dominant negative mutation in said sequences of said panel of said molecular markers.

8. The method of claim 1, further comprising detecting a presence or absence of a point mutation, a single nucleotide polymorphism, a copy number variation, or a chromosomal translocation in said sequences of said panel of said molecular markers.

9. The method of claim 1, further comprising, prior to (b), amplifying said panel of said molecular markers from said cell-free DNA sample.

10. The method of claim 1, wherein said cancer treatment option comprises imatinib, cetuximab, panitumumab, adjuvant therapy, 5-fluorouracil (5-FU), or temzolomide.

11. The method of claim 1, wherein said subject has had a relapse of a cancer.

12. The method of claim 1, wherein said KIT has or encodes an activating mutation.

13. The method of claim 1, wherein said KRAS has a mutation in exon 2.

14. The method of claim 1, wherein said BRAF encodes a V600E mutation.

15. The method of claim 1, wherein said microsatellite sequence has low-frequency microsatellite instability.

16. The method of claim 1, wherein said microsatellite sequence has high-frequency microsatellite instability.

17. The method of claim 1, wherein a copy number of said EGFR gene is increased relative to normal.

18. The method of claim 1, wherein said EGFR gene has mutations in exons 18-21.

19. The method of claim 1, wherein (b) comprises massively parallel DNA sequencing.

* * * * *